(12) United States Patent
Chung et al.

(10) Patent No.: US 9,155,690 B2
(45) Date of Patent: Oct. 13, 2015

(54) COMPOUND HAVING SKIN-WHITENING, ANTI-OXIDIZING AND PPAR ACTIVITIES AND MEDICAL USE THEREOF

(71) Applicant: Pusan National University Industry-University Cooperation Foundation, Gyeongsan-si, Gyeongsangbuk-do (KR)

(72) Inventors: Hae Young Chung, Busan (KR); Min Hi Park, Busan (KR); Young Mi Ha, Busan (KR); Yu Kyeong Han, Busan (KR); Ji Young Park, Busan (KR); Yun Jung Park, Busan (KR); Jin Ah Kim, Busan (KR); Ji Yeon Lee, Gyeongsangnam-do (KR); Yu Min Song, Busan (KR); Hyung Ryong Moon, Busan (KR)

(73) Assignee: PUSAN NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 0 days.

(21) Appl. No.: 14/504,445

(22) Filed: Oct. 2, 2014

(65) Prior Publication Data
US 2015/0017111 A1    Jan. 15, 2015

Related U.S. Application Data

(63) Continuation of application No. 13/984,567, filed as application No. PCT/KR2012/000935 on Feb. 8, 2012, now Pat. No. 8,889,881.

(30) Foreign Application Priority Data

Feb. 9, 2011    (KR) .................... 10-2011-0011544

(51) Int. Cl.
| | | |
|---|---|---|
| A61Q 19/02 | (2006.01) | |
| A61K 8/49 | (2006.01) | |
| C07D 235/18 | (2006.01) | |
| C07D 277/06 | (2006.01) | |
| C07D 277/66 | (2006.01) | |
| A61K 31/426 | (2006.01) | |
| A61Q 19/06 | (2006.01) | |

(52) U.S. Cl.
CPC ............... *A61K 8/49* (2013.01); *A61K 8/4946* (2013.01); *A61K 31/426* (2013.01); *A61Q 19/02* (2013.01); *C07D 235/18* (2013.01); *C07D 277/06* (2013.01); *C07D 277/66* (2013.01); *A61K 2800/78* (2013.01); *A61Q 19/06* (2013.01)

(58) Field of Classification Search
None
See application file for complete search history.

(56) References Cited

U.S. PATENT DOCUMENTS

| | | | |
|---|---|---|---|
| 3,658,829 A | 4/1972 | Nakamura et al. | |
| 4,020,165 A | 4/1977 | Hubbard et al. | |
| 4,584,407 A | 4/1986 | Hollowood | |
| 5,846,988 A | 12/1998 | Hellberg | |
| 6,068,834 A * | 5/2000 | Kvalnes et al. | 424/62 |
| 6,861,533 B2 | 3/2005 | Chang et al. | |
| 7,078,421 B2 | 7/2006 | Zhao et al. | |
| 7,166,274 B2 * | 1/2007 | Candau | 424/59 |
| 7,858,783 B2 | 12/2010 | Suh et al. | |
| 8,236,288 B2 * | 8/2012 | Mehta et al. | 424/59 |
| 2005/0043398 A1 | 2/2005 | Carola et al. | |

FOREIGN PATENT DOCUMENTS

| | | |
|---|---|---|
| JP | 2002/012535 A * | 1/2002 |
| WO | 2004/063155 A1 | 7/2004 |
| WO | 2006/020916 A3 | 2/2006 |
| WO | WO-2013/033520 A1 * | 3/2013 |

OTHER PUBLICATIONS

Tsuji et al., CA 136:74330, 2002.*
PubChemCompund, datasheet [online compound summary] Retrieved from the Internet: URL: http://pubchem,ncbi.nlm.nih.gov/search/search.cgi>, PubChem CID 20706, Mar. 26, 2005.
Taihei Yamane et al., "Highly regioselective direct halogenation: a simple and efficient method for preparing . . . ", Terahedron Letters, 2004, vol. 45, pp. 69-73, ISSN 0040-4039.
Colagiuri et al., American Journal of Public Health, Sep. 2006, vol. 96, No. 9, pp. 1562-1569.
Bruno et al., Expert Opinion Emerging Drugs, (2005), 10(4), pp. 747-771.
Park, Diabetes Research and Clinical Practice 66S (2004), S33-S35.
Curtis et al., The Journal of the American Board of Family Practice, vol. 18, pp. 37-43, (2005).

* cited by examiner

*Primary Examiner* — Laura L. Stockton
(74) *Attorney, Agent, or Firm* — Revolution IP, PLLC

(57) ABSTRACT

Provided are a novel compound having skin-whitening, anti-oxidizing and PPAR activities and a medical use thereof, and the compound has skin-whitening activities for the suppression of tyrosinase, and accordingly, is useful for use in skin-whitening pharmaceutical composition or cosmetic products; has anti-oxidant activities, and accordingly, is useful for the prevention and treatment of skin-aging; and has PPAR activities, and in particular, PPARα and PPARγ activities, and accordingly, is useful for use in pharmaceutical compositions or health foods which are effective for the prevention and treatment of obesity, metabolic disease, or cardiovascular disease.

7 Claims, 5 Drawing Sheets

COMPOUND HAVING SKIN-WHITENING, ANTI-OXIDIZING AND PPAR ACTIVITIES AND MEDICAL USE THEREOF

CROSS REFERENCE TO PRIOR APPLICATION

This application is a Continuation application of U.S. patent application Ser. No. 13/984,567 filed on Oct. 7, 2013 under 35 U.S.C. §120, which is a National Stage Application of PCT International Patent Application No. PCT/KR2012/000935 filed on Feb. 8, 2012 under 35 U.S.C. §371, which claims priority to Korean Patent Application No. 10-2011-0011544 filed on Feb. 9, 2011, which are all hereby incorporated by reference in their entirety.

BACKGROUND

The present invention relates to a novel compound having skin-whitening, anti-oxidizing and PPAR activities and a medical use thereof.

Human skin color is determined according to amounts of melanin, carotene, and hemoglobin, and from among them, melanin acts as the most determining factor. Melanin pigment is a phenol-based polymer material that has a composite form of black pigment and protein, and blocks ultraviolet light, and people who lacks melanin pigment is very sensitive to sun light and is highly likely to have burns, and even at young ages, the possibility of skin cancer is high. Generally, short-wave ultraviolet light and carcinogen form a free radical that is harmful for skin. Melanin removes the free radical to protect proteins and genes. Accordingly, the wording that melanin is present in great quintiles means that an effective response system for the protection of skin from physical or chemical toxicity materials is provided.

Melanin has a circulating cycle: melanin is generated from tyrosine due to an action of tyrosinase in pigment cells through complicated processes, the generated melanin is transferred to skin cells and consumed and removed when excoriation occurs. This melanin generation process naturally occurs, and in a normal-state skin, excess melanin is not generated. However, when skin responses to external stimuli, for example, ultraviolet light, environmental pollution, or stress, excess melanin is generated so that melanin is not discharged into outside the skin but is transferred to keratinocyte to accumulate in a skin epidermis, thereby causing serious cosmetic problems, such as melasma, freckle, and senile lentigo, promoting skin aging, and inducing skin cancer.

Meanwhile, research into the prevention of melanin pigmentation in skin has been performed in four aspects. First, a tyrosinase synthesis inhibiting material or an antagonist against a matrix of tyrosinase is developed to control the activity of tyrosinase, which is an apoenzyme for melanin synthesis. Second, a material that has toxicity to melanocyte, in which melanin biosynthesis occurs in animals, is developed to decrease the function of melanocyte. Third, a material that reduces dopa, which is an intermediate metabolic material of a melanin synthesis path, is developed to prevent the oxidation of dopa. Finally, an activity of a first enzyme tyrosinase, which is a melanin generator, an activity of a second enzyme DOPA chrome tautomerase that promotes conversion from DOPA chrome to 5,6-dihydroxyindole-2-carboxyic acid (DHICA), and an activity of a third enzyme that promotes conversion from DHICA to indole-5,6-quinone-2-carboxylic acid are simultaneously reduced.

Recently, women in the Asia region desire to have skin that is as white and clean as white porcelain, and regard the whiteness and cleanness as critical criteria for the evaluation of beauty. Accordingly, the development of whitening agents for the treatment of abnormal skin pigmentation and the satisfaction of cosmetic desires is actively being performed.

As a known method of developing a whitening agent, there are a decoloration method performed by reducing a generated melanin pigment and a method of suppressing activities of tyrosinase, which is an enzyme for forming melanin pigment. However, a whitening agent prepared by using tocopherol or vitamins to reduce melanin pigment is known to have very small decoloration effects. Accordingly, an inhibitor that suppresses the generation of melanin pigment by inhibiting activities of tyrosinase is getting attention.

In conventional cosmetic fields, as a whitening material, for example, a material for suppressing activities of tyrosinase enzyme, such as kojic acid or arbutin, hydroquinone, vitamin C (L-Ascorbic acid) and a derivative thereof, and various plant extracts are used. However, use of these materials is limited due to their low stability in a prescription system, leading to decomposition and pigmentation, generation of offensive odor, uncertainty and stability of efficacy and effectiveness at bio-levels. Also, although kojic acid allows a copper ion present in an active site of tyrosinase to adsorb to inhibit enzymatic activities, when mixed in cosmetic products, instability, skin adverse effects, and liver cancer, which was recently identified based on animal tests, may occur, and accordingly, use of the kojic acid in cosmetic products was stopped. Vitamin C and a derivative thereof are highly likely oxidized, and due to this instability, it is difficult for these materials to be used in cosmetic source materials. Hydroquinone has excellent skin whitening effects. However, it has high skin irritation because hydroquinone causes allergy, has toxicity to melanin forming cells, and induces permanent decoloration of skin. Also, in many countries, hydroquinone is defined as carcinogen, and thus, only limited concentration of thereof is allowed for use. Arbutin is a derivative in which glucopyranoside binds to hydroquinone, and has smaller adverse effects than when hydroquinone is used, and suppresses synthesis of a melanin pigment without toxicity to human body. Due to such characteristics, its use for the treatment of skin disorders, in which melanin pigmentation more occurs, has been suggested. However, arbutin partly decomposes by skin enzyme. Accordingly, there is a need to develop an alternative whitening agent that has high efficiency even at small concentrations, smaller adverse effects, and stability.

Also, reactive oxygen species (ROS) refers to an in vivo toxic material associated with oxygen, and examples of ROS are a free radical, such as superoxide, hydroxyl, peroxyl, alkoxyl, or hydroperoxyl, and a non-free radical, such as hydrogen peroxide, hypochlorous acid, ozone, singlet oxygen, or peroxynitrite.

From among these ROS, regarding oxygen toxicity, a superoxide free radical (reactive oxygen or harmful oxygen) is the most frequently researched thereinto and plays a critical role (Fridorich L., Science, 201, pp 175-180, 1978). A free radical, which is a strong oxidizing gent, is an unpaired electron. A free radical is generated during oxidation and reduction reactions of various organisms, and may cause deterioration of eatable oil, or may oxidatively damage on various biomaterials (lipid, protein, nucleic acid, carbohydrate) and through various steps, ultimately, mutants may occur (Yen G C et al., J. Agric. Food Chem., 43, pp 27-32, 1995). Regarding an unsaturated fatty acid of phosphatide which constitutes a biological membrane, a free radical, such as reactive oxygen species, initiates a peroxidative reaction and also the reaction is proceeds consecutively. Accordingly, a peroxidative reaction due to the free radical may increase permeability of a cell membrane and cause overall cytotoxicity, thereby inducing aging or pathological phenomenon of aging-associated disorders to be engaged in cancer generation process. The action of a radical heavily affects progress of various chronic disease, such as atopic disease, cancer, hypertension, myocardial infarction, arteriosclerosis, rheumatis, cataract, Parkinson's disease, which are disorders associated with oxidative stress (DeSouza L C et al., Bioorg. Med. Cehm. Lett., 14, pp 5859-5861, 2004), and may weaken the function of an immune system (Pike J et al., Int. J. Vitam. Nutr. Res., 65, pp 117-120, 1995).

Accordingly, anti-oxidation evaluation on an alternative material for the prevention from the oxidative damage is very actively performed. Antioxidants do not remove or absorb oxygen, but react with a free radical so that loss of particular vitamins and necessary amino acids is minimized, and corruption of oil product is delayed or prevented. As a synthetic antioxidant used in foods and medical products, butylated hydroxyanisole (BHA), butylated hydroxytoluene (BHT), propyl galate (PG), and tertiary-butyl hydroquinone (TBHQ) may be used. However, when these antioxidants are administered at high concentrations into test animals, hepatomegaly or cancer may progress. In particular, butylated hydroxytoluene is known to, based on various study results, increase enzymatic activity (microsomal enzyme activity in the liver of lab animals), and thus, stability of these phenol-based synthesis antioxidants is debated, and currently, available amounts thereof are legally limited (Brannen A L, J. Amer. Oil Chem. Soc., 52, pp 59-63, 1975; Ito N et al., J. Natl. Cancer Inst., 70, p 343, 1983; Chan K M et al., J. Food. Sci., 58, pp 1-4, 1993). In response, much research into vegetable-originated natural antioxidants that have high antioxidant effects, are stable, and are prepared at low costs is being performed (Larson R A, Phytochemistry, 27, pp 969-978, 1988). Alongside the recent research into natural materials, secondary metabolite that is included in natural materials is getting attention as a bioactive material, and in particular, research into antioxidants is actively being performed, and examples of known natural antioxidants are tocopherols, flavonoids, gossypols, sesamols, oryzanol, and vitamin C (Huson B et al., Food Chem., 19, pp 537-541, 1987; Frankel, E. N. Food Chem., 57, p 51, 1996; Giese J, Food Technol., 5, pp 73-81, 1996; Pszcczola D E, Food Tech., 55, pp 51-59, 2001). In particular, tocopherol and L-ascorbic acid are preferred as a natural antioxidant, however, despite its high stability, when used alone, tocopherol has a low oxidation prevention ability (Halliwell B et al., FASEB J., 2, pp 2867-2870, 1988) and is expensive.

Meanwhile, peroxisome is one of intracellular organelles which cause abnormal metabolism functions, and plays a critical role in metabolism of oxygen, glucose, lipid, and hormone, and widely affects controlling of cell proliferation and differentiation, and inflammatory mediators. Also, peroxisome affects, through lipid metabolism and glucose metabolism, insulin sensitivity, the formation of a cell membrane and mast cells, and oxidative stress, thereby playing a critical role in aging and tumorigenesis. Peroxisome proliferator-activated receptor (PPAR) is one of nuclear receptors that control the expression of gene due to a ligand binding, and various fatty acids act as an endogenous ligand. Up to now, three PPAR are known: a peroxisome proliferator-activated receptor alpha (PPARα), a peroxisome proliferator-activated receptor beta (PPARβ/δ), and a peroxisome proliferator-activated receptor gamma (PPARγ)

PPARα generally exists in blood vessel walls, the liver, the heart, muscle, kidney, and brown adipose tissues, and together with fibrates, which is an agonist, PPARα prevents or delays progress of arteriosclerosis, promotes oxidizing fat to prevent obesity. PPARβ or PPARδ generally exists skin, brain or adipose tissues, is engaged in cholestrol antiport, myelination, and cut recovery, and acts as a controller for fatty acid metabolism and energy homestasis. PPARγ generally exists in adipose tissues, and also in blood vessel endodermis, macrophage, and β cells of pancreas, and controls differentiation of adipocytes and plays a critical role in body lipid homestasis. A completely or incompletely activated compound of PPARγ suppresses differentiation of adipocyte to effectively treat obesity, and the incompletely activated compound is effective for the treatment of hyperglycemia as well as obesity. As described above, to prevent and treat a variety of disease that is controlled by an action of PPAR, there is a need to develop a novel compound to effectively control activities of PPAR.

SUMMARY OF THE INVENTION

Provided are novel compounds having skin-whitening activities.

Provided are novel compounds having anti-oxidant activities.

Provided are novel compounds having PPAR activities.

An embodiment of the present invention provides a compound represented by Formula 1 below:

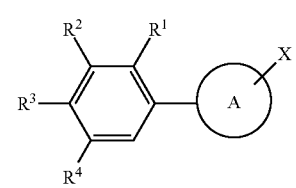

[Formula 1]

wherein $R^1$ to $R^4$ may be identical to or different from each other, and may be any one of H, OH, a $C_1$ to $C_4$ alkoxy, halogen, benzyloxy, acetoxy, O—C($CH_3$)$_2$—COOMe, O—C($CH_3$)$_2$—COOEt, and O—C($CH_3$)$_2$—COOH, X may be any one of H, a $C_1$ to $C_4$ alkyl, $CF_3$, halogen, carboxyl, COOCH$_3$, tert-butyldimethylsilyloxy, (oxylane-2-yl)methoxy, nitro, and methoxybenzyl, and A may be any one of an aromatic ring and a heterocyclic ring, and may be any one selected from the group consisting of thiazole, thiazolidine, dihydrothiazole, benzo[d]thiazole, 1H-benzo[d]imidazole, dithiolane, dihydrobenzo[d]thiazole, 2H-chromene-2-one, 4H-chromene-4-one and benzo[d]oxazole.

The compound according to the present invention may be a compound represented by Formula 2 below:

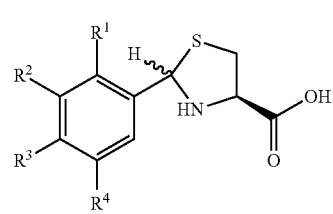

[Formula 2]

wherein $R^1$ to $R^4$ may be identical to or different from each other, and may be any one of H, OH, and a $C_1$ to $C_4$ alkoxy.

The compound according to the present invention may be a compound represented by Formula 3 below:

[Formula 3]

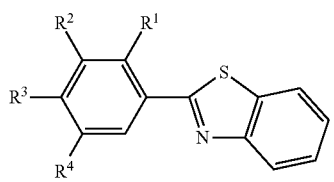

wherein $R^1$ to $R^4$ may be identical to or different from each other, and may be any one of H, OH, a $C_1$ to $C_4$ alkoxy, and bromine.

The compound according to the present invention may be a compound represented by Formula 4 below:

[Formula 4]

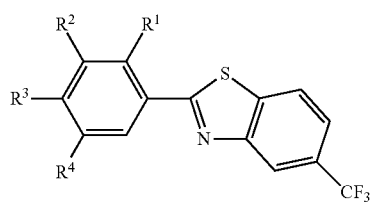

wherein $R^1$ to $R^4$ may be identical to or different from each other, and may be any one of H, OH, a $C_1$ to $C_4$ alkoxy, and bromine.

The compound according to the present invention may be a compound represented by Formula 5 below:

[Formula 5]

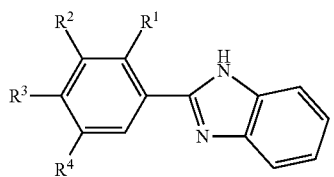

wherein $R^1$ to $R^4$ may be identical to or different from each other, and may be any one of H, OH, a $C_1$ to $C_4$ alkoxy, and bromine.

The compound according to the present invention may be a compound represented by Formula 6 below:

[Formula 6]

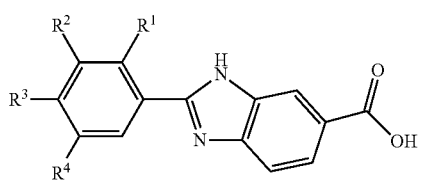

wherein $R^1$ to $R^4$ may be identical to or different from each other, and may be any one of H, OH, a $C_1$ to $C_4$ alkoxy, and bromine.

The compound according to the present invention may be a compound represented by Formula 7 below:

[Formula 7]

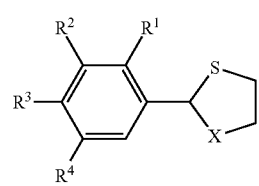

wherein $R^1$ to $R^4$ may be identical to or different from each other and may be any one of H, OH, and a $C_1$ to $C_4$ alkoxy, and X may be any one of NH and S.

The compound according to the present invention may be a compound represented by Formula 8 below:

[Formula 8]

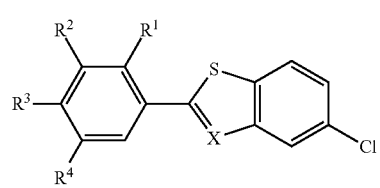

wherein $R^1$ to $R^4$ may be identical to or different from each other, and may be any one of H, OH, a $C_1$ to $C_4$ alkoxy, and bromine.

The compound according to the present invention may be a compound represented by Formula 9 below:

[Formula 9]

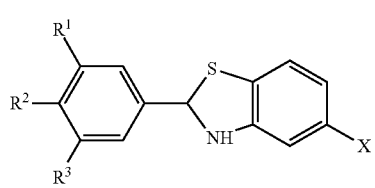

wherein $R^1$ to $R^3$ may be identical to or different from each other, and may be any one of H, OH, a $C_1$ to $C_4$ alkoxy, and bromine, and X may be any one of chlorine and $CF_3$.

The compound according to the present invention may be a compound represented by Formula 10 below:

[Formula 10]

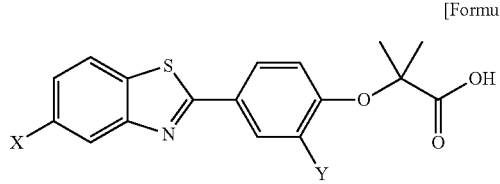

wherein X may be any one of hydrogen, chlorine, and trifluoromethyl, and Y may be any one of hydrogen and methoxy.

The compound according to the present invention may be a compound represented by Formula 11 below:

[Formula 11]

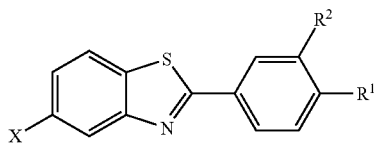

wherein X may be any one of hydrogen, chlorine, and trifluoromethyl, and $R^1$ and $R^2$ are different from each other and may be any one of hydrogen and benzyloxy.

The compound according to the present invention may be a compound represented by Formula 12 below:

[Formula 12]

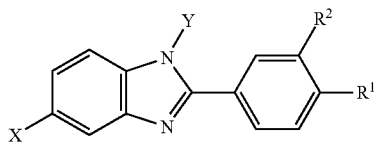

wherein X may be any one of hydrogen and COOH, Y may be any one of hydrogen and methoxybenzyl, and $R^1$ and $R^2$ are different from each other and may be any one of hydrogen, a $C_1$ to $C_4$ alkoxy, and benzyloxy.

The compound according to the present invention may be a compound represented by Formula 13 below:

[Formula 13]

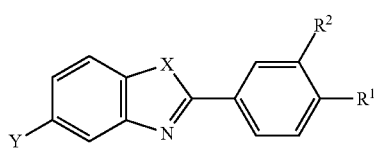

wherein X may be any one of NH, O, and S, Y may be any one of hydrogen and chlorine, and $R_1$ or $R_2$ are different from each other and may be any one of hydrogen, a $C_1$ to $C_4$ alkoxy, O—C(CH$_3$)$_2$—COOMe, O—C(CH$_3$)$_2$—COOEt, and O—C(CH$_3$)$_2$—COOH.

The compound according to the present invention may be a compound represented by Formula 14 below:

[Formula 14]

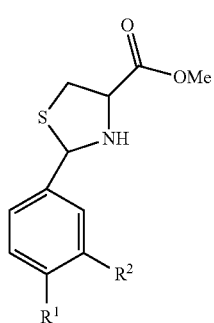

wherein $R^1$ and $R^2$ may be identical to each other, and may be any one of OH and OAc.

The compound according to the present invention may be a compound represented by Formula 15 below:

[Formula 15]

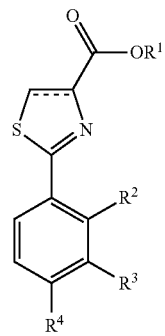

wherein the dotted line (represented by '---') indicates a double bond, $R^1$ may be any one of hydrogen or methyl, and two substitutes selected from $R^2$ through $R^4$ may be identical to each other and the identical substitutes may be any one of OH and OAc and the other one may be hydrogen.

The compound according to the present invention may be a chromene compound selected from the group consisting of 7,8-bis(tert-butyldimethylsilyloxy)-4-phenyl-2H-chromen-2-one (Compound 100), and 3,6-bis((oxiran-2-yl)methoxy)-2-phenyl-4H-chromen-4-one (Compound 106).

The compound according to the present invention may be a compound represented by Formula 16 below:

[Formula 16]

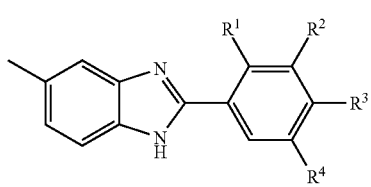

wherein $R^1$ to $R^4$ may be identical to or different from each other, and may be any one of H, OH, and a $C_1$ to $C_4$ alkoxy.

The compound according to the present invention may be a compound represented by Formula 17 below:

[Formula 17]

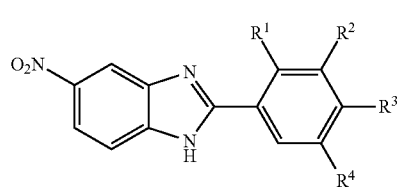

wherein $R^1$ to $R^4$ may be identical to or different from each other, and may be any one of H, OH, and a $C_1$ to $C_4$ alkoxy.

Compounds according to the present invention have skin-whitening activities for the suppression of tyrosinase, and accordingly, may be useful for use in skin-whitening pharmaceutical composition or cosmetic products; have anti-oxidant activities, and accordingly, may be useful for the prevention and treatment of skin-aging; and have PPAR activities, and in particular, PPARα and PPARγ activities, and accordingly, may be useful for use in pharmaceutical compositions or health foods which are effective for the prevention and treatment of obesity, metabolic disease, or cardiovascular disease.

DETAILED DESCRIPTION

Figure 1:
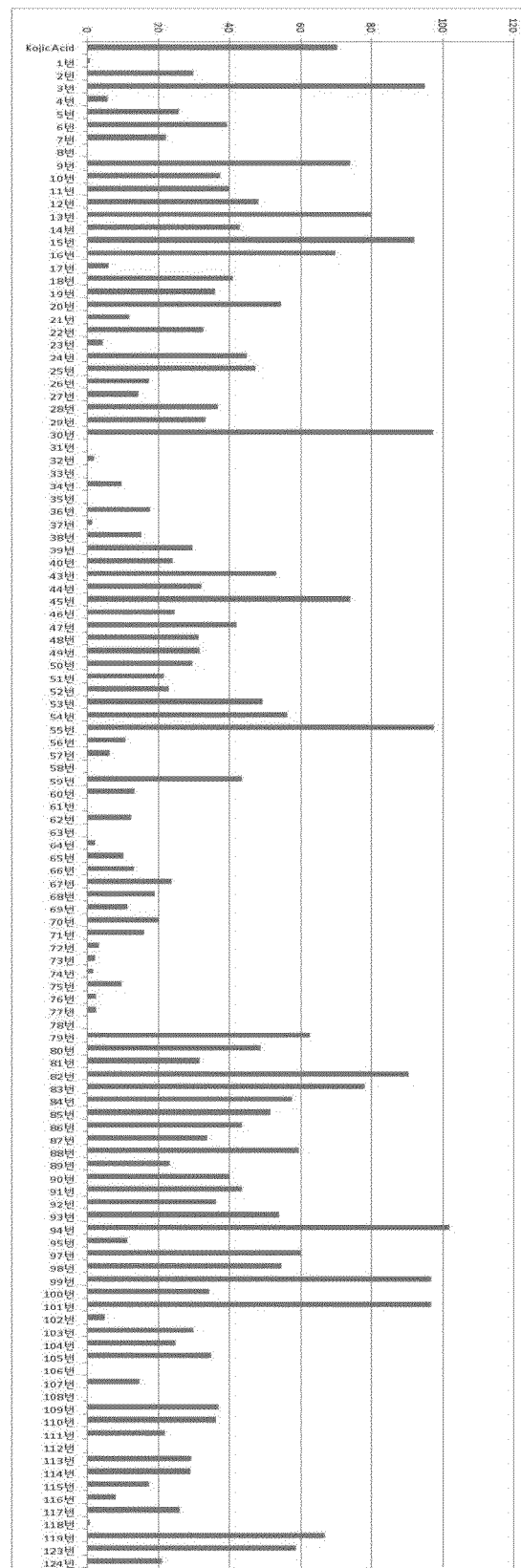
FIGS. 1 and 2 are graphs showing anti-oxidant activities of a compound according to the present invention.

An embodiment of the present invention provides a compound represented by Formula 1 below:

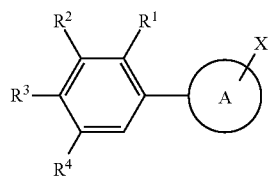

[Formula 1]

wherein $R^1$ to $R^4$ may be identical to or different from each other, and may be any one of H, OH, a $C_1$ to $C_4$ alkoxy, halogen, benzyloxy, acetoxy, O—C(CH$_3$)$_2$—COOMe, O—C(CH$_3$)$_2$—COOEt, and O—C(CH$_3$)$_2$—COOH, X may be any one of H, a $C_1$ to $C_4$ alkyl, CF$_3$, halogen, carboxyl, COOCH$_3$, tert-butyldimethylsilyloxy, (oxylane-2-yl)methoxy, nitro, and methoxybenzyl, and A may be any one of an aromatic ring and a heterocyclic ring, and may be any one selected from the group consisting of thiazole, thiazolidine, dihydrothiazole, benzo[d]thiazole, 1H-benzo[d]imidazole, dithiolane, dihydrobenzo[d]thiazole, 2H-chromene-2-one, 4H-chromene-4-one and benzo[d]oxazole.

The compound according to the present invention may be a compound represented by Formula 2 below:

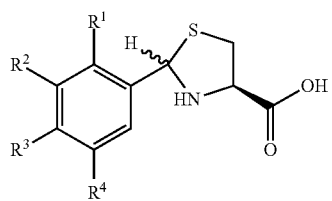

[Formula 2]

wherein $R^1$ to $R^4$ may be identical to or different from each other, and may be any one of H, OH, and a $C_1$ to $C_4$ alkoxy.

In detail, the compound of Formula 2 may be any one selected from the group consisting of (2R/S,4R)-2-(4-hydroxyphenyl)thiazolidine-4-carboxylic acid (Compound 1); (2R/S,4R)-2-(3,4-dihydroxyphenyl)thiazolidine-4-carboxylic acid (Compound 2); (2R/S,4R)-2-(2,4-dihydroxyphenyl)thiazolidine-4-carboxylic acid] (Compound 3); (2R/S,4R)-2-(4-hydroxy-3-methoxyphenyl)thiazolidine-4-carboxylic acid (Compound 4); (2R/S,4R)-2-(3-ethoxy-4-hydroxyphenyl)thiazolidine-4-carboxylic acid (Compound 5); (2R/S,4R)-2-(3-hydroxy-4-methoxyphenyl)thiazolidine-4-carboxylic acid (Compound 6); (2R/S,4R)-2-(4-methoxyphenyl)thiazolidine-4-carboxylic acid (Compound 7); (2R/S,4R)-2-(3,4-dimethoxyphenyl)thiazolidine-4-carboxylic acid (Compound 8); (2R/S,4R)-2-(2,4-dimethoxyphenyl)thiazolidine-4-carboxylic acid (Compound 9); (2R/S,4R)-2-(2-hydroxyphenyl)thiazolidine-4-carboxylic acid (Compound 10); (2R/S,4R)-2-(3,4,5-trimethoxyphenyl)thiazolidine-4-carboxylic acid (Compound 11); and (2R/S,4R)-2-(4-hydroxy-3,5-dimethoxyphenyl)thiazolidine-4-carboxylic acid (Compound 12).

The compound according to the present invention may be a compound represented by Formula 3 below:

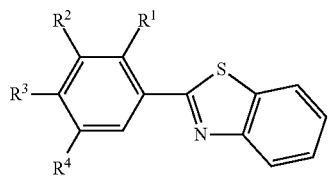

[Formula 3]

wherein $R^1$ to $R^4$ may be identical to or different from each other, and may be any one of H, OH, a $C_1$ to $C_4$ alkoxy, and bromine.

In detail, the compound of Formula 3 may be any one selected from the group consisting of 4-(benzo[d]thiazol-2-yl)phenol] (Compound 13); 4-(benzo[d]thiazol-2-yl)benzene-1,2-diol (Compound 14); 4-(benzo[d]thiazol-2-yl)benzene-1,3-diol (Compound 15); 4-(benzo[d]thiazol-2-yl)-2-methoxyphenol (Compound 16); 4-(benzo[d]thiazol-2-yl)-2-ethoxyphenol (Compound 17); 5-(benzo[d]thiazol-2-yl)-2-methoxyphenol (Compound 18); 2-(4-methoxyphenyl)benzo[d]thiazol (Compound 19); 2-(3,4-dimethoxyphenyl)benzo[d]thiazol (Compound 20); 5-(benzo[d]thiazol-2-yl)benzene-1,3-diol (Compound 21); 2-(2,4-dimethoxyphenyl)benzo[d]thiazol (Compound 22); 2-(benzo[d]thiazol-2-yl)phenol (Compound 23); 2-(3,4,5-trimethoxyphenyl)benzo[d]thiazol (Compound 24); 4-(benzo[d]thiazol-2-yl)-2,6-dimethoxyphenol (Compound 25); 4-(benzo[d]thiazol-2-yl)-2-bromophenol (Compound 26); and 4-(benzo[d]thiazol-2-yl)-2,6-dibromophenol (Compound 27).

The compound according to the present invention may be a compound represented by Formula 4 below:

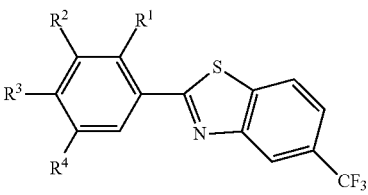

[Formula 4]

wherein $R^1$ to $R^4$ may be identical to or different from each other, and may be any one of H, OH, a $C_1$ to $C_4$ alkoxy, and bromine.

In detail, the compound of Formula 4 may be any one selected from the group consisting of 4-(5-(trifluoromethyl)benzo[d]thiazol-2-yl)phenol (Compound 28); 4-(5-(trifluoromethyl)benzo[d]thiazol-2-yl)benzene-1,2-diol (Compound 29); 4-(5-(trifluoromethyl)benzo[d]thiazol-2-yl)benzene-1,3-diol (Compound 30); 2-methoxy-4-(5-(trifluoromethyl)benzo[d]thiazol-2-yl)phenol (Compound 31); 2-ethoxy-4-(5-(trifluoromethyl)benzo[d]thiazol-2-yl)phenol (Compound 32); 2-methoxy-5-(5-(trifluoromethyl)

benzo[d]thiazol-2-yl)phenol (Compound 33); 2-(4-methoxyphenyl)-5-(trifluoromethyl)benzo[d]thiazol (Compound 34); 2-(3,4-dimethoxyphenyl)-5-(trifluoromethyl)benzo[d]thiazol (Compound 35); 5-(5-(trifluoromethyl)benzo[d]thiazol-2-yl)benzene-1,3-diol (Compound 36); 2-(2,4-dimethoxyphenyl)-5-(trifluoromethyl)benzo[d]thiazol (Compound 37); 2-(5-(trifluoromethyl)benzo[d]thiazol-2-yl)phenol (Compound 38); 5-(trifluoromethyl)-2-(3,4,5-trimethoxyphenyl)benzo[d]thiazol (Compound 39); 2,6-dimethoxy-4-(5-(trifluoromethyl)benzo[d]thiazol-2-yl)phenol (Compound 40); 2-bromo-4-(5-(trifluoromethyl)benzo[d]thiazol-2-yl)phenol (Compound 41); and 2,6-dibromo-4-(5-(trifluoromethyl)benzo[d]thiazol-2-yl)phenol (Compound 42).

The compound according to the present invention may be a compound represented by Formula 5 below:

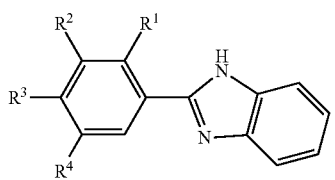

[Formula 5]

wherein $R^1$ to $R^4$ may be identical to or different from each other, and may be any one of H, OH, a $C_1$ to $C_4$ alkoxy, and bromine.

In detail, the compound of Formula 5 may be any one selected from the group consisting of 4-(1H-benzo[d]imidazol-2-yl)phenol (Compound 43); 4-(1H-benzo[d]imidazol-2-yl)benzene-1,2-diol (Compound 44); 4-(1H-benzo[d]imidazol-2-yl)benzene-1,3-diol (Compound 45); 4-(1H-benzo[d]imidazol-2-yl)-2-methoxyphenol (Compound 46); 4-(1H-benzo[d]imidazol-2-yl)-2-ethoxyphenol (Compound 47); 5-(H-benzo[d]imidazol-2-yl)-2-methoxyphenol (Compound 48); 2-(4-methoxyphenyl)-1H-benzo[d]imidazole (Compound 49); 2-(3,4-dimethoxyphenyl)-1H-benzo[d]imidazole (Compound 50); 5-(H-benzo[d]imidazol-2-yl)benzene-1,3-diol (Compound 51); 2-(2,4-dimethoxyphenyl)-1H-benzo[d]imidazole (Compound 52); 2-(1H-benzo[d]imidazol-2-yl)phenol (Compound 53); 2-(3,4,5-trimethoxyphenyl)-1H-benzo[d]imidazole (Compound 54); 4-(1H-benzo[d]imidazol-2-yl)-2,6-dimethoxyphenol (Compound 55); and 4-(1H-benzo[d]imidazol-2-yl)-2-bromophenol (Compound 56).

The compound according to the present invention may be a compound represented by Formula 6 below:

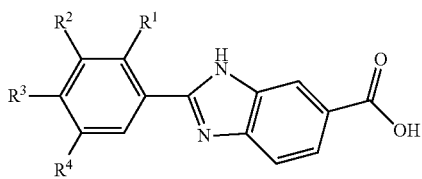

[Formula 6]

wherein $R^1$ to $R^4$ may be identical to or different from each other, and may be any one of H, OH, a $C_1$ to $C_4$ alkoxy, and bromine.

In detail, the compound of Formula 6 may be any one selected from the group consisting of 2-(4-hydroxyphenyl)-1H-benzo[d]imidazole-5-carboxylic acid (Compound 57); 2-(3,4-dihydroxyphenyl)-1H-benzo[d]imidazole-5-carboxylic acid (Compound 58); 2-(2,4-dihydroxyphenyl)-1H-benzo[d]imidazole-5-carboxylic acid (Compound 59); 2-(4-hydroxy-3-methoxyphenyl)-1H-benzo[d]imidazole-5-carboxylic acid (Compound 60); 2-(3-ethoxy-4-hydroxyphenyl)-1H-benzo[d]imidazole-5-carboxylic acid (Compound 61); 2-(3-hydroxy-4-methoxyphenyl)-1H-benzo[d]imidazole-5-carboxylic acid (Compound 62); 2-(4-methoxyphenyl)-1H-benzo[d]imidazole-5-carboxylic acid (Compound 63); 2-(3,4-dimethoxyphenyl)-1H-benzo[d]imidazole-5-carboxylic acid (Compound 64); 2-(2,4-dimethoxyphenyl)-1H-benzo[d]imidazole-5-carboxylic acid (Compound 65); 2-(2-hydroxyphenyl)-1H-benzo[d]imidazole-5-carboxylic acid (Compound 66); 2-(3,4,5-trimethoxyphenyl)-1H-benzo[d]imidazole-5-carboxylic acid (Compound 67); 2-(4-hydroxy-3,5-dimethoxyphenyl)-1H-benzo[d]imidazole-5-carboxylic acid (Compound 68); 2-(3-bromo-4-hydroxyphenyl)-1H-benzo[d]imidazole-5-carboxylic acid (Compound 69); and 2-(3,5-dibromo-4-hydroxyphenyl)-1H-benzo[d]imidazole-5-carboxylic acid (Compound 70).

The compound according to the present invention may be a compound represented by Formula 7 below:

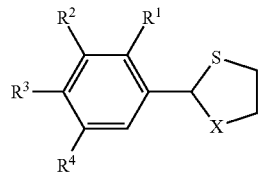

[Formula 7]

wherein $R^1$ to $R^4$ may be identical to or different from each other and may be any one of H, OH, and a $C_1$ to $C_4$ alkoxy, and X may be any one of NH and S.

In detail, the compound of Formula 7 may be any one selected from the group consisting of 4-(thiazolidin-2-yl)phenol (Compound 71); 4-(thiazolidin-2-yl)benzene-1,2-diol (Compound 72); 2-methoxy-4-(thiazolidin-2-yl)phenol (Compound 73); 2-ethoxy-4-(thiazolidin-2-yl)phenol (Compound 74); 2-methoxy-5-(thiazolidin-2-yl)phenol (Compound 75); 2-(4-methoxyphenyl)thiazolidine (Compound 76); 2-(3,4-dimethoxyphenyl)thiazolidine (Compound 77); 2-(2,4-dimethoxyphenyl)thiazolidine (Compound 78); 2-(3,4,5-trimethoxyphenyl)thiazolidine (Compound 79); 2,6-dimethoxy-4-(thiazolidin-2-yl)phenol (Compound 80); and 4-(1,3-dithiolan-2-yl)phenol (Compound 81).

The compound according to the present invention may be a compound represented by Formula 8 below:

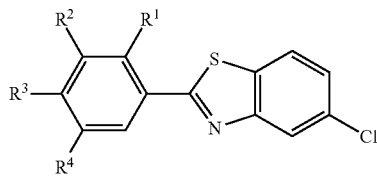

[Formula 8]

$R^1$ to $R^4$ may be identical to or different from each other, and may be any one of H, OH, a $C_1$ to $C_4$ alkoxy, and bromine.

In detail, the compound of Formula 8 may be any one selected from the group consisting of 4-(5-chlorobenzo[d]thiazol-2-yl)phenol (Compound 82); 4-(5-chlorobenzo[d]

thiazol-2-yl)benzene-1,2-diol (Compound 83); 4-(5-chlorobenzo[d]thiazol-2-yl)benzene-1,3-diol (Compound 84); 4-(5-chlorobenzo[d]thiazol-2-yl)-2-methoxyphenol (Compound 85); 4-(5-chlorobenzo[d]thiazol-2-yl)-2-ethoxyphenol (Compound 86); 5-(5-chlorobenzo[d]thiazol-2-yl)-2-methoxyphenol (Compound 87); 5-chloro-2-(4-methoxyphenyl)benzo[d]thiazol (Compound 88); 5-chloro-2-(3,4-dimethoxyphenyl)benzo[d]thiazol (Compound 89); 5-(5-chlorobenzo[d]thiazol-2-yl)benzene-1,3-diol (Compound 90); 5-chloro-2-(2,4-dimethoxyphenyl)benzo[d]thiazol (Compound 91); 2-(5-chlorobenzo[d]thiazol-2-yl)phenol (Compound 92); 5-chloro-2-(3,4,5-trimethoxyphenyl)benzo[d]thiazol (Compound 93); 2-bromo-4-(5-chlorobenzo[d]thiazol-2-yl)phenol (Compound 95); 2,6-dibromo-4-(5-chlorobenzo[d]thiazol-2-yl)phenol (Compound 96); and 4-(5-chlorobenzo[d]thiazol-2-yl)-2,6-dimethoxyphenol (Compound 126).

The compound according to the present invention may be a compound represented by Formula 9 below:

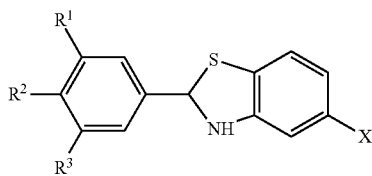

[Formula 9]

wherein $R^1$ to $R^3$ may be identical to or different from each other, and may be any one of H, OH, a $C_1$ to $C_4$ alkoxy, and bromine, and X may be any one of chlorine and $CF_3$.

In detail, the compound of Formula 9 may be any one selected from the group consisting of 4-(5-chloro-2,3-dihydrobenzo[d]thiazol-2-yl)-2,6-dimethoxyphenol (Compound 94); and 2-bromo-4-(5-(trifluoromethyl)-2,3-dihydrobenzo[d]thiazol-2-yl)phenol (Compound 119).

The compound according to the present invention may be a compound represented by Formula 10 below:

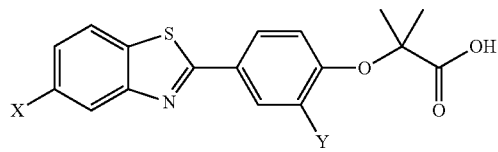

[Formula 10]

wherein X may be any one of hydrogen, chlorine, and trifluoromethyl, and Y may be any one of hydrogen and methoxy.

In detail, the compound of Formula 10 may be any one selected from the group consisting of 2-(4-(benzo[d]thiazol-2-yl)phenoxy)-2-methylpropanoic acid (Compound 97); 2-methyl-2-(4-(5-(trifluoromethyl)benzo[d]thiazol-2-yl)phenoxy)propanoic acid (Compound 98); 2-(4-(5-chlorobenzo[d]thiazol-2-yl)phenoxy)-2-methylpropanoic acid (Compound 99); and 2-(4-(benzo[d]thiazol-2-yl)-2-methoxyphenoxy)-2-methylpropanoic acid (Compound 122)

The compound according to the present invention may be a compound represented by Formula 11 below:

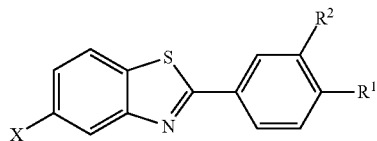

[Formula 11]

wherein X may be any one of hydrogen, chlorine, and trifluoromethyl, and $R^1$ and $R^2$ are different from each other and may be any one of hydrogen and benzyloxy.

In detail, the compound of Formula 11 may be any one selected from the group consisting of 2-(4-(benzyloxy)phenyl)benzo[d]thiazol (Compound 107); 2-(4-(benzyloxy)phenyl)-5-(trifluoromethyl)benzo[d]thiazol (Compound 108); 2-(4-(benzyloxy)phenyl)-5-chlorobenzo[d]thiazol (Compound 109); 2-(3-(benzyloxy)phenyl)benzo[d]thiazol (Compound 110); 2-(3-(benzyloxy)phenyl)-5-(trifluoromethyl)benzo[d]thiazol (Compound 111); and 2-(3-(benzyloxy)phenyl)-5-chlorobenzo[d]thiazol (Compound 112).

The compound according to the present invention may be a compound represented by Formula 12 below:

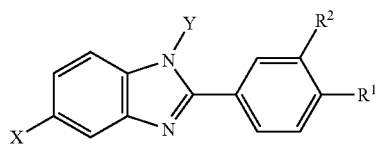

[Formula 12]

wherein X may be any one of hydrogen and COOH, Y may be any one of hydrogen and methoxybenzyl, and $R^1$ and $R^2$ are different from each other and may be any one of hydrogen, a $C_1$ to $C_4$ alkoxy, and benzyloxy.

In detail, the compound of Formula 12 may be any one selected from the group consisting of 2-(4-(benzyloxy)phenyl)-1H-benzo[d]imidazole-5-carboxylic acid (Compound 113); 2-(4-(benzyloxy)phenyl)-1H-benzo[d]imidazole (Compound 114); 2-(3-(benzyloxy)phenyl)-1H-benzo[d]imidazole (Compound 115); 1-(4-methoxybenzyl)-2-(4-methoxyphenyl)-1H-benzo[d]imidazole (Compound 116); and 2-(3-(benzyloxy)phenyl)-1H-benzo[d]imidazole-5-carboxylic acid (Compound 125).

The compound according to the present invention may be a compound represented by Formula 13 below:

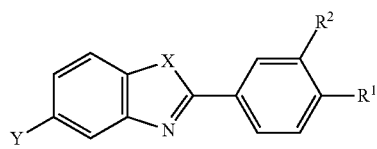

[Formula 13]

wherein X may be any one of NH, O, and S, Y may be any one of hydrogen and chlorine, and $R_1$ or $R_2$ are different from each other and may be any one of hydrogen, a $C_1$ to $C_4$ alkoxy, O—C(CH$_3$)$_2$—COOMe, O—C(CH$_3$)$_2$—COOEt, and O—C(CH$_3$)$_2$—COOH.

In detail, the compound of Formula 13 may be any one selected from the group consisting of 2-(3-(1H-benzo[d]imidazol-2-yl)phenoxy)-2-methylpropanoic acid (Compound 117); 2-(3-(1H-benzo[d]imidazol-2-yl)phenoxy)-2-methylpropanoic acid (Compound 118); 2-(3-(benzo[d]thiazol-2- yl)phenoxy)-2-methylpropanoic acid (Compound 120); 2-(3-(5-chlorobenzo[d]thiazol-2-yl)phenoxy)-2-methylpropanoic acid (Compound 121); 4-(benzo[d]oxazol-2-yl)phenol (Compound 123); and 2-(4-methoxyphenyl)benzo[d]oxazole (Compound 124).

The compound according to the present invention may be a compound represented by Formula 14 below:

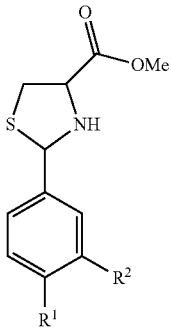

[Formula 14]

wherein $R^1$ and $R^2$ may be identical to each other, and may be any one of OH and OAc.

In detail, the compound of Formula 14 may be any one selected from the group consisting of (2R/S,4R)-methyl 2-(3,4-dihydroxyphenyl)thiazolidine-4-carboxylate (Compound 104); and 4-((2R/S,4R)-4-(methoxycarbonyl)thiazolidin-2-yl)-1,2-phenylene diacetate (Compound 105).

The compound according to the present invention may be a compound represented by Formula 15 below:

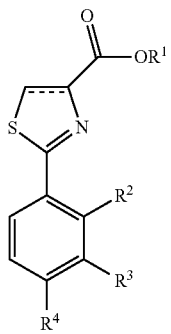

[Formula 15]

wherein the doted line (represented by '---') indicates a double bond, $R^1$ may be any one of hydrogen and methyl, and two substitutes selected from $R^2$ through $R^4$ may be identical to each other and the identical substitutes may be any one of OH and OAc and the other one may be hydrogen.

In detail, the compound of Formula 15 may be any one selected from the group consisting of 2-(2,4-dihydroxyphenyl)thiazol-4-carboxylic acid (Compound 101); (4R)-2-(3,4-dihydroxyphenyl)-4,5-dihydrothiazol-4-carboxylic acid (Compound 102); and 4-(4-(methoxycarbonyl)thiazol-2-yl)-1,2-phenylene diacetate (Compound 103).

The compound according to the present invention may be a chromene compound selected from the group consisting of 7,8-bis(tert-butyldimethylsilyloxy)-4-phenyl-2H-chromen-2-one (Compound 100), and 3,6-bis((oxiran-2-yl)methoxy)-2-phenyl-4H-chromen-4-one (Compound 106).

The compound according to the present invention may be a compound represented by Formula 16 below:

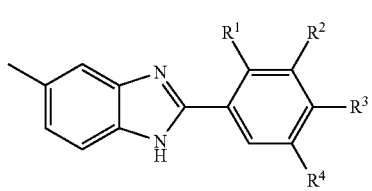

[Formula 16]

wherein $R^1$ to $R^4$ may be identical to or different from each other, and may be any one of H, OH, and a $C_1$ to $C_4$ alkoxy.

In detail, the compound of Formula 16 may be any one selected from the group consisting of 4-(5-methyl-1H-benzo[d]imidazol-2-yl)phenol (Compound 127); 4-(5-methyl-1H-benzo[d]imidazol-2-yl)benzene-1,2-diol (Compound 128); 4-(5-methyl-1H-benzo[d]imidazol-2-yl)benzene-1,3-diol (Compound 129); 2-methoxy-4-(5-methyl-1H-benzo[d]imidazol-2-yl)phenol (Compound 130); 2-(4-methoxyphenyl)-5-methyl-1H-benzo[d]imidazole (Compound 131); 2-(3,4-dimethoxyphenyl)-5-methyl-1H-benzo[d]imidazole (Compound 132); and 2-(2,4-dimethoxyphenyl)-5-methyl-1H-benzo[d]imidazole (Compound 133).

The compound according to the present invention may be a compound represented by Formula 17 below:

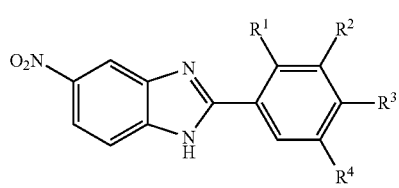

[Formula 17]

wherein $R^1$ to $R^4$ may be identical to or different from each other, and may be any one of H, OH, and a $C_1$ to $C_4$ alkoxy.

In detail, the compound of Formula 17 may be any one selected from the group consisting of 4-(5-nitro-1H-benzo[d]imidazol-2-yl)phenol (Compound 134); 2-methoxy-4-(5-nitro-1H-benzo[d]imidazol-2-yl)phenol (Compound 135); 2-methoxy-5-(5-nitro-1H-benzo[d]imidazol-2-yl)phenol (Compound 136); 2-(4-methoxyphenyl)-5-nitro-1H-benzo[d]imidazole (Compound 137); and 2,6-dimethoxy-4-(5-nitro-1H-benzo[d]imidazol-2-yl)phenol (Compound 138).

The compound may be provided in the form of pharmaceutically acceptable salts thereof, and for example, may be provided in any salt form selected from the group consisting of hydrochloride, bromate, sulphate, phosphate, nitrate, citrate, acetate, lactate, tartarate, maleate, gluconate, succinate, formate, trifluoroacetate, oxalate, fumarate, methane sulfonate, benzene sulfonate, p-toluene sulfonate, and camphor sulfonate.

Also, the present invention provides a composition for skin-whitening including the compound as an active ingredient. The composition may be a pharmaceutical composition or a cosmetic material.

Also, the present invention provides a composition for the prevention or treatment of oxidation-related disease, the composition including the compound as an active ingredient. The composition may be a pharmaceutical composition or a health food.

The oxidation-related disease may be any one of skin aging, skin pigmentation, wrinkle, psoriasis, and eczema.

Also, the present invention provides a composition for the prevention and treatment of a disease that is regulated by a peroxisome proliferator-activated receptor (PPAR), the composition including the compounds as an active ingredient. The composition may be a pharmaceutical composition or a health food.

The PPAR may be a peroxisome proliferator-activated receptor alpha (PPARα) or a peroxisome proliferator-activated receptor gamma (PPARγ), and the disease may be any one of obesity, metabolic disease, and cardiovascular disease.

The metabolic disease may be any one selected from hyperlipidemia, diabetes, hyperinsulinemia, hyperuricemia, hypercholesterolemia, hyper-triglyceridemia, Syndrome X, and endothelial dysfunction, and the cardiovascular disease may be any one selected from hypertension, precoagulant state, dyslipidemia, and atherosclerosis disease.

The pharmaceutical composition according to the present invention may further include appropriate carriers, expedient, or diluents which are conventionally used in preparing pharmaceutical compositions.

Examples of carriers, expedient, or diluents that are available for use in the pharmaceutical composition according to the present invention are lactose, dextrose, sucrose, sorbitol, mannitol, xylitol, erythritol, maltitol, starch, Acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oils.

The pharmaceutical composition according to the present invention may be prepared into an oral formulation, such as a powder formulation, a granule formulation, a tablet formulation, a capsule formulation, a suspension formulation, an emulsion formulation, a syrup formulation, or an aerosol formulation, an external formulation, a suppository formulation, or a sterilized injection solution formation, according to conventional methods.

When prepared into various formulations, a conventional diluent or expedient, such as a filler, a bulking agent, a binding agent, a wetting agent, an disintegrating agent, or a surfactant, may be used. A solid formulation for oral administration may be a tablet formulation, a pill formulation, a powder formulation, a granule formulation, or a capsule formulation, and such solid formulations may be prepared by mixing the compound with one or more expedients selected from, for example, starch, calcium carbonate, sucrose, lactose, and gelatin.

Also, in addition to such expedients, a lubricating agent, such as magnesium stearate or talc, may be used. A liquid formulation for oral administration may be a suspension formulation, an internal solution formulation, an oil formulation, or a syrup formulation, and the liquid formulation may include, in addition to a conventional diluent, such as water or liquid paraffin, various other expedients, for example, a wetting agent, a sweetening agent, a perfuming agent, or a preservative.

A formulation for non-oral administration may be a sterilized aqueous solution formulation, a non-aqueous solution formulation, a suspension formulation, an oil formulation, a lyophilized formulation, or a suppository formulation. For use as the non-aqueous solution formulation and the suspension formulation, propyleneglycol, polyethylene glycol, vegetable oil, such as olive oil, an injectable ester such as ethylolate may be used. As a substrate for the suppository formulation, Witepsol, Macrogol, twin 61, cacao butter, laurin butter, or glycerogelatin may be used.

A dosage of the compound, which is an active ingredient of the pharmaceutical composition according to the present invention, may vary according to the age, gender, body weight, and disease of a patient, and the compositions may be administered in an amount of 0.001 to 100 mg/kg, or 0.01 to 10 mg/kg daily in a bolus or in multiple doses.

Also, a dosage of the compound according to the present invention may vary according to administration path, severance of disease, gender, body weight, or age. Accordingly, the dosage does not limit the scope of the present invention in any aspects.

The pharmaceutical composition may be administered via various pathways to mammal, such as rats, mice, livestock, or humans. All of the administration methods are predictable, and for example, the dosage may be may be orally administered, or the dosage may be administered by rectal or intravenous, nasal, muscular, subcutaneous, intrauterine subdural or intracerebroventricular injection.

The compound according to the present invention has a 50% lethal concentration ($LC_{50}$) of 2 g/kg or more, and thus stability thereof is guaranteed. Accordingly, the compound may be used in a pharmaceutical composition according to the present invention.

Also, the cosmetic composition may include, in addition to the compound according to the present invention, which is an active ingredient, a conventional auxiliary, such as a stabilizer, a solubilizing agent, a vitamin, a pigment, and a fragment, and a perfume.

The cosmetic composition may be prepared in any formulation that is conventionally used in the art. For example, the cosmetic composition may be prepared in the formulation of, for example, solution, suspension, emulsion, paste, gel, cream, lotion, powder, oil, powder foundation, emulsion foundation, wax foundation, and spray, but the formulation thereof is not limited thereto. That is, the cosmetic composition may be prepared in the formulation of sun cream, softening cosmetic water, convergence cosmetic water, nutrition cosmetic water, nutrition cream, massage cream, essence, eye cream, pack, spray, or powder.

When the formulation is paste, cream, or gel, an available carrier component may be, for example, animal oil, vegetable oil, wax, paraffin, starch, tracant, a cellulose derivative, polyethylene glycol, silicon, bentonite, silica, talc, or zinc oxide.

When the formulation is powder or spray, an available carrier component may be, for example, lactose, talc, silica, aluminum hydroxide, calcium silicate, or polyamide powder, and in particular, in the case of spray, additionally, a propellent agent, such as chlorofluorohydrocarbone, propane/butane, or dimethyl ether, may be included.

When the formulation is a solution or an emulsion, an available carrier component may be, for example, a solvent, a solubilizing agent, or an emulsifying agent, and a detailed example thereof is water, ethanol, isopropanol, ethyl carbonate, ethyl acetate, benzyl alcohol, benzyl benzoate, propylene glycol, 1,3-butylglycol oil, glycerol aliphatic ester, polyethyle glycol, or fatty acid ester of sorbitan.

When the formulation is a suspension, an available carrier component may be, for example, a liquid diluent, such as water, ethanol, or propylene; a suspension, such as ethoxylated isostearyl alcohol, polyoxyethylene sorbitol ester, or polyoxyethylene sorbitan ester; microcrystalline cellulose, aluminium metahydroxide, bentonite, agar, or tracant.

Also, the health food may be provided in the form of powder, granule, tablet, capsule, syrup, or beverage, and the health food may include, in addition to the compound according to the present invention, which is an active ingredient, other foods or food additives, and these foods and additives may be appropriately used according to a conventional method. An amount of the active ingredient may be appropriately determined according to purpose, for example, prevention, health, or therapeutic treatment.

An effective amount of the compound included in the health food may vary according to an effective amount of the pharmaceutical composition. However, in the case of a long-term intake for health and sanitation or health control purpose, the amount of the compound may be smaller than the lower limit of the range. Also, the active ingredient is stable and accordingly, when used outside the upper limit of the range, stability is guaranteed.

The health food is not particularly limited, and examples thereof are meat, sausage, bread, chocolate, candies, snacks, biscuits, pizza, instant noodles, other noodles, gum, dairy products including ice cream, various soups, beverages, tea, drinks, alcoholic beverage, and vitamin composites.

Hereinafter, embodiments of the present invention are described in detail by referring to Examples below. However, the examples below are provided for illustrative purpose only and do not limit the scope of the present invention.

Example 1

Synthesis of Compounds 1 to 12

Table 1 below is provided to explain substitution patterns of Compounds 1 to 12, which are 2-(substituted phenyl)thiazolidine-4-carboxylic acid analog, synthesized in the following examples.

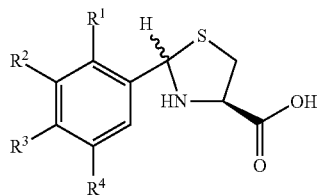

TABLE 1

| Compound | $R^1$ | $R^2$ | $R^3$ | $R^4$ |
|---|---|---|---|---|
| 1 | H | H | OH | H |
| 2 | H | OH | OH | H |
| 3 | OH | H | OH | H |
| 4 | H | OMe | OH | H |
| 5 | H | OEt | OH | H |
| 6 | H | OH | OMe | H |
| 7 | H | H | OMe | H |
| 8 | H | OMe | OMe | H |
| 9 | OMe | H | OMe | H |
| 10 | OH | H | H | H |
| 11 | H | OMe | OMe | OMe |
| 12 | H | OMe | OH | OMe |

OMe represents a methoxy group, and OEt represents an ethoxy group.

Synthesis of Compounds 1, 2, and 4 to 12 was performed as follows. In detail, in an ethanol (EtOH) (5 to 30 ml) solvent, a suspension of substituted benzaldhehyde (1.53 to 2.46 mmol) and L-cysteine (1.0 or 1.5 eq.) was refluxed for 1.5 to 48 hours. The produced precipitate was filtered, and in consideration of characteristics of the remaining starting materials, a filter cake was washed with ethanol, methylene chloride, water, ethyl acetate(ethyl acetate), and/or methanol (MeOH) to obtain a target product (yield: 9.9 to 78.6%). A synthesis method of Compound 3 was separately described below.

Example 1-1

Synthesis of (2R/S,4R)-2-(4-hydroxyphenyl)thiazolidine-4-carboxylic acid (Compound 1)

White solid; a reaction time of 13 hours; a yield of 50.0%; a melting point of 161.8 to 164.4° C., $^1$H NMR (400 MHz, DMSO-$d_6$) δ 9.48 (br s, 1H), 9.39 (br s, 1H), 7.27 (d, 2H, J=8.8 Hz), 7.20 (d, 2H, J=8.4 Hz), 6.70 (d, 2H, J=8.4 Hz), 6.66 (d, 2H, J=8.4 Hz), 5.49 (s, 1H), 5.36 (s, 1H), 4.21 (dd, 1H, J=4.4, 7.6 Hz), 3.79 (dd, 1H, J=7.6, 8.4 Hz), 3.30 (dd, 1H, J=7.2, 10.0 Hz), 3.23 (dd, 1H, J=7.2, 10.4 Hz), 3.11 (dd, 1H, J=4.4, 10.4 Hz), 3.00 (t, 1H, J=8.4, 10.0 Hz); $^{13}$C NMR (100 MHz, DMSO-$d_6$) δ 173.8, 173.0, 158.1, 157.6, 131.4, 129.5, 129.2, 129.0, 115.8, 115.6, 72.5, 72.0, 65.9, 65.4, 39.2, 38.5; LRMS (ESI) m/z 224 (M−H)$^−$.

Example 1-2

Synthesis of (2R/S,4R)-2-(3,4-dihydroxyphenyl)thiazolidine-4-carboxylic acid (Compound 2)

White solid; a reaction time of 12 hours; a yield of 77.3%; a melting point of 195.5 to 196.8° C.; $^1$H NMR (500 MHz, DMSO-$d_6$) δ 8.96 (br s, 2H), 8.89 (br s, 2H), 6.88 (d, 1H, J=1.5 Hz), 6.83 (s, 1H), 6.73 (dd, 1H, J=1.5, 8.0 Hz), 6.68 (d, 1H, J=8.0 Hz), 6.68 (d, 1H, J=8.0 Hz), 6.64 (d, 1H, J=2.5, 8.5 Hz), 5.46 (s, 1H), 5.32 (s, 1H), 4.21 (dd, 1H, J=4.0, 7.0 Hz), 3.82 (t, 1H, J=8.0 Hz), 3.33 (dd, 1H, J=7.0, 10.0 Hz), 3.23 (dd, 1H, J=7.0, 10.0 Hz), 3.11 (dd, 1H, J=4.0, 10.5 Hz), 2.94 (t, 1H, J=9.5 Hz); $^{13}$C NMR (100 MHz, DMSO-$d_6$) δ 173.8, 173.2, 146.1, 145.9, 145.6, 145.6, 132.1, 130.1, 118.9, 118.7, 116.0, 115.7, 115.2, 115.1, 72.7, 72.1, 65.9, 65.4, 39.3, 38.4; LRMS (ES) m/z 240 (M−H)$^−$.

Example 1-3

Synthesis of (2R/S,4R)-2-(2,4-dihydroxyphenyl)thiazolidine-4-carboxylic acid (Compound 3)

In a mixed solvent including ethanol (10 ml) and water (10 ml), a solution including 2,4-dihydroxybenzaldehyde (943 mg, 6.83 mmol), L-cysteine hydrochloride monohydrate (1.0 g, 5.69 mmol), and sodium acetate (495 mg, 6.03 mmol) was stirred at room temperature for 14 hours. The produced precipitate was filtered, and a filter cake was washed with water, and ethyl acetate to obtain the target product that is a solid white (1.316 g, 95.8%).

White solid; a reaction time of 14 hours; a yield of 95.8%; a melting point of >300° C.; $^1$H NMR (500 MHz, DMSO-$d_6$) δ 9.30 (br s, 2H), 9.19 (br s, 2H), 7.11 (d, 1H, J=8.0 Hz), 7.08 (d, 1H, J=8.5 Hz), 6.27 (d, 1H, J=2.5 Hz), 6.24 (d, 1H, J=2.0 Hz), 6.20 (dd, 1H, J=2.5, 8.5 Hz), 6.18 (dd, 1H, J=2.5, 8.0 Hz), 5.74 (s, 1H), 5.57 (s, 1H), 4.23 (dd, 1H, J=4.5, 7.0 Hz), 3.77 (dd, 1H, J=7.0, 8.5 Hz), 3.31 (dd, 1H, J=7.5, 10.0 Hz), 3.20 (dd, 1H, J=7.0, 10.0 Hz), 3.07 (dd, 1H, J=4.0, 10.0 Hz), 2.94 (t, 1H, J=9.0 Hz); $^{13}$C NMR (100 MHz, DMSO-$d_6$) δ 173.7, 173.2, 158.8, 158.3, 156.9, 156.3, 129.5, 128.2, 117.9, 115.2, 107.1, 106.8, 103.4, 103.0, 68.6, 66.5, 65.6, 65.2, 38.9, 37.6; LRMS (ES) m/z 240 (M−H)$^−$.

Example 1-4

Synthesis of (2R/S,4R)-2-(4-hydroxy-3-methoxyphenyl)thiazolidine-4-carboxylic acid (Compound 4)

White solid; a reaction time of 48 hours; a yield of 42.7%; a melting point of 166.6-168.4° C.; $^1$H NMR (500 MHz, DMSO-d₆) δ 9.05 (br s, 1H), 8.97 (br s, 1H), 7.10 (d, 1H, J=1.5 Hz), 7.01 (d, 1H, J=2.0 Hz), 6.88 (dd, 1H, J=2.0, 8.0 Hz), 6.83 (dd, 1H, J=1.5, 8.0 Hz), 6.72 (d, 1H, J=8.0 Hz), 6.69 (d, 1H, J=8.0 Hz), 5.52 (s, 1H), 5.39 (s, 1H), 4.27 (dd, 1H, J=4.0, 7.5 Hz), 3.83 (dd, 1H, J=7.5, 8.5 Hz), 3.76 (s, 3H), 3.75 (s, 3H), 3.32 (dd, 1H, J=6.5, 9.5 Hz), 3.27 (dd, 1H, J=7.5, 10.5 Hz), 3.15 (dd, 1H, J=3.5, 10.5 Hz), 3.05 (dd, 1H, J=9.5 Hz); $^{13}$C NMR (100 MHz, DMSO-d₆) δ 173.8, 172.9, 148.2, 148.0, 147.3, 146.8, 132.0, 130.2, 120.6, 120.3, 115.8, 115.7, 112.2, 112.0, 72.8, 72.2, 66.1, 65.4, 56.4, 56.3, 39.1, 38.4; LRMS (ES) m/z 254 (M−H)⁻.

Example 1-5

Synthesis of (2R/S,4R)-2-(3-ethoxy-4-hydroxyphenyl)thiazolidine-4-carboxylic acid (Compound 5)

White solid; a reaction time of 3 hours; a yield of 77.7%; a melting point of 174.3-175.9° C.; $^1$H NMR (400 MHz, DMSO-d₆) δ 8.90 (s, 2H), 7.06 (d, 1H, J=2.0 Hz), 6.97 (d, 1H, J=2.0 Hz), 6.84 (dd, 1H, J=2.0, 8.0 Hz), 6.79 (dd, 1H, J=2.4, 8.4 Hz), 6.70 (d, 1H, J=8.0 Hz), 6.67 (d, 1H, J=8.0 Hz), 5.47 (s, 1H), 5.34 (s, 1H), 4.23 (dd, 1H, J=3.6, 7.2 Hz), 3.99-3.94 (m, 4H), 3.79 (dd, 1H, J=7.2, 8.8 Hz), 3.32 (dd, 1H, J=7.2, 10.4 Hz), 3.23 (dd, 1H, J=7.2, 10.0 Hz), 3.12 (dd, 1H, J=3.6, 10.0 Hz), 3.01 (t, 1H, J=9.6 Hz), 1.28 (t, 3H, J=7.2 Hz), 1.28 (t, 3H, J=6.8 Hz); $^{13}$C NMR (100 MHz, DMSO-d₆) δ 173.8, 172.9, 147.6, 147.3, 147.1, 147.1, 131.9, 130.1, 120.7, 120.4, 115.9, 115.7, 113.5, 113.3, 72.8, 72.2, 66.1, 65.4, 64.6, 64.6, 39.0, 38.4, 15.4, 15.4; LRMS (ES) m/z 268 (M−H)⁻.

Example 1-6

Synthesis of (2R/S,4R)-2-(3-hydroxy-4-methoxyphenyl)thiazolidine-4-carboxylic acid (Compound 6)

White solid; a reaction time of 8 hours; a yield of 78.6%; a melting point of 146.9-149.8° C.; $^1$H NMR (500 MHz, DMSO-d₆) δ 9.05 (br s, 1H), 8.96 (br s, 1H), 6.92 (s, 1H), 6.87 (m, 3H), 6.83 (d, 1H, J=8.0 Hz), 6.80 (d, 1H, J=8.0 Hz), 5.51 (s, 1H), 5.36 (s, 1H), 4.20 (dd, 1H, J=4.5, 6.5 Hz), 3.83 (dd, 1H, J=7.5, 8.5 Hz), 3.75 (s, 3H), 3.73 (s, 3H), 3.33 (dd, 1H, J=7.5, 9.5 Hz), 3.25 (dd, 1H, J=7.5, 10.0 Hz), 3.10 (dd, 1H, J=4.0, 10.0 Hz), 3.02 (t, 1H, J=9.5 Hz); $^{13}$C NMR (100 MHz, DMSO-d₆) δ 173.8, 173.1, 148.3, 147.8, 147.1, 146.9, 134.0, 131.8, 118.8, 118.4, 115.0, 115.0, 112.6, 112.4, 72.5, 71.8, 65.9, 65.5, 56.3, 56.3, 39.2, 38.5; LRMS (ES) m/z 254 (M−H)⁻.

Example 1-7

Synthesis of (2R/S,4R)-2-(4-methoxyphenyl)thiazolidine-4-carboxylic acid (Compound 7)

White solid; a reaction time of 48 hours; a yield of 40.5%; a melting point of 157.6-158.2° C.; $^1$H NMR (500 MHz, II) δ 7.43 (d, 2H, J=8.5 Hz), 7.35 (d, 2H, J=8.5 Hz), 6.91 (d, 2H, J=8.5 Hz), 6.87 (d, 2H, J=9.0 Hz), 5.58 (s, 1H), 5.44 (s, 1H), 4.23 (dd, 1H, J=4.0, 7.5 Hz), 3.85 (dd, 1H, J=2.0, 8.5 Hz), 3.74 (s, 3H), 3.73 (s, 3H), 3.34 (dd, 1H, J=7.0, 10.0 Hz), 3.27 (dd, 1H, J=7.0, 10.0 Hz), 3.14 (dd, 1H, J=4.0, 10.0 Hz), 3.05 (dd, 1H, J=8.5, 10.0 Hz); $^{13}$C NMR (100 MHz, DMSO-d₆) δ 173.8, 172.9, 159.9, 159.4, 133.4, 131.4, 129.3, 129.0, 114.5, 114.2, 72.2, 71.6, 66.0, 65.5, 55.8, 55.8, 39.2, 38.5; LRMS (ES) m/z 238 (M−H)⁻.

Example 1-8

Synthesis of (2R/S,4R)-2-(3,4-dimethoxyphenyl)thiazolidine-4-carboxylic acid (Compound 8)

White solid; a reaction time of 10 hours; a yield of 57.0%; a melting point of 173.6-175.4° C.; $^1$H NMR (500 MHz, DMSO-d₆) δ 7.15 (d, 1H, J=2.0 Hz), 7.04 (d, 1H, J=2.0 Hz), 7.01 (dd, 1H, J=2.0, 8.0 Hz), 6.96 (dd, 1H, J=2.0, 8.0 Hz), 6.90 (d, 1H, J=8.0 Hz), 6.87 (d, 1H, J=8.5 Hz), 5.57 (s, 1H), 5.43 (s, 1H), 4.28 (dd, 1H, J=4.0, 7.5 Hz), 3.85 (dd, 1H, J=7.0, 9.0 Hz), 3.75 (s, 3H), 3.74 (s, 3H), 3.74 (s, 3H), 3.72 (s, 3H), 3.33 (dd, 1H, J=7.0, 10.0 Hz), 3.28 (dd, 1H, J=7.5, 10.5 Hz), 3.16 (dd, 1H, J=4.0, 10.5 Hz), 3.06 (t, 1H, J=9.5 Hz); $^{13}$C NMR (100 MHz, DMSO-d₆) δ 173.8, 172.9, 149.4, 149.3, 149.2, 149.0, 133.6, 131.8, 120.3, 119.9, 112.1, 112.0, 111.7, 111.5, 72.6, 72.0, 66.2, 65.5, 56.2, 56.1, 39.0, 38.5; LRMS (ES) m/z 268 (M−H)⁻.

Example 1-9

Synthesis of (2R/S,4R)-2-(2,4-dimethoxyphenyl)thiazolidine-4-carboxylic acid (Compound 9)

White solid; a reaction time of 1.5 hours; a yield of 34.7%; a melting point of 137.7-139.2° C.; $^1$H NMR (500 MHz, DMSO-d₆) δ 7.39 (d, 1H, J=8.5 Hz), 7.29 (d, 1H, J=8.0 Hz), 6.56 (d, 1H, J=1.5 Hz), 6.53 (dd, 1H, J=1.5, 8.5 Hz), 6.52 (d, 1H, J=1.5 Hz), 6.48 (dd, 1H, J=1.5, 8.5 Hz), 5.78 (s, 1H), 5.62 (s, 1H), 4.18 (t, 1H, J=6.0 Hz), 3.79 (dd, 1H, J=7.5, 8.5 Hz), 3.78 (s, 3H), 3.77 (s, 3H), 3.75 (s, 3H), 3.74 (s, 3H), 3.31 (dd, 1H, J=7.0, 10.0 Hz), 3.17 (dd, 1H, J=7.0, 10.0 Hz), 2.99 (dd, 1H, J=5.0, 10.0 Hz), 2.95 (t, 1H, J=9.0 Hz); $^{13}$C NMR (100 MHz, DMSO-d₆) δ 173.7, 173.1, 161.1, 160.5, 158.4, 157.9, 129.0, 127.1, 122.6, 119.3, 105.7, 105.2, 99.3, 99.0, 67.2, 66.0, 65.7, 65.6, 56.3, 56.2, 55.9, 55.9, 39.0, 37.9; LRMS (ES) m/z 268 (M−H)⁻.

Example 1-10

Synthesis of (2R/S,4R)-2-(2-hydroxyphenyl)thiazolidine-4-carboxylic acid (Compound 10)

White solid; a reaction time of 6 hours; a yield of 75.0%; a melting point of 173.2-175.1° C.; $^1$H NMR (500 MHz, DMSO-d₆) δ 9.90 (br s, 2H), 7.33 (dd, 1H, J=1.0, 8.0 Hz), 7.28 (d, 1H, J=7.5 Hz), 7.12 (td, 1H, J=1.5, 8.0 Hz), 7.05 (td, 1H, J=1.5, 8.0 Hz), 6.81-6.73 (m, 4H), 5.83 (s, 1H), 5.64 (s, 1H), 4.20 (dd, 1H, J=5.5, 6.5 Hz), 3.82 (dd, 1H, J=7.0, 9.0 Hz), 3.33 (dd, 1H, J=7.0, 10.0 Hz), 3.19 (dd, 1H, J=7.0, 10.5 Hz), 3.01 (dd, 1H, J=5.0, 10.0 Hz), 2.96 (t, 1H, J=10.0 Hz); $^{13}$C NMR (100 MHz, DMSO-d₆) 173.6, 173.1, 155.8, 155.3, 129.7, 128.8, 128.5, 126.7, 120.1, 119.7, 119.4, 117.9, 116.3, 115.7, 68.3, 66.3, 65.9, 65.5, 38.9, 37.7; LRMS (ES) m/z 224 (M−H)⁻.

Example 1-11

Synthesis of (2R/S,4R)-2-(3,4,5-trimethoxyphenyl)thiazolidine-4-carboxylic acid (Compound 11)

White solid; a reaction time of 5 hours; a yield of 9.9%; a melting point of 197.0-199.7° C.; $^1$H NMR (500 MHz, DMSO-d₆) δ 6.85 (s, 2H), 6.76 (s, 2H), 5.57 (s, 1H), 5.42 (s, 1H), 4.28 (dd, 1H, J=4.0, 7.0 Hz), 3.85 (dd, 1H, J=6.5, 8.5 Hz), 3.77 (s, 6H), 3.76 (s, 6H), 3.64 (s, 3H), 3.63 (s, 3H), 3.32 (dd, 1H, J=6.5, 9.5 Hz), 3.29 (dd, 1H, J=7.0, 10.0 Hz), 3.15

(dd, 1H, J=4.0, 10.5 Hz), 3.07 (t, 1H, J=9.5 Hz); $^{13}$C NMR (100 MHz, DMSO-$d_6$) δ 173.8, 172.8, 153.4, 153.3, 137.9, 137.5, 137.1, 135.3, 105.5, 105.0, 72.8, 72.1, 66.4, 65.5, 60.6, 60.6, 56.6, 56.5, 38.9, 38.5; LRMS (ES) m/z 298 (M−H)$^−$.

Example 1-12

Synthesis of (2R/S,4R)-2-(4-hydroxy-3,5-dimethoxyphenyl)thiazolidine-4-carboxylic acid (Compound 12)

White solid; a reaction time of 4 hours; a yield of 69.7%; a melting point of 139.6-141.0° C.; $^1$H NMR (500 MHz, DMSO-$d_6$) δ 8.42 (br s, 2H), 6.79 (s, 2H), 6.72 (s, 2H), 5.52 (s, 1H), 5.39 (s, 1H), 4.30 (dd, 1H, J=3.5, 7.5 Hz), 3.83 (t, 1H, J=8.0 Hz), 3.75 (s, 6H), 3.74 (s, 6H), 3.32 (dd, 1H, J=7.0, 9.5 Hz), 3.28 (dd, 1H, J=7.5, 10.5 Hz), 3.17 (dd, 1H, J=3.5, 10.5 Hz), 3.06 (t, 1H, J=9.5 Hz); $^{13}$C NMR (100 MHz, DMSO-$d_6$) δ 173.9, 172.9, 148.4, 148.3, 136.2, 135.7, 131.0, 129.3, 105.7, 105.3, 73.1, 72.5, 66.2, 65.5, 56.7, 56.7, 39.0, 38.4; LRMS (ES) m/z 284 (M−H)$^−$.

Example 2

Synthesis of Compounds 13 to 27

Table 2 below is provided to explain substitution patterns of Compounds 13 to 27, which are 2-(substituted phenyl)benzo[d]thiazole analogs.

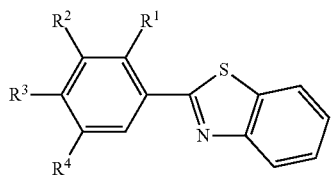

TABLE 2

| Compound | R$^1$ | R$^2$ | R$^3$ | R$^4$ |
|---|---|---|---|---|
| 13 | H | H | OH | H |
| 14 | H | OH | OH | H |
| 15 | OH | H | OH | H |
| 16 | H | OMe | OH | H |
| 17 | H | OEt | OH | H |
| 18 | H | OH | OMe | H |
| 19 | H | H | OMe | H |
| 20 | H | OMe | OMe | H |
| 21 | H | OH | H | OH |
| 22 | OMe | H | OMe | H |
| 23 | OH | H | H | H |
| 24 | H | OMe | OMe | OMe |
| 25 | H | OMe | OH | OMe |
| 26 | H | Br | OH | H |
| 27 | H | Br | OH | Br |

OMe represents a methoxy group, and OEt represents an ethoxy group.

Synthesis of Compounds 13, 20, and 22 to 25 was performed as follows. In a methanol (3 to 7 mL) solvent, 2-aminothiophenol (1.60 mmol) was added to a suspension of substituted benzaldehyde (1.33 mmol), and the reaction mixture was stirred at room temperature for 5 to 96 hours. The work-up of the reaction was performed by using one of the following three methods A through C.

Method A: methanol was evaporated, and then, the resultant solid was filtered and a filter cake was washed with hexane, methylene chloride, ethyl acetate, and/or cold methanol.

Method B: methanol was evaporated, and then, the residual was dissolved in small amounts of methylene chloride, ethyl acetate and/or cold methanol, and then, hexane was added thereto. After cooling, the resultant precipitate was filtered, and the filtered product was washed with hexane, methylene chloride, ethyl acetate and/or cold methanol.

Method C: methanol was evaporated until its volume reduced in half thereof, and then, the reaction mixture was preserved in a cooler or, before the preservation in the cooler, water (20 mL) was added to the reaction mixture. The resultant precipitate was filtered, and a filter cake was washed with hexane, methylene chloride, ethyl acetate and/or cold methanol.

In the case of several compounds (Compounds 23 and 25), flash column chromatography (hexane/methylene chloride=4/1 to 2/1, Compound 23; methylene chloride/methanol=90/1, and then, methylene chloride, Compound 25) was performed thereon for purification. The target products (Compounds 13-20, and 22-24) were obtained in a yield of 15.2 to 82.6%

However, synthesis methods of Compounds 21, 26 and 27, which are different from the method described above, are separately described below.

Example 2-1

Synthesis of 4-(benzo[d]thiazol-2-yl)phenol (Compound 13)

Light yellow solid; a reaction time of 22 h; a yield of 28.5%; a melting point of 228.0-229.3° C.; $^1$H NMR (400 MHz, CD$_3$OD) δ 7.94-7.92 (m, 4H), 7.49 (td, 1H, J=1.0, 7.6 Hz), 7.38 (td, 1H, J=1.0, 7.6 Hz), 6.91 (d, 2H, J=8.0 Hz); $^{13}$C NMR (100 MHz, CD$_3$OD) δ169.2, 160.8, 153.8, 134.5, 129.1, 126.3, 124.9, 124.8, 121.9, 121.6, 115.8; LRMS (ESI) m/z 228 (M+H)$^+$.

Example 2-2

Synthesis of 4-(benzo[d]thiazol-2-yl)benzene-1,2-diol (Compound 14)

Bright Yellowish green solid; a reaction time of 96 hours; a yield of 61.5%; a melting point of 219.2-219.9° C.; $^1$H NMR (400 MHz, CD$_3$OD) δ 7.90-7.87 (m, 2H), 7.50 (d, 1H, J=2.4 Hz), 7.44 (td, 1H, J=1.2, 8.4 Hz), 7.40 (dd, 1H, J=2.4, 8.0 Hz), 7.33 (td, 1H, J=1.2, 8.4 Hz), 6.86 (d, 1H, J=8.0 Hz); $^{13}$C NMR (100 MHz, CD$_3$OD) δ 169.4, 153.8, 149.1, 145.8, 134.5, 126.3, 125.1, 124.9, 121.9, 121.5, 120.0, 115.5, 114.0; LRMS (ESI) m/z 244 (M+H)$^+$.

Example 2-3

Synthesis of 4-(benzo[d]thiazol-2-yl)benzene-1,3-diol (Compound 15)

White solid; a reaction time of 20 hours; a yield of 15.2%; a melting point of 197.7-198.5° C.; $^1$H NMR (400 MHz, CD$_3$OD) δ 7.90 (ddd, 1H, J=0.8, 1.2, 8.0 Hz), 7.87 (ddd, 1H, J=0.8, 1.2, 8.0 Hz), 7.58 (dd, 1H, J=0.4, 8.4 Hz), 7.46 (td, 1H, J=1.2, 7.2 Hz), 7.35 (td, 1H, J=1.2, 7.2 Hz), 6.41 (dd, 1H, J=2.4, 8.4 Hz), 6.39 (d, 1H, J=2.4 Hz); $^{13}$C NMR (100 MHz, CD₃OD) δ 169.5, 162.2, 159.7, 151.8, 132.3, 129.9, 126.5, 125.0, 121.4, 121.1, 109.5, 108.2, 102.8; LRMS (ESI) m/z 244 (M+H)⁺.

Example 2-4

Synthesis of 4-(benzo[d]thiazol-2-yl)-2-methoxyphenol (Compound 16)

Green solid; a reaction time of 22 hours; a yield of 55.6%; a melting point of 171.4-173.6° C.; $^1$H NMR (400 MHz, CD₃OD) δ 7.93-7.91 (m, 2H), 7.67 (d, 1H, J=2.4 Hz), 7.49 (dd, 1H, J=2.0, 8.4 Hz), 7.47 (td, 1H, J=1.2, 7.6 Hz), 7.36 (td, 1H, J=1.2, 7.6 Hz), 6.89 (d, 1H, J=8.0 Hz), 3.95 (s, 3H); $^{13}$C NMR (100 MHz, CD₃OD) δ 169.3, 153.7, 150.2, 148.4, 134.5, 126.4, 125.0, 125.0, 121.9, 121.6, 121.5, 115.5, 109.9, 55.3; LRMS (ESI) m/z 258 (M+H)⁺.

Example 2-5

Synthesis of 4-(benzo[d]thiazol-2-yl)-2-ethoxyphenol (Compound 17)

Light gray solid; a reaction time of 20 hours; a yield of 36.2%; a melting point of 125.6-126.5° C.; $^1$H NMR (500 MHz, CD₃OD) δ 7.92 (d, 1H, J=8.5 Hz), 7.91 (d, 1H, J=8.0 Hz), 7.65 (d, 1H, J=1.5 Hz), 7.49-7.46 (m, 2H), 7.36 (td, 1H, J=1.0, 8.0 Hz), 6.90 (d, 1H, J=8.0 Hz), 4.19 (q, 2H, J=7.0 Hz), 1.47 (t, 3H, J=7.0 Hz); $^{13}$C NMR (100 MHz, CD₃OD) δ 168.5, 152.9, 149.5, 146.6, 133.7, 125.5, 124.3, 124.1, 121.1, 120.7, 120.7, 114.8, 110.4, 63.8, 13.0; LRMS (ESI) m/z 272 (M+H)⁺.

Example 2-6

Synthesis of 5-(benzo[d]thiazol-2-yl)-2-methoxyphenol (Compound 18)

Light gray solid; a reaction time of 20 hours; a yield of 39.3%; a melting point of 171.6-172.2° C.; $^1$H NMR (400 MHz, CD₃OD) δ 7.94-7.92 (m, 2H), 7.53 (dd, 1H, J=2.0, 8.0 Hz), 7.52 (d, 1H, J=2.0 Hz), 7.47 (td, 1H, J=1.2, 8.4 Hz), 7.37 (td, 1H, J=1.2, 8.4 Hz), 7.04 (d, 1H, J=8.4 Hz), 3.91 (s, 3H); $^{13}$C NMR (100 MHz, CD₃OD) δ 169.0, 153.8, 150.9, 147.1, 134.6, 126.4, 125.1, 125.1, 122.1, 121.6, 119.6, 113.7, 111.5, 55.3; LRMS (ESI) m/z 258 (M+H)⁺.

Example 2-7

Synthesis of 2-(4-methoxyphenyl)benzo[d]thiazole (Compound 19)

White solid; a reaction time of 5 hours; a yield of 15.8%; a melting point of 121.3-121.9° C.; $^1$H NMR (500 MHz, CDCl₃) δ 8.06-8.04 (m, 3H), 7.87 (d, 1H, J=8.0 Hz), 7.48 (td, 1H, J=1.0, 8.0 Hz), 7.36 (td, 1H, J=1.0, 7.5 Hz), 7.00 (d, 2H, J=9.0 Hz), 3.88 (s, 3H); $^{13}$C NMR (100 MHz, CDCl₃) δ 168.2, 162.2, 154.2, 135.0, 129.4, 126.5, 125.1, 125.1, 123.0, 121.7, 114.6, 55.7; LRMS (ESI) m/z 242 (M+H)⁺.

Example 2-8

Synthesis of 2-(3,4-dimethoxyphenyl)benzo[d]thiazole (Compound 20)

White solid; a reaction time of 22 hours; a yield of 27.9%; a melting point of 135.0-137.2° C.; $^1$H NMR (400 MHz, CDCl₃) δ 8.03 (d, 1H, J=8.0 Hz), 7.85 (d, 1H, J=8.0 Hz), 7.71 (d, 1H, J=1.6 Hz), 7.57 (dd, 1H, J=2.0, 8.4 Hz), 7.45 (t, 1H, J=7.6 Hz), 7.34 (t, 1H, J=7.6 Hz), 6.91 (d, 1H, J=8.4 Hz), 4.00 (s, 3H), 3.93 (s, 3H); $^{13}$C NMR (100 MHz, CDCl₃) δ 168.2, 154.1, 151.9, 149.6, 134.9, 126.7, 1266.5, 125.2, 123.0, 121.7, 121.4, 111.2, 110.0, 56.4, 56.3; LRMS (ESI) m/z 272 (M+H)⁺.

Example 2-9

Synthesis of 5-(benzo[d]thiazol-2-yl)benzene-1,3-diol (Compound 21)

An acetic acid (0.8 mL) and sodium acetate (196.6 mg, 2.40 mmol) were added to a suspension including 3,5-dihydroxybenzaldehyde (91.6 mg, 0.66 mmol) and 2-aminothiophenol (0.095 mL, 0.80 mmol, purity: 90%), and then, the reaction mixture was refluxed for 2 hours. The resultant precipitate was filtered, and the filtered product was washed with water and methylene chloride to obtain a gray solid Compound 21 (78.3 mg, 48.6%).

Gray solid; a reaction time of 2 hours; a yield of 48.6%; a melting point of 274.5-276.5° C.; $^1$H NMR (400 MHz, CD₃OD) δ 7.94 (d, 1H, J=8.4 Hz), 7.92 (d, 1H, J=8.4 Hz), 7.47 (t, 1H, J=7.6 Hz), 7.37 (t, 1H, J=7.6 Hz), 6.98 (s, 2H), 6.42 (s, 1H); $^{13}$C NMR (100 MHz, CD₃OD) δ 169.2, 159.2, 153.6, 134.9, 134.7, 126.4, 125.4, 122.4, 121.7, 105.7, 105.4; LRMS (ESI) m/z 244 (M+H)⁺.

Example 2-10

Synthesis of 2-(2,4-dimethoxyphenyl)benzo[d]thiazole (Compound 22)

Very light yellow solid; a reaction time of 22 hours; a yield of 35.8%; a melting point of 137.4-138.9° C.; $^1$H NMR (500 MHz, CDCl₃) δ 8.50 (d, 1H, J=8.5 Hz), 8.07 (d, 1H, J=8.0 Hz), 7.90 (d, 1H, J=7.5 Hz), 7.48 (t, 1H, J=7.0 Hz), 7.35 (t, 1H, J=7.0 Hz), 6.69 (d, 1H, J=8.5 Hz), 6.59 (s, 1H), 4.04 (s, 3H), 3.90 (s, 3H); $^{13}$C NMR (100 MHz, CDCl₃) δ 163.6, 163.3, 158.9, 151.9, 135.6, 131.1, 126.1, 124.5, 122.4, 121.3, 115.6, 106.2, 98.7, 55.9, 55.8; LRMS (ESI) m/z 272 (M+H)⁺.

Example 2-11

Synthesis of 2-(benzo[d]thiazol-2-yl)phenol (Compound 23)

White solid; a reaction time of 21 hours; a yield of 42.9%; a melting point of 132.6-133.5° C.; $^1$H NMR (400 MHz, CDCl₃) δ 12.26 (s, 1H), 7.97 (ddd, 1H, J=0.4, 1.2, 8.0 Hz), 7.89 (ddd, 1H, J=0.8, 1.2, 8.0 Hz), 7.68 (dd, 1H, J=1.6, 7.6 Hz), 7.49 (ddd, 1H, J=1.2, 7.2, 8.4 Hz), 7.41-7.35 (m, 2H), 7.09 (dd, 1H, J=0.8, 8.4 Hz), 6.94 (ddd, 1H, J=1.2, 7.6, 8.0 Hz); $^{13}$C NMR (100 MHz, CDCl₃) δ 169.6, 158.2, 152.1, 133.0, 132.8, 128.6, 126.9, 125.8, 122.4, 121.7, 119.7, 118.8, 117.0; LRMS (ESI) m/z 228 (M+H)⁺.

Example 2-12

Synthesis of 2-(3,4,5-trimethoxyphenyl)benzo[d]thiazole (Compound 24)

White solid; a reaction time of 21 hours; a yield of 28.3%; a melting point of 149.5-151.1° C.; $^1$H NMR (400 MHz, CDCl$_3$) δ 8.04 (d, 1H, J=8.4 Hz), 7.87 (d, 1H, J=8.0 Hz), 7.47 (td, 1H, J=1.2, 7.2 Hz), 7.36 (td, 1H, J=1.2, 8.4 Hz), 7.31 (s, 2H), 3.97 (s, 6H), 3.91 (s, 3H); $^{13}$C NMR (100 MHz, CDCl$_3$) δ 168.0, 154.2, 153.8, 135.2, 129.3, 126.6, 125.3, 123.3, 123.3, 121.8, 105.0, 61.2, 56.6; LRMS (ESI) m/z 302 (M+H)⁺.

Example 2-13

Synthesis of 4-(benzo[d]thiazol-2-yl)-2,6-dimethoxyphenol (Compound 25)

Bright brown solid; a reaction time of 16 hours; a yield of 82.6%; a melting point of 153.5-156.1° C.; $^1$H NMR (400 MHz, CDCl$_3$) δ 8.00 (dd, 1H, J=0.8, 8.0 Hz), 7.81 (dd, 1H, J=0.4, 7.6 Hz), 7.42 (td, 1H, J=1.2, 7.2 Hz), 7.30 (td, 1H, J=1.2, 7.6 Hz), 7.29 (s, 2H), 6.47 (br s, 1H), 3.89 (s, 6H); $^{13}$C NMR (100 MHz, CDCl$_3$) δ 168.4, 154.2, 147.6, 138.1, 134.9, 126.5, 125.1, 125.1, 123.0, 121.7, 104.8, 56.6; LRMS (ESI) m/z 288 (M+H)⁺.

Example 2-14

Synthesis of 4-(benzo[d]thiazol-2-yl)-2-bromophenol (Compound 26)

In a methanol solvent, a solution including 2-aminothiophenol (1.0 eq.) and 3-bromo-4-hydroxybenzaldehyde (1.0 eq.) was stirred at room temperature. The produced precipitate was filtered and the filtered product was washed with cold methanol to obtain Compound 26.

Light Lemon-colored solid; a reaction time of 19 hours; a yield of 38.0%; a melting point of 190.6-191.7° C.; $^1$H NMR (500 MHz, DMSO-d$_6$) δ 11.09 (s, 1H), 8.18 (d, 1H, J=1.5 Hz), 8.08 (d, 1H, J=8.0 Hz), 7.99 (d, 1H, J=8.0 Hz), 7.89 (dd, 1H, J=2.0, 8.5 Hz), 7.50 (t, 1H, J=7.5 Hz), 7.41 (t, 1H, J=7.5 Hz), 7.10 (d, 1H, J=8.5 Hz); $^{13}$C NMR (100 MHz, DMSO-d$_6$) δ 166.5, 157.7, 154.2, 134.9, 132.0, 128.9, 127.3, 126.1, 125.9, 123.2, 122.9, 117.5, 110.8.

Example 2-15

Synthesis of 4-(benzo[d]thiazol-2-yl)-2,6-dibromophenol (Compound 27)

In a methanol solvent, a solution including 2-aminothiophenol (1.0 eq.) and 3,5-dibromo-4-hydroxybenzaldehyde (1.0 eq.) was stirred at room temperature. The produced precipitate was filtered and the filtered product was washed with cold methanol to obtain Compound 27.

A reaction time of 7 hours; a yield of 16.0%; $^1$H NMR (500 MHz, DMSO-d$_6$) δ 10.76 (s, 1H), 8.17 (s, 2H), 8.12 (d, 1H, J=8.0 Hz), 8.01 (d, 1H, J=8.0 Hz), 7.53 (t, 1H, J=8.0 Hz), 7.44 (t, 1H, J=8.0 Hz) $^{13}$C NMR (100 MHz, DMSO-d$_6$) δ 164.9, 154.1, 154.0, 135.2, 131.4, 127.7, 127.4, 126.2, 123.5, 123.0, 113.1.

Example 3

Synthesis of Compounds 28 to 42

Table 3 below is provided to explain substitution patterns of Compounds 28 to 42, which are 2-(substituted phenyl)-5-(trifluoromethyl)benzo[d]thiazole analogs.

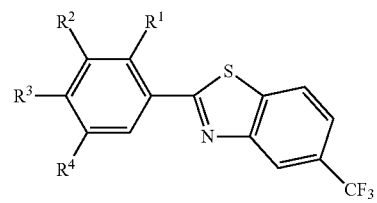

TABLE 3

| Compound | R$^1$ | R$^2$ | R$^3$ | R$^4$ |
|---|---|---|---|---|
| 28 | H | H | OH | H |
| 29 | H | OH | OH | H |
| 30 | OH | H | OH | H |
| 31 | H | OMe | OH | H |
| 32 | H | OEt | OH | H |
| 33 | H | OH | OMe | H |
| 34 | H | H | OMe | H |
| 35 | H | OMe | OMe | H |
| 36 | H | OH | H | OH |
| 37 | OMe | H | OMe | H |
| 38 | OH | H | H | H |
| 39 | H | OMe | OMe | OMe |
| 40 | H | OMe | OH | OMe |
| 41 | H | Br | OH | H |
| 42 | H | Br | OH | Br |

OMe represents a methoxy group, and OEt represents an ethoxy group.

Synthesis methods of Compounds 28 to 35 and 37 to 40 are as follows. In detail, in a methyl alcohol (5 mL) solvent, a mixture of 2-amino-4-(trifluoromethyl)benzenethiol (100 mg, 0.44 mmol) and substituted benzaldhehyde (0.8 to 1.0 eq.) was stirred at room temperature for 4 to 15 hours. After the solvent was evaporated, the residual was solidified by using methyl alcohol and/or methylene chloride and/or water, and then, the result was preserved at a temperature of 0° C. The produced precipitate was filtered, and in consideration of physical characteristics of the remaining starting materials, the filtered product was washed with iced water and/or methylene chloride and/or cold methyl alcohol to obtain a solid target product. In the case of Compound 30, after the reaction solvent was removed, the residual was purified by silica gel column chromatography using hexane and ethyl acetate (4:1) as a developer to obtain a solid Compound 30.

However, synthesis methods of Compounds 36, 41 and 42, which are different from the method described above, are separately described below.

Example 3-1

Synthesis of 4-(5-(trifluoromethyl)benzo[d]thiazol-2-yl)phenol (Compound 28)

White solid; a reaction time of 5.5 hours; a yield of 58.1%; a melting point of 187.2-188.9° C.; $^1$H NMR (500 MHz, CD$_3$OD) δ 8.18 (d, 1H, J=1.0 Hz), 8.11 (d, 1H, J=8.5 Hz), 7.95 (d, 2H, J=8.5 Hz), 7.62 (dd, 1H, J=1.0, 9.0 Hz), 6.92 (d, 2H, J=8.5 Hz); $^{13}$C NMR (100 MHz, CD$_3$OD) δ 171.4, 161.4, 153.7, 138.5, 129.4, 128.7 (q, J=31.8 Hz), 124.5 (q, J=269.3 Hz), 124.2, 122.7, 120.9 (q, J=3.8 Hz), 118.8 (q, J=4.5 Hz), 115.9; $^{19}$F NMR (470 MHz, CD$_3$OD) δ −63.66.

Example 3-2

Synthesis of 4-(5-(trifluoromethyl)benzo[d]thiazol-2-yl)benzene-1,2-diol (Compound 29)

Gray solid; a reaction time of 7.5 hours; a yield of 64.3%; a melting point of 267.3-269.4° C.; $^1$H NMR (500 MHz, CD$_3$OD) δ 8.14 (s, 1H), 8.07 (d, 1H, J=8.5 Hz), 7.59 (dd, 1H, J=1.0, 8.5 Hz), 7.53 (d, 1H, J=2.5 Hz), 7.42 (dd, 1H, J=2.5, 8.0 Hz), 6.88 (d, 1H, J=8.0 Hz); $^{13}$C NMR (100 MHz, CD$_3$OD) δ 171.7, 153.2, 149.7, 145.9, 138.3, 128.8 (q, J=32.7 Hz), 124.5 (q, J=270.0 Hz), 124.4, 122.7, 120.9 (q, J=3.8 Hz), 120.4, 118.6 (q, J=3.8 Hz), 115.6, 114.1; $^{19}$F NMR (470 MHz, CD$_3$OD) δ −63.64.

Example 3-3

Synthesis of 4-(5-(trifluoromethyl)benzo[d]thiazol-2-yl)benzene-1,3-diol (Compound 30)

White solid; a reaction time of 7 hours; a yield of 50.2%; a melting point of 236.2-238.2° C.; $^1$H NMR (400 MHz, CD$_3$OD) δ 8.16 (s, 1H), 8.10 (d, 1H, J=8.4 Hz), 7.67 (d, 1H, J=8.8 Hz), 7.60 (d, 1H, J=8.4 Hz), 6.43 (dd, 1H, J=2.4, 8.8 Hz), 6.40 (d, 1H, J=2.0 Hz); $^{13}$C NMR (100 MHz, CD$_3$OD) δ 171.5, 159.8, 151.9, 153.8, 136.6, 130.2, 128.6 (q, J=31.1 Hz), 124.5 (q, J=270.0 Hz), 122.4, 120.8 (q, J=3.8 Hz), 118.0 (q, J=4.6 Hz), 116.2, 108.5, 102.8; $^{19}$F NMR (470 MHz, CD$_3$OD) δ −63.65.

Example 3-4

Synthesis of 2-methoxy-4-(5-(trifluoromethyl)benzo[d]thiazol-2-yl)phenol (Compound 31)

Yellow solid; a reaction time of 5 hours; a yield of 43.8%; a melting point of 155.7-159.9° C.; $^1$H NMR (400 MHz, CD$_3$OD) δ 8.15 (dd, 1H, J=0.8, 1.6 Hz), 8.11 (dd, 1H, J=0.8, 8.8 Hz), 7.65 (d, 1H, J=2.4 Hz), 7.63 (dd, 1H, J=1.2, 8.8 Hz), 7.51 (dd, 1H, J=2.0, 8.4 Hz), 6.89 (d, 1H, J=8.0 Hz), 3.93 (s, 3H); $^{13}$C NMR (100 MHz, CD$_3$OD) δ 172.2, 151.6, 151.3, 148.5, 137.5, 129.2 (q, J=31.8 Hz), 124.4 (q, J=270.0 Hz), 123.1, 123.1, 122.4, 121.5 (q, J=3.8 Hz), 117.9 (q, J=4.5 Hz), 115.8, 110.2, 55.4; $^{19}$F NMR (470 MHz, CD$_3$OD) δ −63.72.

Example 3-5

Synthesis of 2-ethoxy-4-(5-(trifluoromethyl)benzo[d]thiazol-2-yl)phenol (Compound 32)

Greenish yellow solid; a reaction time of 6 hours; a yield of 28.8%; a melting point of 117.0-117.8° C.; $^1$H NMR (400 MHz, CD$_3$OD) δ 8.10 (dd, 1H, J=0.8, 1.6 Hz), 8.03 (dd, 1H, J=0.8, 8.4 Hz), 7.58 (d, 1H, J=2.0 Hz), 7.56 (dd, 1H, J=1.6, 8.4 Hz), 7.44 (dd, 1H, J=2.0, 8.0 Hz), 6.87 (d, 1H, J=8.0 Hz), 4.13 (q, 2H, J=7.2 Hz), 1.44 (t, 3H, J=7.2 Hz); $^{13}$C NMR (100 MHz, CD$_3$OD) δ 171.5, 153.3, 150.9, 147.5, 138.3, 128.7 (q, J=31.9 Hz), 124.5 (q, J=270.6 Hz), 124.3, 122.6, 121.8, 120.9 (q, J=3.7 Hz), 118.6 (q, J=4.5 Hz), 115.6, 111.1, 64.5, 13.8; $^{19}$F NMR (470 MHz, CD$_3$OD) δ −63.63.

Example 3-6

Synthesis of 2-methoxy-5-(5-(trifluoromethyl)benzo[d]thiazol-2-yl)phenol (Compound 33)

Greenish yellow solid; a reaction time of 7 hours; a yield of 55.9%; a melting point of 142.1-144.5° C.; $^1$H NMR (400 MHz, CD$_3$OD) δ 8.16 (s, 1H), 8.12 (d, 1H, J=8.4 Hz), 7.63 (d, 1H, J=8.4 Hz), 7.54 (dd, 1H, J=2.0, 8.4 Hz), 7.52 (d, 1H, J=2.0 Hz), 7.03 (d, 1H, J=8.4 Hz), 3.91 (s, 3H); $^{13}$C NMR (100 MHz, CD$_3$OD) δ 171.5, 152.9, 151.6, 147.2, 138.3, 128.9 (q, J=32.6 Hz), 125.3, 124.5 (q, J=270.1 Hz), 122.9, 121.2 (q, J=3.8 Hz), 120.2, 118.6 (q, J=3.8 Hz), 113.8, 111.6, 55.3; $^{19}$F NMR (470 MHz, CD$_3$OD) δ −63.66.

Example 3-7

Synthesis of 2-(4-methoxyphenyl)-5-(trifluoromethyl)benzo[d]thiazole (Compound 34)

White solid; a reaction time of 10 hours; a yield of 67.7%; a melting point of 128.8-130.1° C.; $^1$H NMR (500 MHz, CDCl$_3$) δ 8.28 (s, 1H), 8.03 (d, 2H, J=8.5 Hz), 7.96 (d, 1H, J=8.0 Hz), 7.58 (dd, 1H, J=1.0, 8.5 Hz), 7.01 (d, 2H, J=8.5 Hz), 3.89 (s, 3H); $^{13}$C NMR (100 MHz, CDCl$_3$) δ 170.1, 162.6, 154.1, 138.5, 129.5, 129.0 (q, J=31.9 Hz), 126.0, 124.5 (q, J=270.9 Hz), 122.3, 121.3 (q, J=3.0 Hz), 120.1 (q, J=3.8 Hz), 114.7, 55.7; $^{19}$F NMR (470 MHz, CDCl$_3$) δ −66.09;

Example 3-8

Synthesis of 2-(3,4-dimethoxyphenyl)-5-(trifluoromethyl)benzo[d]thiazole (Compound 35)

White solid; a reaction time of 7 hours; a yield of 37.6%; a melting point of 120.4-121.6° C.; $^1$H NMR (500 MHz, CDCl$_3$) δ 8.29 (s, 1H), 7.98 (d, 1H, J=8.5 Hz), 7.72 (d, 1H, J=2.0 Hz), 7.61 (dd, 1H, J=2.0, 8.5 Hz), 7.59 (d, 1H, J=8.5 Hz), 6.96 (d, 1H, J=8.5 Hz), 4.03 (s, 3H), 3.97 (s, 3H); $^{13}$C NMR (100 MHz, CDCl$_3$) δ 170.1, 154.0, 152.3, 149.7, 138.1, 128.8 (q, J=33.4 Hz), 126.2, 124.5 (q, J=270.1 Hz), 122.3, 121.7, 121.4 (q, J=3.8 Hz), 120.2 (q, J=4.3 Hz), 111.3, 110.0, 56.4, 56.3; $^{19}$F NMR (470 MHz, CDCl$_3$) δ −62.17.

Example 3-9

Synthesis of 5-(5-(trifluoromethyl)benzo[d]thiazol-2-yl)benzene-1,3-diol (Compound 36)

In an acetic acid (0.42 mL) solvent, a mixture including 2-amino-4-(trifluoromethyl)benzenethiol (100 mg, 0.44 mmol), 3,5-dihydroxybenzaldehyde (60 mg, 0.44 mmol), and sodium acetate (107 mg, 1.30 mmol) was refluxed for 6.5 hours. After cooling, the reaction mixture was distributed between ethyl acetate and water, and an organic layer was dried by using MgSO$_4$, filtered, and evaporated under reduced pressure. The residual was purified by silica gel column chromatography using hexane and ethyl acetate (2:1) as a developer to obtain a solid Compound 36 (50.6 mg, 37%).

Gray solid; a reaction time of 6.5 hours; a yield of 37.3%; a melting point of 256.7-260.6° C.; $^1$H NMR (400 MHz, CD$_3$OD) δ 8.24 (s, 1H), 8.16 (d, 1H, J=8.4 Hz), 7.66 (d, 1H, J=8.0 Hz), 7.02 (d, 2H, J=2.4 Hz), 6.44 (t, 1H, J=2.0 Hz); $^{13}$C NMR (100 MHz, CD$_3$OD) δ 171.5, 159.3, 153.5, 134.4, 134.4, 128.9 (q, J=31.9 Hz), 124.0 (q, J=270.7 Hz), 122.9, 121.4 (q, J=3.6 Hz), 119.4 (q, J=3.8 Hz), 105.8, 105.8; $^{19}$F NMR (470 MHz, CD$_3$OD) δ −63.70.

Example 3-10

Synthesis of 2-(2,4-dimethoxyphenyl)-5-(trifluoromethyl)benzo[d]thiazole (Compound 37)

White solid; a reaction time of 4 hours; a yield of 34.2%; a melting point of 140.4-141.6° C.; $^1$H NMR (500 MHz, CDCl$_3$) δ 8.48 (d, 1H, J=9.0 Hz), 8.29 (s, 1H), 7.98 (d, 1H, J=8.0 Hz), 7.56 (d, 1H, J=8.0 Hz), 6.69 (dd, 1H, J=2.5, 9.0 Hz), 6.59 (d, 1H, J=2.5 Hz), 4.05 (s, 3H), 3.90 (s, 3H); $^{13}$C NMR (100 MHz, CDCl$_3$) δ 165.5, 163.6, 159.0, 152.0, 139.2, 131.1, 128.6 (q, J=32.6 Hz), 124.7 (q, J=270.1 Hz), 121.9, 120.6 (q, J=3.8 Hz), 119.6 (q, J=4.5 Hz), 115.3, 106.4, 98.7, 55.9, 55.8; $^{19}$F NMR (470 MHz, CDCl$_3$) δ −61.99.

Example 3-11

Synthesis of 2-(5-(trifluoromethyl)benzo[d]thiazol-2-yl)phenol (Compound 38)

White solid; a reaction time of 15 hours; a yield of 47.4%; a melting point of 175.0-176.5° C.; $^1$H NMR (500 MHz, CDCl$_3$) δ 12.15 (s, 1H), 8.25 (s, 1H), 8.01 (d, 1H, J=8.5 Hz), 7.68 (dd, 1H, J=1.0, 8.0 Hz), 7.64 (dd, 1H, J=0.5, 8.0 Hz), 7.42 (td, 1H, J=1.5, 8.0 Hz), 7.12 (d, 1H, J=8.5 Hz), 6.98 (t, 1H, J=7.5 Hz); $^{13}$C NMR (100 MHz, CDCl$_3$) δ 171.6, 158.3, 151.8, 136.2, 133.7, 129.7 (q, J=32.6 Hz), 128.8, 124.9 (q, J=270.0 Hz), 122.4, 122.1 (q, J=3.0 Hz), 120.0, 119.5 (q, J=3.8 Hz), 118.3, 116.5; $^{19}$F NMR (470 MHz, CDCl$_3$) δ −62.23.

Example 3-12

Synthesis of 5-(trifluoromethyl)-2-(3,4,5-trimethoxyphenyl)benzo[d]thiazole (Compound 39)

White solid; a reaction time of 7 hours; a yield of 65.4%; a melting point of 132.5-134.0° C.; $^1$H NMR (500 MHz, CDCl$_3$) δ 8.31 (s, 1H), 7.98 (d, 1H, J=8.0 Hz), 7.60 (d, 1H, J=8.5 Hz), 7.33 (s, 2H), 3.99 (s, 6H), 3.94 (s, 3H); $^{13}$C NMR (100 MHz, CDCl$_3$) δ 170.0, 153.9, 153.9, 141.4, 138.6, 129.2 (q, J=32.7 Hz), 128.6, 124.4 (q, J=270.9 Hz), 122.4, 121.6 (q, J=3.1 Hz), 120.4 (q, J=3.8 Hz), 105.1, 61.2, 56.6; $^{19}$F NMR (470 MHz, CDCl$_3$) δ −62.19.

Example 3-13

Synthesis of 2,6-dimethoxy-4-(5-(trifluoromethyl)benzo[d]thiazol-2-yl)phenol (Compound 40)

Yellow solid; a reaction time of 7 hours; a yield of 27.7%; a melting point of 220.6-222.6° C.; $^1$H NMR (500 MHz, CD$_3$OD) δ 8.19 (s, 1H), 8.14 (d, 1H, J=8.5 Hz), 7.64 (d, 1H, J=8.5 Hz), 7.37 (s, 2H), 3.95 (s, 6H); $^{13}$C NMR (100 MHz, CD$_3$OD) δ 171.6, 153.3, 148.5, 139.8, 138.5, 128.9 (q, J=31.9 Hz), 124.5 (q, J=270.0 Hz), 123.3, 122.8, 121.1 (q, J=3.0 Hz), 118.7 (q, J=3.8 Hz), 105.0, 55.8; $^{19}$F NMR (470 MHz, CD$_3$OD) δ −63.68.

Example 3-14

Synthesis of 2-bromo-4-(5-(trifluoromethyl)benzo[d]thiazol-2-yl)phenol (Compound 41)

In a N,N-dimethylformamide (DMF) solvent, a suspension of 3-bromo-4-hydroxybenzaldehyde (1.0 eq.) and 2-amino-4-(trifluoromethyl)benzenethiol (1.0 eq.) was heated at a temperature of 100° C. After cooling, DMF was removed therefrom under reduced pressure. Methylene chloride was added to the resultant solid, and the produced precipitate was filtered, and washed with methylene chloride to obtain a solid target product.

A reaction time of 8 hours; a yield of 49.2%; $^1$H NMR (400 MHz, DMSO-d$_6$) δ 11.21 (s, 1H), 8.26 (d, 1H, J=8.4 Hz), 8.23 (s, 1H), 8.13 (s, 1H), 7.85 (d, 1H, J=8.4 Hz), 7.65 (d, 1H, J=8.4 Hz), 7.08 (d, 1H, J=8.4 Hz); $^{13}$C NMR (100 MHz, DMSO-d$_6$) δ 169.1, 158.2, 153.7, 139.0, 132.2, 129.1, 128.1 (q, J=31.8 Hz), 125.4, 124.9 (q, J=270.8 Hz), 124.2, 121.7 (d, J=3.1 Hz), 119.8 (d, J=3.8 Hz), 117.5, 110.9.

Example 3-15

Synthesis of 2,6-dibromo-4-(5-(trifluoromethyl)benzo[d]thiazol-2-yl)phenol (Compound 42)

In a N,N-dimethylformamide (DMF) solvent, a suspension of 3,5-dibromo-4-hydroxybenzaldehyde (1.0 eq.) and 2-amino-4-(trifluoromethyl)benzenethiol (1.0 eq.) was heated at a temperature of 100° C. After cooling, DMF was removed therefrom under reduced pressure. Methylene chloride was added to the resultant solid, and the produced precipitate was filtered, and washed with methylene chloride to obtain a solid target product.

A reaction time of 13 hours; a yield of 13.24%; $^1$H NMR (500 MHz, DMSO-d$_6$) δ 10.85 (s, 1H), 8.31 (d, 1H, J=7.5 Hz), 8.27 (s, 1H), 8.13 (s, 2H), 7.70 (d, 1H, J=8.0 Hz); $^{13}$C NMR (100 MHz, DMSO-d$_6$) δ 167.6, 154.8, 153.5, 139.3, 131.6, 128.2 (q, J=31.8 Hz), 126.7, 124.9 (q, J=270.9 Hz), 124.4 (d, J=4.5 Hz), 122.1, 120.1, 113.1.

Example 4

Synthesis of Compounds 43 to 56

Table 4 below is provided to explain substitution patterns of Compounds 43 to 56, which are 2-(substituted phenyl)-1H-benzo[d]imidazole derivatives.

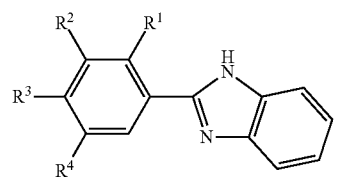

TABLE 4

| Compound | R$^1$ | R$^2$ | R$^3$ | R$^4$ |
|---|---|---|---|---|
| 43 | H | H | OH | H |
| 44 | H | OH | OH | H |
| 45 | OH | H | OH | H |
| 46 | H | OMe | OH | H |
| 47 | H | OEt | OH | H |

TABLE 4-continued

| Compound | $R^1$ | $R^2$ | $R^3$ | $R^4$ |
|---|---|---|---|---|
| 48 | H | OH | OMe | H |
| 49 | H | H | OMe | H |
| 50 | H | OMe | OMe | H |
| 51 | H | OH | H | OH |
| 52 | OMe | H | OMe | H |
| 53 | OH | H | H | H |
| 54 | H | OMe | OMe | OMe |
| 55 | H | OMe | OH | OMe |
| 56 | H | Br | OH | H |

OMe represents a methoxy group, and OEt represents an ethoxy group.

Synthesis of Compounds 43 to 55 was performed as follows. In detail, in a DMF (2 mL) solvent, a mixture including 1,2-phenylenediamine (100 mg, 0.92 mmol), substituted benzaldehyde (1.0 eq.), and $Na_2S_2O_5$ (1.0 eq.) was heated at a temperature of 70 to 80° C. for 1 to 4.5 hours. After DMF was evaporated, the residual was distributed between ethyl acetate and water, and an organic layer was dried by using $MgSO_4$, filtered, and evaporated under reduced pressure. In consideration of physical characteristics of the remaining starting materials, the result was solidified by using methylene chloride and/or water and/or ethyl acetate. The precipitate was filtered to obtain a solid target product.

However, synthesis method of Compound 56, which is different from the method described above, is separately described below.

Example 4-1

Synthesis of 4-(1H-benzo[d]imidazol-2-yl)phenol (Compound 43)

White solid; a reaction time of 4 hours; a yield of 22.4%; a melting point of 284.6 to 285.7° C.; $^1$H NMR (400 MHz, $CD_3OD$) δ 7.90 (d, 2H, J=8.8 Hz), 7.50 (dd, 2H, J=2.8, 6.0 Hz), 7.15 (dd, 2H, J=2.8, 6.0 Hz), 6.91 (d, 2H, J=8.8 Hz); $^{13}$C NMR (100 MHz, $CD_3OD$) δ 159.8, 152.7, 138.8, 128.4, 122.4, 120.9, 115.8, 114.3.

Example 4-2

Synthesis of 4-(1H-benzo[d]imidazol-2-yl)benzene-1,2-diol (Compound 44)

Light brown; a reaction time of 1.5 hours; a yield of 37.2%; a melting point of 268.5 to 269.8° C.; $^1$H NMR (400 MHz, DMSO-$d_6$) δ 12.65 (br s, 1H), 9.45 (s, 1H), 9.22 (s, 1H), 7.57 (d, 1H, J=2.0 Hz), 7.48 (dd, 2H, J=2.8, 6.0 Hz), 7.43 (d, 1H, J=8.4 Hz), 7.10 (dd, 2H, J=2.8, 6.0 Hz), 6.84 (d, 1H, J=2.0, 8.4 Hz); $^{13}$C NMR (100 MHz, DMSO-$d_6$) δ 152.6, 148.1, 146.2, 139.3, 122.2, 122.2, 118.9, 116.4, 115.1, 114.8.

Example 4-3

Synthesis of 4-(1H-benzo[d]imidazol-2-yl)benzene-1,3-diol (Compound 45)

Bright yellow; a reaction time of 1 hours; a yield of 46.2%; a melting point of 279.4 to 280.1° C.; $^1$H NMR (400 MHz, DMSO-$d_6$) δ 12.64 (br s, 1H), 9.67 (br s, 2H), 7.82 (d, 1H, J=8.4 Hz), 7.55 (dd, 2H, J=3.2, 5.6 Hz), 7.19 (dd, 2H, J=3.2, 6.0 Hz), 6.43 (dd, 1H, J=2.0, 8.4 Hz), 6.38 (d, 1H, J=2.0 Hz); $^{13}$C NMR (100 MHz, DMSO-$d_6$) δ 161.5, 160.6, 153.1, 139.3, 128.1, 123.0, 115.5, 108.2, 105.2, 103.7.

Example 4-4

Synthesis of 4-(1H-benzo[d]imidazol-2-yl)-2-methoxyphenol (Compound 46)

Beige solid; a reaction time of 2 hours; a yield of 30.2%; a melting point of 220.5 to 221.7° C.; $^1$H NMR (500 MHz, DMSO-$d_6$) δ 12.64 (br s, 1H), 9.58 (br s, 1H), 7.77 (s, 1H), 7.64 (d, 1H, J=8.0 Hz), 7.55 (br s, 2H), 7.15 (br s, 2H), 6.94 (d, 1H, J=8.0 Hz), 3.88 (s, 3H); $^{13}$C NMR (100 MHz, DMSO-$d_6$) δ 152.5, 149.1, 148.5, 139.3, 122.4, 122.1, 120.4, 116.4, 115.6, 111.1, 56.3.

Example 4-5

Synthesis of 4-(1H-benzo[d]imidazol-2-yl)-2-ethoxyphenol (Compound 47)

Light lemon; a reaction time of 4 hours; a yield of 67.0%; a melting point of 174.0 to 174.6° C.; $^1$H NMR (400 MHz, DMSO-$d_6$) δ 12.63 (br s, 1H), 9.48 (s, 1H), 7.70 (s, 1H), 7.59 (d, 1H, J=8.4 Hz), 7.50 (dd, 2H, J=3.2, 6.0 Hz), 7.12 (dd, 2H, J=3.2, 6.0 Hz), 6.90 (d, 1H, J=8.4 Hz), 4.12 (q, 2H, J=6.8 Hz), 1.35 (t, 3H, J=6.8 Hz)l; $^{13}$C NMR (100 MHz, DMSO-$d_6$) δ 152.5, 149.4, 147.7, 135.7, 122.4, 122.1, 120.4, 118.4, 116.5, 112.2, 64.6, 15.4.

Example 4-6

Synthesis of 5-(1H-benzo[d]imidazol-2-yl)-2-methoxyphenol (Compound 48)

White solid; a reaction time of 2.5 hours; a yield of 45.0% melting point, 249.7 to 250.7° C.; $^1$H NMR (400 MHz, DMSO-$d_6$) δ 12.62 (br s, 1H), 9.29 (br s, 1H), 7.61 (d, 1H, J=2.0 Hz), 7.57 (d, 1H, J=2.0, 7.2 Hz), 7.50 (dd, 2H, J=2.8, 6.0 Hz), 7.12 (dd, 2H, J=2.8, 6.0 Hz), 7.04 (d, 1H, J=7.2 Hz), 3.80 (s, 3H); $^{13}$C NMR (100 MHz, DMSO-$d_6$) δ152.2, 150.0, 147.3, 139.3, 123.6, 122.4, 118.6, 115.1, 114.4, 112.8, 56.3.

Example 4-7

Synthesis of 2-(4-methoxyphenyl)-1H-benzo[d]imidazole (Compound 49)

White solid; a reaction time of 4.5 hours; a yield of 24.2%; a melting point of 226.4 to 227.8° C.; $^1$H NMR (400 MHz, DMSO-$d_6$) δ 12.61 (br s, 1H), 8.14 (d, 2H, J=8.8 Hz), 7.56 (dd, 2H, J=3.2, 6.0 Hz), 7.15 (dd, 2H, J=3.2, 6.0 Hz), 7.08 (d, 2H, J=8.8 Hz), 3.79 (s, 3H); $^{13}$C NMR (100 MHz, DMSO-$d_6$) δ 161.3, 152.1, 138.8, 128.7, 123.4, 122.4, 115.0, 115.0, 55.9.

Example 4-8

Synthesis of 2-(3,4-dimethoxyphenyl)-1H-benzo[d]imidazole (Compound 50)

Yellowish white crystal; a reaction time of 2.5 hours; a yield of 39.9%; a melting point of 219.0 to 221.6° C.; $^1$H NMR (500 MHz, DMSO-$d_6$) δ 12.63 (br s, 1H), 7.77 (d, 1H, J=2.0 Hz), 7.74 (dd, 1H, J=2.0, 9.0 Hz), 7.56 (dd, 2H, J=3.0, 6.0 Hz), 7.17 (dd, 2H, J=3.0, 6.0 Hz), 7.12 (d, 1H, J=8.5 Hz), 3.87 (s, 3H), 3.83 (s, 3H); $^{13}$C NMR (100 MHz, DMSO-$d_6$) δ 152.1, 151.0, 149.6, 139.3, 123.4, 122.5, 120.0, 115.1, 112.5, 110.4, 56.3, 56.3.

Example 4-9

Synthesis of 5-(1H-benzo[d]imidazol-2-yl)benzene-1,3-diol (Compound 51)

Light brown of a mixture of beige and brown; a reaction time of 3.5 hours; a yield of 16.2%; a melting point of >300° C.; $^1$H NMR (400 MHz, DMSO-$d_6$) δ 12.62 (br s, 1H), 9.53 (s, 2H), 7.52 (dd, 2H, J=3.2, 6.4 Hz), 7.15 (dd, 2H, J=3.2, 6.4 Hz), 7.01 (d, 2H, J=2.0 Hz), 6.33 (t, 1H, J=2.0 Hz); $^{13}$C NMR (100 MHz, DMSO-$d_6$) δ 159.4, 152.2, 139.3, 132.3, 122.7, 115.8, 105.5, 104.9.

Example 4-10

Synthesis of 2-(2,4-dimethoxyphenyl)-1H-benzo[d]imidazole (Compound 52)

Beige solid; a reaction time of 2.5 hours; a yield of 40.7%; a melting point of 197.5 to 198.8° C.; $^1$H NMR (500 MHz, DMSO-$d_6$) δ 12.65 (br s, 1H), 8.27 (d, 1H, J=9.0 Hz), 7.59 (dd, 2H, J=3.0, 6.0 Hz), 7.16 (dd, 2H, J=3.0, 6.0 Hz), 6.75 (s, 1H), 6.71 (dd, 1H, J=2.5, 9.0 Hz), 4.01 (s, 3H), 3.85 (s, 3H); $^{13}$C NMR (100 MHz, DMSO-$d_6$) δ 162.7, 158.8, 149.9, 139.3, 131.6, 122.2, 115.5, 111.6, 106.9, 99.2, 56.5, 56.1.

Example 4-11

Synthesis of 2-(1H-benzo[d]imidazol-2-yl)phenol (Compound 53)

Orange; a reaction time of 2 hours; a yield of 37.0%; a melting point of 237.3 to 241.0° C.; $^1$H NMR (400 MHz, DMSO-$d_6$) δ 12.63 (br s, 1H), 8.01 (d, 1H, J=7.6 Hz), 7.63 (dd, 2H, J=3.2, 6.0 Hz), 7.34 (t, 1H, J=7.6 Hz), 7.25 (dd, 2H, J=3.2, 6.0 Hz), 7.00 (d, 1H, J=8.4 Hz), 6.98 (t, 1H, J=7.2 Hz); $^{13}$C NMR (100 MHz, DMSO-$d_6$) δ 158.7, 152.3, 139.3, 132.4, 126.9, 123.5, 119.8, 117.9, 115.1, 113.2.

Example 4-12

Synthesis of 2-(3,4,5-trimethoxyphenyl)-1H-benzo[d]imidazole (Compound 54)

Beige-ish white; a reaction time of 2 hours; a yield of 21.1%; a melting point of 257.0 to 257.7° C.; $^1$H NMR (400 MHz, DMSO-$d_6$) δ 12.62 (br s, 1H), 7.57 (dd, 2H, J=3.2, 5.6 Hz), 7.50 (s, 2H), 7.17 (dd, 2H, J=3.2, 6.0 Hz), 3.87 (s, 6H), 3.70 (s, 3H); $^{13}$C NMR (100 MHz, DMSO-$d_6$) δ 153.9, 151.9, 139.6, 138.0, 126.1, 122.7, 115.1, 104.5, 60.8, 56.7.

Example 4-13

Synthesis of 4-(1H-benzo[d]imidazol-2-yl)-2,6-dimethoxyphenol (Compound 55)

Ivory; a reaction time of 2 hours; a yield of 48.7%; a melting point of 193.6 to 195.1° C.; $^1$H NMR (400 MHz, DMSO-$d_6$) δ 12.60 (br s, 1H), 8.87 (s, 1H), 7.52 (dd, 2H, J=2.8, 5.6 Hz), 7.45 (s, 2H), 7.13 (dd, 2H, J=2.8, 6.0 Hz), 3.85 (s, 6H); $^{13}$C NMR (100 MHz, DMSO-$d_6$) δ 152.5, 148.9, 139.4, 138.2, 122.4, 120.9, 115.1, 104.7, 56.8.

Example 4-14

Synthesis of 4-(1H-benzo[d]imidazol-2-yl)-2-bromophenol (Compound 56)

In a DMF (3 mL) solvent, a mixture including 1,2-phenylenediamine (100 mg, 0.92 mmol), 3-bromo-4-hydroxybenzaldehyde (187.8 mg, 0.92 mmol), and $Na_2S_2O_5$ (177.6 mg, 0.92 mmol) was mixed at a temperature of 80° C. for 1 hour. After cooling, DMF was removed therefrom under reduced pressure. Methylene chloride and water were added thereto to obtain a solid product, and the precipitate was filtered, and the filtered product was washed with methylene chloride, ethyl acetate, and water to obtain a solid Compound 56 (79.4%).

A reaction time of 1 hour; a yield of 79.4%; $^1$H NMR (500 MHz, DMSO-$d_6$) δ 10.84 (s, 1H), 8.29 (s, 1H), 7.99 (d, 1H, J=8.4 Hz), 7.52 (m, 2H), 7.14 (m, 2H), 7.07 (d, 1H, J=8.4 Hz); $^{13}$C NMR (100 MHz, DMSO-$d_6$) δ 156.3, 151.0, 139.8, 131.6, 127.9, 123.4, 122.6, 117.3, 115.5, 110.4.

Example 5

Synthesis of Compounds 57 to 70

Table 5 below is provided to explain substitution patterns of Compounds 57 to 70, which are 2-(substituted phenyl)-1H-benzo[d]imidazole-5-carboxylic acid derivatives.

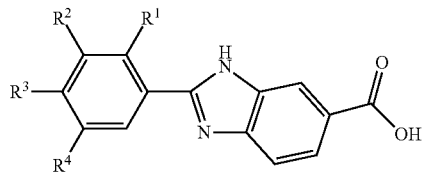

TABLE 5

| Compound | $R^1$ | $R^2$ | $R^3$ | $R^4$ |
|---|---|---|---|---|
| 57 | H | H | OH | H |
| 58 | H | OH | OH | H |
| 59 | OH | H | OH | H |
| 60 | H | OMe | OH | H |
| 61 | H | OEt | OH | H |
| 62 | H | OH | OMe | H |
| 63 | H | H | OMe | H |
| 64 | H | OMe | OMe | H |
| 65 | OMe | H | OMe | H |
| 66 | OH | H | H | H |
| 67 | H | OMe | OMe | OMe |
| 68 | H | OMe | OH | OMe |
| 69 | H | Br | OH | H |
| 70 | H | Br | OH | Br |

OMe represents a methoxy group, and OEt represents an ethoxy group.

Synthesis of Compounds 57 to 70 was performed as follows. In detail, a solution including 3,4-diaminobenzoic acid (1.0 eq.), substituted benzaldhehyde (1.0 eq.), and $Na_2S_2O_5$ (1.0 eq.) was heated in an anhydrous DMF at a temperature of 80° C. After cooling, DMF was removed therefrom under reduced pressure. The residual was distributed between ethyl acetate and water, and an organic layer was dried by using MgSO$_4$, filtered, and evaporated. The filtrate was evaporated, and the resultant solid was filtered and washed with water and methylene chloride and/or ethyl acetate to obtain a target product.

Example 5-1

Synthesis of 2-(4-hydroxyphenyl)-1H-benzo[d]imidazole-5-carboxylic acid (Compound 57)

Beige solid; a reaction time of 3 hours; a yield of 66.0%; a melting point of >300° C.; $^1$H NMR (500 MHz, DMSO-d$_6$) δ 12.91 (s, 1H), 12.62 (s, 1H), 10.02 (s, 1H), 8.09 (br s, 1H), 8.01 (d, 2H, J=8.5 Hz), 7.78 (d, 1H, J=8.0 Hz), 7.57 (br s, 1H), 6.92 (d, 2H, J=8.5 Hz).

Example 5-2

Synthesis of 2-(3,4-dihydroxyphenyl)-1H-benzo[d]imidazole-5-carboxylic acid (Compound 58)

A reaction time of 6 hours; a yield of 11.6%; $^1$H NMR (500 MHz, DMSO-d$_6$) δ12.58 (s, 1H), 9.56 (s, 1H), 9.29 (s, 1H), 8.10 (s, 1H), 7.79 (d, 1H, J=8.5 Hz), 7.61 (s, 1H), 7.57 (d, 1H, J=8.0 Hz), 7.48 (d, 1H, J=7.5 Hz), 6.89 (d, 1H, J=8.0 Hz).

Example 5-3

Synthesis of 2-(2,4-dihydroxyphenyl)-1H-benzo[d]imidazole-5-carboxylic acid (Compound 59)

Yellow solid; a reaction time of 4.2 hours; a yield of 57.1%; a melting point of >300° C.; $^1$H NMR (500 MHz, DMSO-d$_6$) δ 12.89 (s, 2H), 10.08 (s, 1H), 8.15 (s, 1H), 7.87 (d, 1H, J=9.0 Hz), 7.85 (d, 1H, J=9.0 Hz), 7.63 (d, 1H, J=8.5 Hz), 6.47 (d, 1H, J=8.5 Hz), 6.43 (s, 1H).

Example 5-4

Synthesis of 2-(4-hydroxy-3-methoxyphenyl)-1H-benzo[d]imidazole-5-carboxylic acid (Compound 60)

Light brown solid; a reaction time of 6 hours; a yield of 39.6%; a melting point of >300° C.; $^1$H NMR (500 MHz, DMSO-d$_6$) δ 12.91 (s, 1H), 9.67 (s, 1H), 8.14 (br s, 1H), 7.82 (d, 1H, J=8.5 Hz), 7.77 (s, 1H), 7.66 (d, 1H, J=8.0 Hz), 7.62 (d, 1H, J=8.5 Hz), 6.97 (d, 1H, J=7.0 Hz), 3.89 (s, 3H).

Example 5-5

Synthesis of 2-(3-ethoxy-4-hydroxyphenyl)-1H-benzo[d]imidazole-5-carboxylic acid (Compound 61)

Light yellow solid; a reaction time of 4.2 hours; a yield of 57.1%; a melting point of >300° C.; $^1$H NMR (400 MHz, DMSO-d$_6$) δ 12.91 (s, 1H), 9.56 (s, 1H), 8.10 (d, 1H, J=8.4 Hz), 7.71 (s, 1H), 7.61 (d, 1H, J=8.4 Hz), 7.57 (d, 1H, J=8.0 Hz), 6.92 (d, 1H, J=8.4 Hz), 4.11 (q, 2H, J=6.8 Hz), 1.36 (t, 3H, J=6.8 Hz).

Example 5-6

Synthesis of 3-hydroxy-4-methoxyphenyl)-1H-benzo[d]imidazole-5-carboxylic acid (Compound 62)

Light brown solid; a reaction time of 4 hours; a yield of 72.6%; a melting point of 246.6 to 247.7° C.; $^1$H NMR (500 MHz, DMSO-d$_6$) δ 12.95 (s, 1H), 9.39 (s, 1H), 8.15 (s, 1H), 7.82 (dd, 1H, J=1.5, 8.5 Hz), 7.66 (d, 1H, J=2.5 Hz), 7.62 (dd, 1H, J=2.0, 8.5 Hz), 7.61 (d, 1H, J=8.5 Hz), 7.09 (d, 1H, J=8.5 Hz), 3.84 (s, 3H).

Example 5-7

Synthesis of 2-(4-methoxyphenyl)-1H-benzo[d]imidazole-5-carboxylic acid (Compound 63)

Ivory white solid; a reaction time of 4 hours; a yield of 20.7%; a melting point of 264.7 to 265.4° C.; $^1$H NMR (400 MHz, DMSO-d$_6$) δ 12.91 (s, 1H), 8.10 (m, 3H), 7.78 (d, 1H, J=8.4 Hz), 7.58 (br s, 1H), 7.10 (d, 2H, J=9.2 Hz), 3.81 (s, 3H);

Example 5-8

Synthesis of 2-(3,4-dimethoxyphenyl)-1H-benzo[d]imidazole-5-carboxylic acid (Compound 64)

A reaction time of 4.5 hours; a yield of 78.6%; $^1$H NMR (400 MHz, DMSO-d$_6$) δ 12.84 (s, 2H), 8.15 (s, 1H), 7.81 (d, 1H, J=8.4 Hz), 7.75 (s, 1H), 7.74 (d, 1H, J=9.2 Hz), 7.60 (d, 1H, J=8.0 Hz), 7.08 (d, 1H, J=7.6 Hz), 3.85 (s, 3H), 3.79 (s, 3H).

Example 5-9

Synthesis of 2-(2,4-dimethoxyphenyl)-1H-benzo[d]imidazole-5-carboxylic acid (Compound 65)

A reaction time of 5 hours; a yield of 77.6%; $^1$H NMR (400 MHz, DMSO-d$_6$) δ 12.18 (s, 1H), 8.26 (d, 1H, J=8.4 Hz), 8.20 (s, 1H), 7.78 (d, 1H, J=8.4 Hz), 7.60 (d, 1H, J=8.4 Hz), 6.73 (s, 1H), 6.69 (d, 1H, J=9.2 Hz), 3.99 (s, 3H), 3.82 (s, 3H).

Example 5-10

Synthesis of 2-(2-hydroxyphenyl)-1H-benzo[d]imidazole-5-carboxylic acid (Compound 66)

A reaction time of 4.5 hours; a yield of 45.5%; $^1$H NMR (400 MHz, DMSO-d$_6$) δ 12.92 (s, 3H), 8.21 (s, 1H), 8.05 (d, 1H, J=8.0 Hz), 7.87 (d, 1H, J=8.4 Hz), 7.69 (d, 1H, J=8.0 Hz), 7.37 (t, 1H, J=7.6 Hz), 7.03 (d, 1H, J=8.4 Hz), 6.99 (t, 1H, J=7.2 Hz).

Example 5-11

Synthesis of 2-(3,4,5-trimethoxyphenyl)-1H-benzo[d]imidazole-5-carboxylic acid (Compound 67)

A reaction time of 4 hours; a yield of 61.4%; $^1$H NMR (400 MHz, DMSO-d$_6$) δ 8.16 (s, 1H), 7.83 (d, 1H, J=8.0 Hz), 7.64 (d, 1H, J=8.4 Hz), 7.51 (s, 2H), 3.88 (s, 6H), 3.72 (s, 3H); $^{13}$C NMR (100 MHz, DMSO-d$_6$) δ 168.4, 154.0, 154.0, 142.5, 140.2, 139.5, 125.5, 125.0, 124.4, 117.5, 115.0, 104.9, 60.8, 56.8.

Example 5-12

Synthesis of 4-hydroxy-3,5-dimethoxyphenyl)-1H-benzo[d]imidazole-5-carboxylic acid (Compound 68)

Beige solid; a reaction time of 6 hours; a yield of 52.8%; a melting point of 280.0 to 281.4° C.; $^1$H NMR (500 MHz, DMSO-d$_6$) δ 12.97 (s, 1H), 9.05 (s, 1H), 8.15 (s, 1H), 7.82 (d, 1H, J=8.0 Hz), 7.62 (d, 1H, J=7.5 Hz), 7.51 (s, 1H), 7.50 (s, 1H), 3.88 (s, 3H), 3.87 (s, 3H).

Example 5-13

Synthesis of 2-(3-bromo-4-hydroxyphenyl)-1H-benzo[d]imidazole-5-carboxylic acid (Compound 69)

A reaction time of 5.5 hours; a yield of 99%; $^1$H NMR (400 MHz, DMSO-d$_6$) δ 10.95 (br s, 1H), 8.29 (s, 1H), 8.11 (s, 1H), 7.99 (br s, 1H), 7.79 (br s, 1H), 7.57 (br s, 1H), 7.07 (br s, 1H); $^{13}$C NMR (100 MHz, DMSO-d$_6$) δ 168.5, 156.9, 153.2, 143.0, 139.6, 132.0, 128.3, 125.1, 124.2, 122.6, 117.4, 115.0, 110.5.

Example 5-14

Synthesis of 2-(3,5-dibromo-4-hydroxyphenyl)-1H-benzo[d]imidazole-5-carboxylic acid (Compound 70)

A reaction time of 4 hours; a yield of 87.7%; $^1$H NMR (400 MHz, DMSO-d$_6$) δ 8.31 (s, 2H), 8.11 (s, 1H), 7.79 (d, 1H, J=8.0 Hz), 7.56 (d, 1H, J=8.0 Hz); $^{13}$C NMR (100 MHz, DMSO-d6) δ 168.5, 155.2, 152.3, 143.1, 139.7, 131.1, 125.2, 124.2, 122.3, 117.4, 115.0, 113.5

Example 6

Synthesis of Compounds 71 to 80

Table 6 below is provided herein to explain substitution patterns of Compound 71 to 80, which are 2-(substituted phenyl)thiazolidine derivatives.

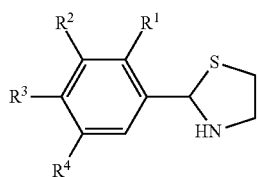

TABLE 6

| Compound | R$^1$ | R$^2$ | R$^3$ | R$^4$ |
|---|---|---|---|---|
| 71 | H | H | OH | H |
| 72 | H | OH | OH | H |
| 73 | H | OMe | OH | H |
| 74 | H | OEt | OH | H |
| 75 | H | OH | OMe | H |

TABLE 6-continued

| Compound | R$^1$ | R$^2$ | R$^3$ | R$^4$ |
|---|---|---|---|---|
| 76 | H | H | OMe | H |
| 77 | H | OMe | OMe | H |
| 78 | OMe | H | OMe | H |
| 79 | H | OMe | OMe | OMe |
| 80 | H | OMe | OH | OMe |

OMe represents a methoxy group, and OEt represents an ethoxy group.

Synthesis of Compounds 71 to 79 was performed as follows. In detail, in a DMF (5 mL) solvent, triethylamine (1.0 eq.) was added to a mixture including substituted benzaldehyde (300 mg) and cysteamine.HCl (1.5 eq.), and then the reaction mixture was stirred at room temperature for 2 to 4 hours. After water was added thereto, the reaction flask was maintained at a temperature of 0° C., and the produced precipitate was filtered and washed with iced water to obtain a target product. In the case of Compound 79, after the reaction mixture was stirred, DMF was evaporated therefrom under reduced pressure, and the residual was distributed between methylene chloride and NaHCO$_3$ aqueous solution. An organic layer was dried by using MgSO$_4$, filtered, and evaporated. The residual was purified by silica gel column chromatography using a mixture including methylene chloride and methanol (60:1) as a developer to obtain a solid Compound 79

However, a synthesis method of Compound 80, which is slightly different from the method described above, is separately described below.

Example 6-1

Synthesis of 4-(thiazolidin-2-yl)phenol (Compound 71)

A reaction time of 2 hours; a yield of 77.3%; $^1$H NMR (500 MHz, DMSO-d$_6$) δ 9.40 (s, 1H), 7.25 (d, 2H, J=9.0 Hz), 6.69 (d, 2H, J=9.5 Hz), 5.33 (s, 1H), 3.49 (br m, 1H), 3.06 (br s, 1H), 2.98-2.90 (m, 2H), 2.81 (br m, 1H); $^{13}$C NMR (100 MHz, DMSO-d$_6$) δ 157.5, 131.3, 129.1, 115.5, 73.9, 53.4, 36.8.

Example 6-2

Synthesis of 4-(Thiazolidin-2-yl)benzene-1,2-diol (Compound 72)

A reaction time of 3 hours; a yield of 11.8%; $^1$H NMR (500 MHz, DMSO-d$_6$) δ 8.56 (s, 2H), 6.83 (s, 1H), 6.69 (d, 1H, J=8.0 Hz), 6.64 (d, 1H, J=8.0 Hz), 5.26 (s, 1H), 3.46 (br m, 1H), 2.95 (br s, 1H), 2.96-2.87 (m, 2H), 2.79 (br m, 1H); $^{13}$C NMR (100 MHz, DMSO-d$_6$) δ 145.6, 145.5, 131.9, 118.8, 115.7, 115.4, 74.0, 53.3, 36.7.

Example 6-3

Synthesis of 2-methoxy-4-(thiazolidin-2-yl)phenol (Compound 73)

A reaction time of 4 hours; a yield of 88.1%; $^1$H NMR (500 MHz, DMSO-d$_6$) δ 8.91 (s, 1H), 6.89 (s, 1H), 6.83 (s, 2H), 5.32 (s, 1H), 3.73 (s, 3H), 3.46 (br m, 1H), 3.04 (br s, 1H), 2.97-2.91 (m, 2H), 2.84 (br m, 1H); $^{13}$C NMR (100 MHz, DMSO-d$_6$) δ 147.8, 146.8, 133.8, 118.6, 115.2, 112.4, 73.7, 56.3, 53.3, 36.7.

Example 6-4

Synthesis of 2-ethoxy-4-(thiazolidin-2-yl)phenol (Compound 74)

A reaction time of 3 hours; a yield of 87.2%; $^1$H NMR (400 MHz, DMSO-$d_6$) δ 8.85 (s, 1H), 6.99 (s, 1H), 6.80 (d, 1H, J=8.0 Hz), 6.67 (d, 1H, J=8.0 Hz), 5.28 (s, 1H), 3.96 (q, 2H, J=6.8 Hz), 3.47 (br m, 1H), 3.08 (br s, 1H), 2.92-2.89 (m, 2H), 2.77 (br m, 1H), 1.28 (t, 3H, J=6.8 Hz); $^{13}$C NMR (100 MHz, DMSO-$d_6$) δ 147.1, 147.1, 131.8, 120.6, 115.6, 113.4, 74.1, 64.5, 53.4, 36.8, 15.5.

Example 6-5

Synthesis of 2-methoxy-5-(thiazolidin-2-yl)phenol (Compound 75)

A reaction time of 4 hours; a yield of 90.2%; $^1$H NMR (500 MHz, DMSO-$d_6$) δ 8.94 (s, 1H), 7.04 (s, 1H), 6.84 (d, 1H, J=8.0 Hz), 6.69 (d, 1H, J=8.0 Hz), 5.33 (s, 1H), 3.75 (s, 3H), 3.52 (br m, 1H), 3.11 (br s, 1H), 2.99-2.92 (m, 2H), 2.81 (br m, 1H); $^{13}$C NMR (100 MHz, DMSO-$d_6$) δ148.0, 146.8, 131.9, 120.5, 115.6, 112.0, 74.1, 56.3, 53.4, 36.8.

Example 6-6

Synthesis of 2-(4-methoxyphenyl)thiazolidine (Compound 76)

A reaction time of 2 hours; a yield of 72.3%; $^1$H NMR (500 MHz, CDCl$_3$) δ 7.42 (d, 2H, J=7.0 Hz), 6.88 (d, 2H, J=7.0 Hz), 5.52 (s, 1H), 3.80 (s, 3H), 3.64 (br m, 1H), 3.15-3.05 (m, 3H), 1.89 (br s, 1H); $^{13}$C NMR (100 MHz, CDCl$_3$) δ159.7, 132.1, 128.7, 114.1, 73.3, 55.5, 53.0, 36.8.

Example 6-7

Synthesis of 2-(3,4-dimethoxyphenyl)thiazolidine (Compound 77)

A reaction time of 3 hours; a yield of 74.9%; $^1$H NMR (500 MHz, DMSO-$d_6$) δ 7.06 (s, 1H), 6.96 (d, 1H, J=8.0 Hz), 6.86 (d, 1H, J=8.0 Hz), 5.37 (s, 1H), 3.73 (s, 3H), 3.72 (s, 3H), 3.50 (br m, 1H), 3.18 (br s, 1H), 2.98-2.92 (m, 2H), 2.84 (br m, 1H); $^{13}$C NMR (100 MHz, DMSO-$d_6$) δ 149.2, 149.0, 133.5, 120.1, 112.0, 111.6, 73.9, 56.2, 56.1, 53.4, 36.8.

Example 6-8

Synthesis of 2-(2,4-dimethoxyphenyl)thiazolidine (Compound 78)

A reaction time of 3 hours; a yield of 48%; $^1$H NMR (500 MHz, CDCl$_3$) δ 7.37 (d, 1H, J=9.5 Hz), 6.47 (s, 1H), 6.46 (d, 1H, J=9.5 Hz), 5.75 (s, 1H), 3.84 (s, 3H), 3.80 (s, 3H), 3.66 (br m, 1H), 3.10-2.99 (m, 3H), 2.31 (br s, 1H); $^{13}$C NMR (100 MHz, CDCl$_3$) δ 160.9, 158.5, 128.3, 120.5, 104.4, 99.1, 68.7, 55.8, 55.6, 53.2, 36.4.

Example 6-9

Synthesis of 2-(3,4,5-trimethoxyphenyl)thiazolidine (Compound 79)

A reaction time of 3 hours; a yield of 95.6%; $^1$H NMR (500 MHz, CD3OD-d4) δ 6.81 (s, 2H), 5.37 (s, 1H), 3.80 (s, 6H), 3.73 (s, 3H), 3.58 (br m, 1H), 3.11-3.07 (m, 2H), 3.06 (m, 1H); $^{13}$C NMR (100 MHz, CD3OD-d4) δ 153.3, 137.5, 135.7, 104.7, 72.6, 60.0, 55.5, 52.2, 35.5.

Example 6-10

Synthesis of 2,6-dimethoxy-4-(thiazolidin-2-yl)phenol (Compound 80)

In a solvent including an ethyl alcohol (2 mL) and water (2 mL), a mixture including syringaldehyde (100 mg, 0.55 mmol), cysteamine.HCl (93.2 mg, 0.82 mmol), and sodium acetate (72 mg, 0.88 mmol) was stirred at room temperature for 4 hours. The produced precipitate was filtered and washed with water and methylene chloride to obtain a solid target product Compound 80.

A reaction time of 4 hours; a yield of 44.4%; $^1$H NMR (500 MHz, DMSO-$d_6$) δ 8.31 (s, 1H), 6.73 (s, 2H), 5.32 (d, 1H, J=11.5 Hz), 3.73 (s, 6H), 3.51 (br m, 1H), 3.15 (m, 1H), 2.99-2.92 (m, 2H), 2.82 (m, 1H); $^{13}$C NMR (100 MHz, DMSO-$d_6$) δ148.3, 135.7, 131.0, 105.5, 74.4, 56.6, 53.4, 36.8.

Example 7

Synthesis of 4-(1,3-dithiolan-2-yl)phenol (Compound 81)

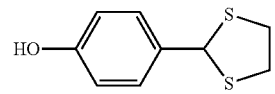

In a tetrahydrofuran (THF) (3 mL) solvent, boron trifluoride diethyl etherate (0.03 mL, 0.25 mmol) was added to a mixed solution including 4-hydroxybenzaldehyde (300 mg, 2.16 mmol) and 1,2-ethanedithiol (0.21 mL, 2.46 mmol), and the reaction mixture was stirred at room temperature for 7 hours. The reaction mixture was distributed between methylene chloride and water, and an organic layer was dried by using MgSO4, filtered, and evaporated under reduced pressure to obtain Compound 81 (465 mg, 95.3%).

A reaction time of 7 hours; a yield of 95.3%; $^1$H NMR (500 MHz, CDCl$_3$) δ 7.39 (d, 2H, J=8.5 Hz), 6.75 (d, 2H, J=9.0 Hz), 5.61 (s, 1H), 5.07 (br s, 1H), 3.48 (m, 2H), 3.33 (m, 2H); $^{13}$C NMR (100 MHz, CDCl$_3$) δ 155.6, 132.2, 129.6, 115.5, 56.2, 40.4.

Example 8

Synthesis of Compounds 82 to 96

Table 7 below is provided to explain substitution patterns of Compounds 82 to 93 and 95 and 96, which are 5-chloro-2-(substituted phenyl)benzo[d]thiazole derivatives. Compound 94 has the following dihydrobenzo[d]thiazol structure.

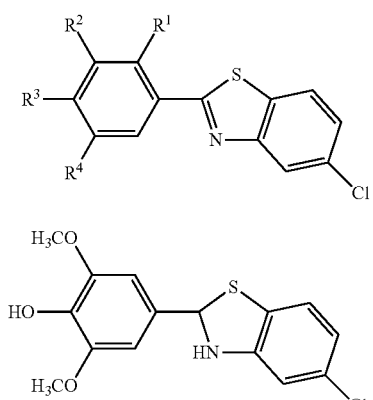

화합물

TABLE 7

| Compound | R¹ | R² | R³ | R⁴ |
| --- | --- | --- | --- | --- |
| 82 | H | H | OH | H |
| 83 | H | OH | OH | H |
| 84 | OH | H | OH | H |
| 85 | H | OMe | OH | H |
| 86 | H | OEt | OH | H |
| 87 | H | OH | OMe | H |
| 88 | H | H | OMe | H |
| 89 | H | OMe | OMe | H |
| 90 | H | OH | H | OH |
| 91 | OMe | H | OMe | H |
| 92 | OH | H | H | H |
| 93 | H | OMe | OMe | OMe |
| 95 | H | Br | OH | H |
| 96 | H | Br | OH | Br |

OMe represents a methoxy group, and OEt represents an ethoxy group.

Synthesis of Compounds 82 to 89, and 91 to 94 was performed as follows. In detail, in a methyl alcohol (3 mL) solvent, a mixture of 2-amino-4-chlorobenzenethiol (100 mg, 0.63 mmol) and substituted benzaldehyde (1.5 eq.) was stirred at room temperature for 0.5 to 8 hours. The reaction solvent was evaporated, and the resultant product was solidified by using small amounts of methanol or a mixed solvent including hexane and ethyl acetate or methylene chloride to obtain solid Compounds 82 to 89 and 91 to 94.

However, synthesis methods of Compounds 90, 95 and 96, which are different from the method described above, were separately described below.

Example 8-1

Synthesis of 4-(5-chlorobenzo[d]thiazol-2-yl)phenol (Compound 82)

Dark ochroid; a reaction time of 3 hours; a yield of 30.5%; a melting point of 259.3 to 263.1° C. $^1$H NMR (500 MHz, DMSO-$d_6$) δ 10.29 (s, 1H), 8.10 (d, 1H, J=9.0 Hz), 8.02 (d, 1H, J=2.0 Hz), 7.91 (d, 2H, J=8.5 Hz), 7.43 (d, 1H, J=9.0 Hz), 6.92 (d, 2H, J=8.5 Hz); $^{13}$C NMR (100 MHz, DMSO-$d_6$) δ 170.5, 161.5, 155.3, 133.5, 131.8, 129.9, 125.6, 124.3, 124.2, 122.3, 116.8.

Example 8-2

Synthesis of 4-(5-chlorobenzo[d]thiazol-2-yl)benzene-1,2-diol (Compound 83)

Beige solid; a reaction time of 10.5 hours; a yield of 33.5%; a melting point of 127.4 to 129.1° C.; $^1$H NMR (500 MHz, DMSO-$d_6$) δ 9.78 (s, 1H), 9.57 (s, 1H), 8.00-7.95 (m, 2H), 7.55 (s, 1H), 7.36-7.34 (m, 2H), 6.90 (dd, 1H, J=2.5, 8.5 Hz); $^{13}$C NMR (100 MHz, DMSO-$d_6$) δ 170.6, 155.3, 150.1, 146.5, 133.5, 131.8, 125.4, 124.7, 124.0, 122.3, 120.4, 116.8, 114.7.

Example 8-3

Synthesis of 4-(5-chlorobenzo[d]thiazol-2-yl)benzene-1,3-diol (Compound 84)

Lemon-colored solid; a reaction time of 2.7 hours; a yield of 36.3%; a melting point of 277.9 to 280.1° C.; $^1$H NMR (400 MHz, DMSO-$d_6$) δ 11.43 (s, 1H), 10.17 (s, 1H) 8.03 (d, 1H, J=8.8 Hz), 7.97 (d, 1H, J=2.0 Hz), 7.94 (d, 1H, J=9.2 Hz), 7.35 (dd, 1H, J=2.0, 8.4 Hz), 6.42 (s, 1H), 6.41 (d, 1H, J=8.8 Hz); $^{13}$C NMR (100 MHz, DMSO-$d_6$) δ 168.2, 162.5, 158.9, 153.3, 133.3, 131.6, 130.7, 124.9, 123.9, 121.5, 111.1, 109.2, 103.2.

Example 8-4

Synthesis of 4-(5-chlorobenzo[d]thiazol-2-yl (Compound 85)

Light brown solid; a reaction time of 30 분; a yield of 14.7%; a melting point of 173.4 175.4° C.; $^1$H NMR (500 MHz, DMSO-$d_6$) δ 9.93 (s, 1H), 8.10 (d, 1H, J=8.5 Hz), 8.05 (d, 1H, J=2.0 Hz), 7.59 (d, 1H, J=2.0 Hz), 7.50 (dd, 1H, J=2.0, 8.0 Hz), 7.44 (dd, 1H, J=2.0, 8.5 Hz), 6.93 (d, 1H, J=8.0 Hz), 3.88 (s, 3H); $^{13}$C NMR (100 MHz, DMSO-$d_6$) δ 170.6, 155.3, 151.1, 148.8, 133.6, 131.8, 125.7, 124.7, 124.3, 122.4, 122.2, 116.6, 110.8, 56.4.

Example 8-5

Synthesis of 4-(5-chlorobenzo[d]thiazol-2-yl)-2-ethoxyphenol (Compound 86)

White solid; a reaction time of 10.5 hours; a yield of 20.2%; a melting point of 102.1 to 103.4° C. $^1$H NMR (400 MHz, DMSO-$d_6$) δ 9.82 (s, 1H), 7.99 (d, 1H, J=8.8 Hz), 7.96 (d, 1H, J=2.0 Hz), 7.52 (d, 1H, J=2.0 Hz), 7.42 (dd, 1H, J=2.0, 8.0 Hz), 7.35 (dd, 1H, J=2.4, 8.8 Hz), 6.91 (d, 1H, J=8.8 Hz), 4.07 (q, 2H, J=6.8 Hz), 1.33 (t, 3H, J=6.8 Hz); $^{13}$C NMR (100 MHz, DMSO-$d_6$) δ 170.5, 155.2, 151.3, 147.9, 133.6, 131.8, 125.5, 124.6, 124.0, 122.3, 122.1, 116.7, 112.0, 64.7, 15.3.

Example 8-6

Synthesis of 5-(5-chlorobenzo[d]thiazol-2-yl)-2-methoxyphenol (Compound 87)

White solid; a reaction time of 4 hours; a yield of 24.1%; a melting point of 158.2 to 158.6° C.; $^1$H NMR (400 MHz, DMSO-$d_6$) δ 9.56 (s, 1H), 8.07 (d, 1H, J=8.8 Hz), 8.02 (d, 1H, J=2.0 Hz), 7.49 (d, 1H, J=2.4 Hz), 7.46 (dd, 1H, J=2.4, 8.4 Hz), 7.41 (dd, 1H, J=2.0, 8.4 Hz), 7.04 (d, 1H, J=8.8 Hz), 3.81 (s, 3H); $^{13}$C NMR (100 MHz, DMSO-$d_6$) δ 170.3, 155.3, 151.6, 147.7, 133.7, 131.9, 125.9, 125.7, 124.3, 122.5, 120.0, 114.3, 113.0, 56.4.

Example 8-7

Synthesis of 5-chloro-2-(4-methoxyphenyl)benzo[d]thiazole (Compound 88)

Brownish gold-colored crystal; a reaction time of 30 min; a yield of 20.2%; a melting point of 150.3 to 151.0° C.; $^1$H NMR (400 MHz, DMSO-$d_6$) δ 8.08 (d, 1H, J=8.4 Hz), 8.01 (d, 1H, J=2.0 Hz), 7.97 (d, 2H, J=8.8 Hz), 7.40 (dd, 1H, J=2.0, 8.8 Hz), 7.06 (d, 2H, J=8.8 Hz), 3.97 (s, 3H); $^{13}$C NMR (100 MHz, DMSO-$d_6$) δ170.1, 162.8, 155.3, 133.7, 131.9, 129.7, 125.8, 124.5, 124.4, 122.5, 115.5, 56.2.

Example 8-8

Synthesis of 5-chloro-2-(3,4-dimethoxyphenyl)benzo[d]thiazole (Compound 89)

White solid; a reaction time of 5 hours; a yield of 19.1%; a melting point of 165.2 to 167.1° C.; $^1$H NMR (500 MHz, DMSO-$d_6$) δ 8.12 (d, 1H, J=8.5 Hz), 8.08 (s, 1H), 7.61 (d, 1H, J=7.5 Hz), 7.60 (s, 1H), 7.46 (d, 1H, J=8.5 Hz), 7.12 (d, 1H, J=7.5 Hz), 3.87 (s, 3H), 3.84 (s, 3H); $^{13}$C NMR (100 MHz, DMSO-$d_6$) δ 170.3, 155.2, 152.6, 149.8, 133.7, 131.9, 125.9, 125.9, 124.3, 122.5, 121.8, 112.6, 110.1, 56.4, 56.3.

Example 8-9

Synthesis of 5-(5-chlorobenzo[d]thiazol-2-yl)benzene-1,3-diol (Compound 90)

In an acetic acid (0.6 mL) solvent, a mixture including 2-amino-4-chlorobenzenethiol (100 mg, 0.44 mmol), 3,5-dihydroxybenzaldehyde (60 mg, 0.44 mmol), and sodium acetate (107 mg, 1.30 mmol) was refluxed for 7 hours. After cooling, the reaction mixture was distributed between ethyl acetate and water, and an organic layer was dried by using MgSO$_4$, filtered, and evaporated under reduced pressure. The residual was purified by silica gel column chromatography using hexane and ethyl acetate (2:1) as a developer to obtain a solid Compound 90 (64.2 mg, 34.7%).

Light chololet-color; a reaction time of 7 hours; a yield of 34.7%; a melting point of 129.6 to 130.6° C.; $^1$H NMR (400 MHz, DMSO-$d_6$) δ 9.74 (s, 2H), 8.11 (d, 1H, J=8.4 Hz), 8.07 (d, 1H, J=2.0 Hz), 7.45 (dd, 1H, J=2.4, 8.4 Hz), 6.93 (d, 2H, J=2.0 Hz), 6.38 (d, 1H, J=2.4 Hz); $^{13}$C NMR (100 MHz, DMSO-$d_6$) δ 170.6, 159.8, 155.0, 134.7, 133.7, 132.0, 126.2, 124.4, 122.9, 106.5, 105.9.

Example 8-10

Synthesis of 5-chloro-2-(2,4-dimethoxyphenyl)benzo[d]thiazole (Compound 91)

Bluish green; a reaction time of 6 hours; a yield of 11.2%; a melting point of 138.6 to 140.3° C.; $^1$H NMR (400 MHz, DMSO-$d_6$) δ 8.30 (d, 1H, J=8.8 Hz), 8.06 (d, 1H, J=8.4 Hz), 7.99 (d, 1H, J=1.6 Hz), 7.37 (dd, 1H, J=2.0, 8.4 Hz), 6.77 (d, 1H, J=2.0 Hz), 6.72 (dd, 1H, J=2.0, 8.8 Hz), 4.01 (s, 3H), 3.84 (s, 3H); $^{13}$C NMR (100 MHz, DMSO-$d_6$) δ 165.2, 163.9, 159.3, 153.3, 134.3, 131.5, 130.7, 125.1, 123.8, 121.9, 114.6, 107.8, 99.2, 56.8, 56.4.

Example 8-11

Synthesis of 2-(5-chlorobenzo[d]thiazol-2-yl)phenol (Compound 92)

Shining white solid; a reaction time of 8 hours; a yield of 8.4%; a melting point of 194.2 to 195.7° C.; $^1$H NMR (400 MHz, CDCl$_3$) δ 12.22 (s, 1H), 7.96 (s, 1H), 7.79 (d, 1H, J=8.0 Hz), 7.66 (d, 1H, J=8.0 Hz), 7.44-7.35 (m, 2H), 7.09 (d, 1H, J=8.4 Hz), 6.95 (t, 1H, J=7.6 Hz); $^{13}$C NMR (100 MHz, CDCl3) δ 171.4, 158.2, 153.0, 133.4, 133.0, 131.1, 128.7, 126.2, 122.4, 122.2, 119.9, 118.2, 116.7.

Example 8-12

Synthesis of 5-chloro-2-(3,4,5-trimethoxyphenyl)benzo[d]thiazole (Compound 93)

White solid; a reaction time of 7 hours; a yield of 29.0%; a melting point of 159.4 to 160.0° C.; $^1$H NMR (500 MHz, DMSO-$d_6$) δ 8.15 (d, 1H, J=9.0 Hz), 8.12 (d, 1H, J=2.0 Hz), 7.49 (dd, 1H, J=2.0, 8.5 Hz), 7.31 (s, 2H), 3.90 (s, 6H), 3.75 (s, 3H); $^{13}$C NMR (125 MHz, DMSO-$d_6$) δ 170.2, 155.1, 154.1, 141.3, 134.0, 132.1, 128.6, 126.2, 124.4, 122.8, 105.3, 60.9, 56.9.

Example 8-13

Synthesis of 4-(5-chloro-2,3-dihydrobenzo[d]thiazol-2-yl)-2,6-dimethoxyphenol (Compound 94)

White solid; a reaction time of 6 hours; a yield of 17.2%; a melting point of 155.8 to 158.6° C.; $^1$H NMR (500 MHz, DMSO-$d_6$) δ 8.51 (s, 1H), 7.16 (s, 1H), 6.94 (d, 1H, J=8.0 Hz), 6.78 (s, 2H), 6.56 (dd, 1H, J=2.0, 8.0 Hz), 6.51 (d, 1H, J=2.0 Hz), 6.47 (s, 1H), 3.92 (s, 6H); $^{13}$C NMR (100 MHz, DMSO-$d_6$) δ 149.8, 148.5, 136.5, 132.3, 130.3, 124.8, 122.5, 118.2, 108.0, 104.7, 71.1, 56.7.

Example 8-14

Synthesis of 2-bromo-4-(5-chlorobenzo[d]thiazol-2-yl)phenol (Compound 95)

In a dimethyl sulfoxide (DMSO) (2 mL) solvent, a solution including 3-bromo-4-hydroxybenzaldehyde (163.7 mg, 0.81 mmol) and 2-amino-4-chlorobenzenethiol (100 mg, 0.45 mmol) was refluxed for 1 hour. After cooling, the residual was distributed between ethyl acetate and water, and an organic layer was dried by using MgSO$_4$, filtered, and evaporated under reduced pressure. The resultant residual was added to water, and then, the precipitate was filtered and the filtered product was washed with water and methylene chloride to obtain a solid Compound 95 (46.4 mg, 17.6%).

Blueish green solid; a reaction time of 1 hours; a yield of 17.6%; a melting point of 226.0 to 228.1° C.; $^1$H NMR (400 MHz, DMSO-$d_6$) δ 11.11 (s, 1H), 8.11 (d, 1H, J=1.2 Hz), 8.04 (d, 1H, J=8.8 Hz), 7.97 (d, 1H, J=1.2 Hz), 7.82 (dd, 1H, J=1.6, 8.4 Hz), 7.38 (dd, 1H, J=1.2, 8.8 Hz), 7.06 (d, 1H, J=8.4 Hz);

$^{13}$C NMR (100 MHz, DMSO-d$_6$) δ 168.8, 158.0, 155.1, 133.7, 132.1, 132.0, 128.9, 125.8, 125.7, 124.2, 122.5, 117.5, 110.9.

Example 8-15

Synthesis of 2,6-dibromo-4-(5-chlorobenzo[d]thiazol-2-yl)phenol (Compound 96)

In a DMF (3 mL) solvent, a solution including 2-amino-4-chlorobenzenethiol (100 mg, 0.63 mmol) and 3,5-dibromo-4-hydroxybenzaldehyde (127 mg, 0.63 mmol) was heated at a temperature of 100° C. for 8.5 hours. After DMF was evaporated therefrom, the residual was purified by silica gel column chromatography using hexane and ethyl acetate (5:1) as a developer to obtain a solid Compound 96 (34.3 mg, 18.1%).

A reaction time of 8.5 hours; a yield of 18.1%; $^1$H NMR (400 MHz, DMSO-d$_6$) δ 10.85 (s, 1H), 8.16 (m, 3H), 8.08 (br s, 1H), 7.47 (br s, 1H) $^{13}$C NMR (100 MHz, DMSO-d$_6$) δ 167.3, 154.9, 154.5, 134.0, 132.2, 131.6, 127.3, 126.3, 124.6, 122.8, 113.1

Example 9

Synthesis of Compounds 97a to 97d

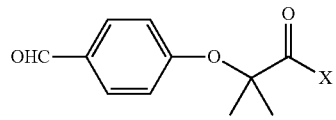

97a: X = OEt
97c: X = OH

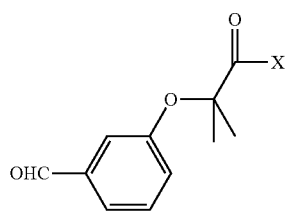

97b: X = OEt
97d: X = OH

Example 9-1

Synthesis of ethyl 2-(4-formylphenoxy)-2-methylpropanoate (Compound 97a)

In an ethanol solvent, 1 N ethoxy sodium (NaOEt) (1.1 eq.) was added dropwise to 4-hydroxybenzaldehyde (1.0 eq.) and ethyl α-bromoisobutyrate (1.1 eq.), and the reaction mixture was refluxed. After the ethanol was evaporated, the residual was distributed between ethyl acetate and water, and an organic layer was dried by using MgSO$_4$, filtered, and evaporated. The residual was purified by silica gel column chromatography using hexane and ethyl acetate (8:1) to obtain Compound 97a.

A reaction time of 12.5 hours; a yield of 41.9%; $^1$H NMR (400 MHz, DMSO-d$_6$) δ 9.70 (s, 1H), 7.62 (d, 2H, J=8.8 Hz), 6.73 (d, 2H, J=8.8 Hz), 4.05 (q, 2H, J=6.8 Hz), 1.50 (s, 6H), 1.03 (t, 3H, J=7.2 Hz); $^{13}$C NMR (100 MHz, DMSO-d$_6$) δ 190.7, 173.4, 161.0, 131.6, 130.4, 117.8, 79.6, 61.7, 25.4, 14.0.

Example 9-2

Synthesis of ethyl 2-(3-formylphenoxy)-2-methylpropanoate (Compound 97b)

In an ethanol solvent, 1 N ethoxy sodium (NaOEt) (1.1 eq.) was added dropwise to 3-hydroxybenzaldehyde (1.0 eq.) and ethyl α-bromoisobutyrate (1.1 eq.), and the reaction mixture was refluxed. After the ethanol was evaporated, the residual was distributed between ethyl acetate and water, and an organic layer was dried by using MgSO$_4$, filtered, and evaporated. The residual was purified by silica gel column chromatography using hexane and ethyl acetate (8:1) to obtain Compound 97b.

A reaction time of 22 hours; a yield of 59.0%; $^1$H NMR (400 MHz, DMSO-d$_6$) δ 9.92 (s, 1H), 7.52 (dd, 1H, J=1.2, 7.2 Hz), 7.47 (t, 1H, J=8.0 Hz), 7.23 (m, 1H), 7.11 (m, 1H), 4.13 (q, 2H, J=7.2 Hz), 1.52 (s, 6H), 1.11 (t, 3H, J=7.2 Hz); $^{13}$C NMR (100 MHz, DMSO-d$_6$) δ 193.3, 173.5, 156.3, 138.1, 130.9, 125.6, 124.4, 118.1, 79.7, 61.8, 25.5, 14.4.

Example 9-3

Synthesis of ethyl 2-(4-formylphenoxy)-2-methylpropanoic acid (Compound 97c)

The obtained Compound 97a (1.0 eq.) was dissolved in 1,4-dioxane, and 1 N NaOH (1.4 eq.) was added thereto. The reaction mixture was stirred at room temperature, and after a volatile material was evaporated, the residual was distributed between methylene chloride and water. An water layer was acidified by using a 12 N HCl and extracted by using methylene chloride. An organic layer was evaporated to obtain Compound 97c.

A reaction time of 4 hours; a yield of 99%; $^1$H NMR (500 MHz, DMSO-d$_6$) δ 10.54 (s, 1H), 9.83 (s, 1H), 7.79 (dd, 2H, J=9.0 Hz), 6.95 (d, 2H, J=8.5 Hz), 1.69 (s, 6H); $^{13}$C NMR (100 MHz, DMSO-d$_6$) δ 191.7, 178.5, 161.0, 132.0, 130.5, 118.5, 79.5, 25.5.

Example 9-4

Synthesis of 2-(3-formylphenoxy)-2-methylpropanoic acid (Compound 97d)

The obtained Compound 97b (1.0 eq.) was dissolved in 1,4-dioxane, and 1 N NaOH (1.4 eq.) was added thereto. The reaction mixture was stirred at room temperature, and after a volatile material was evaporated, the residual was distributed between methylene chloride and water. An aqueous layer was acidified by using a 12 N HCl and extracted by using methylene chloride. An organic layer was evaporated to obtain Compound 97d.

A reaction time of 7.5 hours; a yield of 95.0%; $^1$H NMR (400 MHz, DMSO-d$_6$) δ 9.91 (s, 1H), 7.52 (d, 1H, J=7.2 Hz), 7.41 (t, 1H, J=8.0 Hz), 7.38 (br s, 1H), 7.18 (dd, 1H, J=1.6, 8.0

Hz), 1.63 (s, 6H); $^{13}$C NMR (100 MHz, DMSO-d$_6$) δ 192.4, 179.1, 155.9, 137.8, 130.2, 126.4, 124.9, 119.8, 79.7, 25.4.
Example 10
Synthesis of Compounds 97 to 106
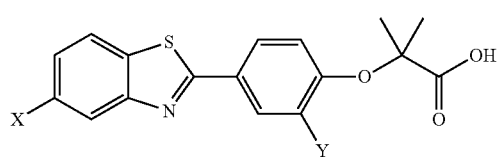
97: X = H, Y = H
98: X = CF$_3$, Y = H
99: X = Cl, Y = H
122: X = H, Y = OMe
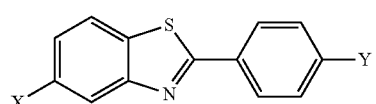
107: X = H, Y = OBn
108: X = CF$_3$, Y = OBn
109: X = Cl, Y = OBn
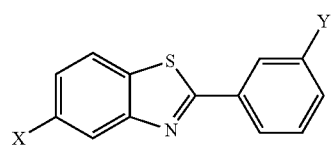
110: X = H, Y = OBn
111: X = CF$_3$, Y = OBn
112: X = Cl, Y = OBn
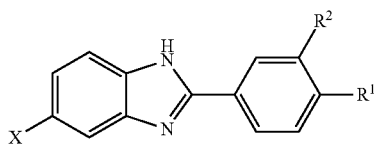
113: X = COOH, R$^1$ = OBn, R$^2$ = H
114: X = H, R$^1$ = OBn, R$^2$ = H
115: X = H, R$^1$ = H, R$^2$ = OBn
125: X = COOH, R$^1$ = H, R$^2$ = OBn
116
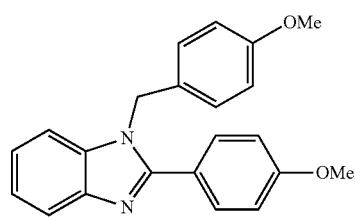
117, 118: X = NH, Y = H
120: X = S, Y = H
121: X = S, Y = Cl
119
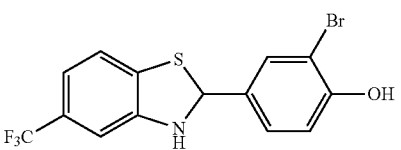
126
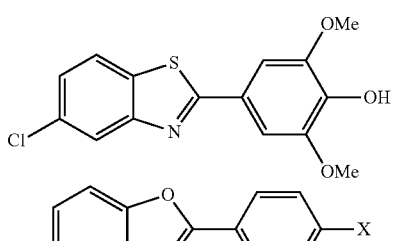
123: X = OH
124: X = OMe
100
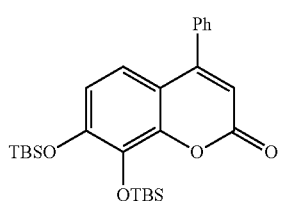
101
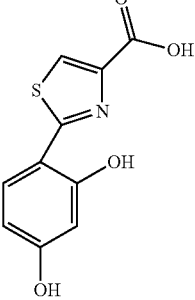
102
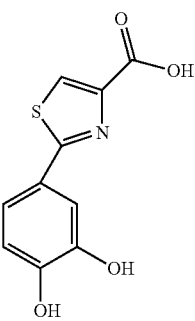
103
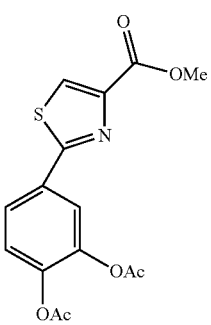

-continued

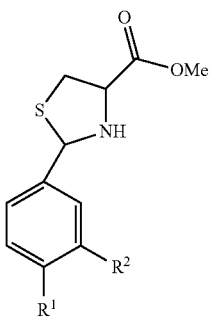

104: R¹ = OH, R² = OH
105: R¹ = OAc, R² = OAc

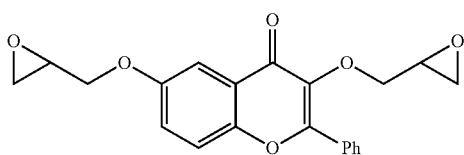

106

Example 10-1

Synthesis of 2-(4-(benzo[d]thiazol-2-yl)phenoxy)-2-methylpropanoic acid (Compound 97)

In a methanol solvent, a solution including Compound 97c (1.0 eq.) and 2-aminothiophenol (1.0 eq.) was stirred at room temperature. After methanol was removed, the precipitate was filtered, and washed with cold methanol to obtain a solid target product.

White solid; a reaction time of 17 hours; a yield of 40.3%; a melting point of 200.3 to 201.5° C.; $^1$H NMR (400 MHz, DMSO-d$_6$) δ 8.05 (d, 1H, J=8.0 Hz), 7.98-7.95 (m, 3H), 7.47 (td, 1H, J=1.2, 8.4 Hz), 7.38 (td, 1H, J=1.2, 8.4 Hz), 6.94 (d, 2H, J=8.8 Hz), 1.56 (s, 6H); $^{13}$C NMR (100 MHz, DMSO-d$_6$) δ 175.3, 167.6, 158.8, 154.3, 135.0, 129.3, 127.2, 126.7, 125.8, 123.2, 122.9, 118.9, 79.5, 25.8.

Example 10-2

Synthesis of 2-methyl-2-(4-(5-(trifluoromethyl)benzo[d]thiazol-2-yl)phenoxy)propanoic acid (Compound 98)

A solution including Compound 97c (1.0 eq.) and 2-amino-4-trifluoromethylbenzenethiol (1.0 eq.) was stirred in a methanol solvent at room temperature. After methanol was removed, the precipitate was filtered, and washed with cold methanol to obtain a solid target product.

White solid; a reaction time of 4 hours; a yield of 31.5% melting point, 97.3 to 98.5° C.; $^1$H NMR (400 MHz, CDCl$_3$) δ 8.24 (d, 1H, J=0.8 Hz), 7.94 (d, 2H, J=8.8 Hz), 7.90 (dd, 1H, J=0.8, 8.4 Hz), 7.53 (dd, 1H, J=1.2, 8.4 Hz), 6.88 (d, 2H, J=9.2 Hz), 1.65 (s, 6H); $^{13}$C NMR (100 MHz, CDCl$_3$) δ 174.5, 169.8, 158.7, 154.0, 138.5, 129.2, 129.1 (q, J=32.6 Hz), 126.9, 124.5 (q, J=270.9 Hz), 122.3, 121.4, 120.2, 118.8, 79.7, 25.6.

Example 10-3

Synthesis of 2-(4-(5-chlorobenzo[d]thiazol-2-yl)phenoxy)-2-methylpropanoic acid (Compound 99)

In an acetic acid (0.37 mL) solvent, a mixture including Compound 97c (78.2 mg, 0.38 mmol), 2-amino-4-chlorobenzenethiol (60.0 mg, 0.38 mmol), and sodium acetate (NaOAc) (93.6 mg, 1.13 mmol) was refluxed for 1 hour. After cooling, the reaction mixture was distributed between ethyl acetate and water, and an organic layer was evaporated under reduced pressure. The produced precipitate was filtered, and washed with methylene chloride to obtain Compound 99 (46.6 mg, 39.6%).

White solid; a reaction time of 1 hours; a yield of 39.6%; a melting point of 190.8 to 192.0° C.; $^1$H NMR (400 MHz, DMSO-d$_6$) δ 8.03 (d, 1H, J=8.4 Hz), 7.98 (d, 1H, J=2.0 Hz), 7.92 (d, 2H, J=8.8 Hz), 7.37 (dd, 1H, J=2.0, 8.8 Hz), 6.92 (d, 2H, J=8.8 Hz), 1.55 (s, 6H); $^{13}$C NMR (100 MHz, DMSO-d$_6$) δ 175.2, 169.8, 159.0, 155.2, 133.7, 131.9, 129.4, 126.3, 125.8, 124.2, 122.5, 118.9, 79.5, 25.8.

Example 10-4

Synthesis of 7,8-bis(tert-butyldimethylsilyloxy)-4-phenyl-2H-chromen-2-one (Compound 100)

In a methylene chloride (4 mL) solvent, tert-butyldimethylsilylchloride (TBSCl) (144.6 mg, 0.96 mmol) was added to a solution including 7,8-dihydroxy-4-phenylcoumarin (81.3 mg, 0.32 mmol) and imidazole (130.6 mg, 1.92 mmol), and the reaction mixture was stirred at room temperature for 6 hours. The reaction mixture was distributed between methylene chloride and water, and an organic layer was evaporated under reduced pressure, filtered, and evaporated. The residual was purified by silica gel column chromatography using hexane and ethyl acetate (15:1) to obtain Compound 100 (149.6 mg, 97%).

$^1$H NMR (400 MHz, CDCl$_3$) δ 7.43 (m, 5H), 6.93 (d, 1H, J=8.8 Hz), 6.73 (d, 1H, J=8.8 Hz), 6.17 (s, 1H), 1.08 (s, 9H), 0.98 (s, 9H), 0.29 (s, 6H), 0.25 (s, 6H); $^{13}$C NMR (100 MHz, CDCl$_3$) δ 160.6, 156.1, 150.7, 147.6, 136.0, 135.2, 129.7, 128.9, 128.7, 119.0, 116.9, 114.1, 112.4, 26.2, 18.9, 18.9, −3.5.

Example 10-5

Synthesis of 2-(2,4-dihydroxyphenyl)thiazole-4-carboxylic acid](Compound 101)

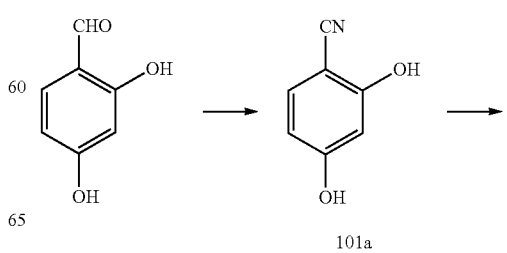

101a

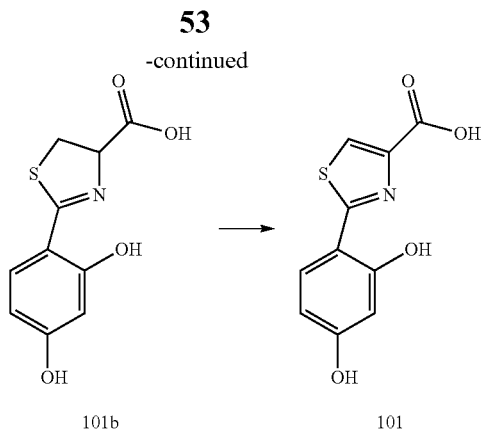

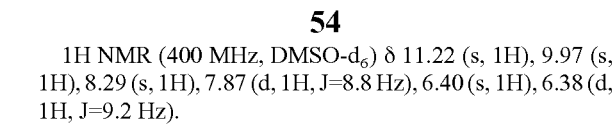

1) Synthesis of 2,4-dihydroxybenzonitrile (Compound 101a)

In an acetic acid (10 mL) solvent, a solution including 2,3-dihydroxybenzaldehyde (3.0 g, 21.7 mmol), sodium acetate (NaOAc) (3.54 g, 43.4 mmol), and nitroethane (3.24 g, 43.4 mmol) was refluxed for 8 hours. After cooling, the reaction mixture was distributed between ethyl acetate and water. Until a pH of the residual aqueous layer reached 8, an organic layer was washed with a saturated NaHCO₃ solution. The organic layer was evaporated, the residual was purified by silica gel column chromatography using hexane and ethyl acetate (2:1) as a developer to obtain Compound 101a (1.88 g, 59%).

A melting point of 183 to 186° C.; $^1$H NMR (400 MHz, DMSO-$d_6$) δ 10.76 (br s, 1H), 10.33 (br s, 1H), 7.33 (d, 1H, J=8.4 Hz), 6.38 (d, 1H, J=2.0 Hz), 6.28 (dd, 1H, J=2.0, 8.4 Hz).

2) Synthesis of 2-(2,4-dihydroxyphenyl)-4,5-dihydrothiazole-4-carboxylic acid] (Compound 101b)

In a mixed solvent including methanol (30 mL) and phosphate buffer solution (20 mL), NaHCO₃ (466 mg, 5.55 mmol) was carefully added to a solution including the obtained Compound 101a (0.5 g, 3.70 mmol) and L-cysteine hydrochloride monohydrate (974 mg, 5.55 mmol), and the reaction mixture was refluxed for 10 hours. After methanol was evaporated, the reaction mixture was acidified by using 1 N HCl to increase a pH to 2. The resultant precipitate was filtered, and washed with water to obtain Compound 101b (613 mg, 69%).

A melting point of 269 to 270° C.; $^1$H NMR (400 MHz, DMSO-$d_6$) δ 10.25 (br s, 1H), 7.21 (d, 1H, J=8.4 Hz), 6.34 (d, 1H, J=8.8 Hz), 6.27 (s, 1H), 5.34 (t, 1H, J=6.8 Hz), 3.64-3.51 (m, 2H).

3) Synthesis of 2-(2,4-Dihydroxyphenyl)thiazole-4-carboxylic acid (Compound 101)

In a DMF (5 mL) solvent, a suspension of Compound 101b (100 mg, 0.41 mmol) and MnO₂ (640 mg, 6.26 mmol) was stirred at room temperature for 24 hours. After DMF was evaporated, 1 N a NaOH solution (0.5 mL) was added to the residual. The reaction mixture was filtered, washed with water, and the filtrate was acidified by using 1 N HCl to increase a pH to 2. The produced precipitate was filtered, and washed with cold water to obtain Compound 101 (46.2 mg, 43%).

1H NMR (400 MHz, DMSO-$d_6$) δ 11.22 (s, 1H), 9.97 (s, 1H), 8.29 (s, 1H), 7.87 (d, 1H, J=8.8 Hz), 6.40 (s, 1H), 6.38 (d, 1H, J=9.2 Hz).

Example 10-6

Synthesis of (4R)-2-(3,4-dihydroxyphenyl)-4,5-dihydrothiazole-4-carboxylic acid (Compound 102)

Compound 102 was synthesized in such a manner that is similar to that used in synthesizing Compound 101b.

A reaction time of 12 hours; a yield of 20%; a melting point of 178-179° C.; $^1$H NMR (400 MHz, DMSO-$d_6$) δ 7.24 (d, 1H, J=2.0 Hz), 7.00 (dd, 1H, J=2.0, 8.4 Hz), 6.74 (d, 1H, J=8.4 Hz), 4.96 (t, 1H, J=8.8 Hz), 3.49 (d, 2H, J=9.2 Hz); $^{13}$C NMR (100 MHz, DMSO-$d_6$) δ 173.3, 167.5, 149.6, 145.9, 124.7, 121.3, 116.1, 115.7, 79.9, 35.7.

Example 10-7

Synthesis of Compounds 103 to 105

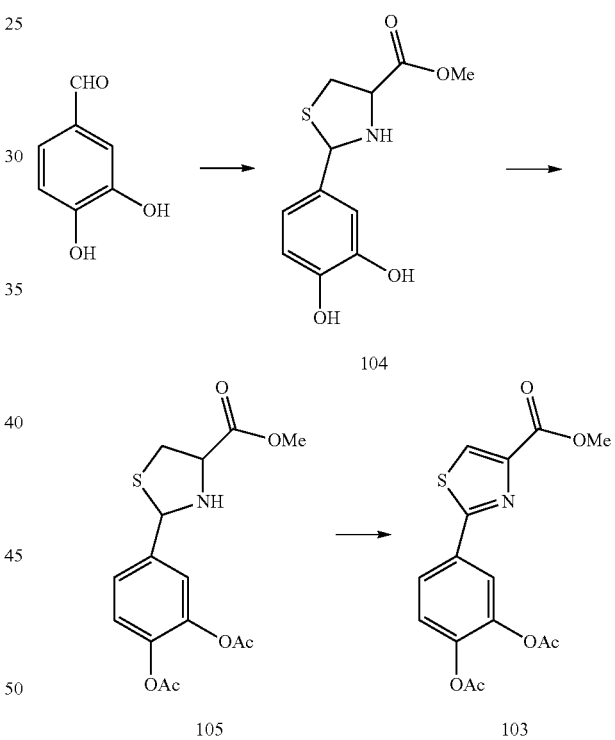

1) Synthesis of (2R/S,4R)-methyl 2-(3,4-dihydroxyphenyl)thiazolidine-4-carboxylate (Compound 104)

In a co-solvent of ethanol (5 mL) and water (5 mL), a solution including NaHCO₃ (486 mg, 5.79 mmol), 3,4-dihydroxybenzaldhehyde (3,4-dihydroxybenzaldehyde) (800 mg, 5.80 mmol), and L-cysteine methyl ester hydrochloride (1.0 g, 5.84 mmol) was stirred at room temperature for 5 hours. After ethanol was evaporated, the reaction mixture was distributed between ethyl acetate and water, and an organic layer was dried, filtered, and evaporated. The residual was purified by silica gel column chromatography using hexane and ethyl acetate (4:1) to obtain a solid Compound 104 (1.23 g, 83%).

A melting point of 116 to 118° C.; $^1$H NMR (400 MHz, CD$_3$OD) δ 6.96-6.93 (m, 2H), 6.85-6.80 (m, 2H), 6.73 (d, 1H, J=8.4 Hz), 6.71 (d, 1H, J=8.0 Hz), 5.49 (s, 1H), 5.34 (s, 1H), 4.39 (dd, 1H, J=3.6, 7.2 Hz), 3.96 (t, 1H, J=8.4 Hz), 3.76 (s, 3H), 3.73 (s, 3H), 3.39 (dd, 1H, J=7.2, 10.4 Hz), 3.36 (dd, 1H, J=7.2, 10.8 Hz), 3.26 (dd, 1H, J=3.6, 10.8 Hz), 3.11 (dd, 1H, J=8.4, 10.0 Hz); $^{13}$C NMR (100 MHz, CD$_3$OD) δ 172.7, 171.9, 145.7, 145.6, 145.3, 145.1, 131.2, 129.5, 119.0, 118.9, 115.1, 114.9, 114.5, 114.3, 71.7, 71.0, 65.0, 64.6, 51.9, 51.7, 38.0, 37.3.

2) Synthesis of 4-((2R/S,4R)-4-(methoxycarbonyl)thiazolidin-2-yl)-1,2-phenylene diacetate (Compound 105)

In a methylene chloride (75 mL) solvent, an anhydrous acetic acid (0.89 mL, 9.60 mmol) was added dropwise to a solution including Compound 104 (1.23 g, 4.83 mmol) and triethylamine (Et$_3$N) (1.35 mL, 9.62 mmol), and the reaction mixture was stirred at room temperature for 4 hours. After volatile materials evaporate, the residual was distributed between ethyl acetate and water, and an organic layer was dried, filtered, and evaporated. The residual was purified by silica gel column chromatography using hexane and ethyl acetate (4:1) to obtain a solid Compound 105 (1.214 g, 75.1%).

$^1$H NMR (500 MHz, CDCl$_3$) δ 7.44-7.37 (m, 4H), 7.20 (d, 1H, J=8.0 Hz), 7.14 (d, 1H, J=8.5 Hz), 5.82 (s, 1H), 5.54 (s, 1H), 4.10 (t, 1H, J=7.0 Hz), 3.98 (dd, 1H, J=7.5, 8.5 Hz), 3.80 (s, 3H), 3.79 (s, 3H), 3.45 (dd, 1H, J=7.0, 10.0 Hz), 3.36 (dd, 1H, J=7.0, 10.5 Hz), 3.14 (dd, 1H, J=6.5, 10.5 Hz), 3.09 (dd, 1H, J=9.5, 10.5 Hz), 2.30 (s, 3H), 2.29 (s, 3H), 2.28 (s, 3H), 2.28 (s, 3H); $^{13}$C NMR (100 MHz, CDCl$_3$) δ 172.3, 171.6, 168.4, 168.4, 168.3, 168.3, 142.4, 142.3, 142.0, 141.7, 140.8, 137.3, 126.1, 125.5, 124.6, 124.5, 123.8, 123.4, 123.0, 122.3, 71.8, 69.9, 65.7, 64.2, 52.8, 52.8, 39.3, 38.2, 20.9, 20.8.

3) Synthesis of 4-(4-(Methoxycarbonyl)thiazol-2-yl)-1,2-phenylene diacetate (Compound 103)

In a CCl$_4$ (5 mL) solvent, NBS (N-bromosuccinimide) (10.6 mg, 0.06 mmol) and AIBN (2,2'-azobis(2-methylpropionitrile)) (3.0 mg) were added to a solution of Compound 105 (11.2 mg, 0.03 mmol), and the reaction mixture was refluxed for 5 hours. After volatile materials evaporate, the residual was distributed between ethyl acetate and water, and an organic layer was dried, filtered, and evaporated. The residual was purified by silica gel column chromatography using hexane and ethyl acetate (4:1) to obtain a solid Compound 103 (3.0 mg, 33%).

A melting point of 137 to 138° C.; $^1$H NMR (500 MHz, CDCl$_3$) δ 8.19 (s, 1H), 7.90 (d, 1H, J=2.5 Hz), 7.87 (dd, 1H, J=2.0, 8.5 Hz), 7.31 (d, 1H, J=8.5 Hz), 3.98 (s, 3H), 2.33 (s, 3H), 2.32 (s, 3H); $^{13}$C NMR (100 MHz, CDCl$_3$) δ 168.2, 168.1, 167.1, 162.0, 148.1, 144.3, 142.8, 131.6, 127.9, 125.3, 124.3, 122.3, 52.8, 20.9, 20.8.

Example 10-8

Synthesis of 3,6-bis((oxiran-2-yl)methoxy)-2-phenyl-4H-chromen-4-one (Compound 106)

In a DMF (4 mL) solvent, potassium carbonate (180.2 mg, 1.30 mmol) and epichlorohydrin (0.2 mL, 2.17 mmol) were added to a 3,6-dihydroxyflavone (3,6-dihydroxyflavone) (110.5 mg, 0.43 mmol) solution. After stirring at a temperature of 70° C. for 8 hours, an ammonium chloride aqueous solution was added to the reaction mixture. The reaction mixture was distributed between diethyl ether and water, and an organic layer was dried by using anhydrous MgSO$_4$, filtered, and evaporated under reduced pressure. The residual was purified by silica gel column chromatography using hexane and ethyl acetate (1:1.5) as a developer to obtain Compound 106 (25.3 mg, 16%) that is a white solid bis-oxyranyl flavone.

A reaction time of 8 hours; a yield of 16%; a melting point of 90.6 to 91.1° C.; $^1$H NMR (500 MHz, CDCl$_3$) δ 8.13-8.11 (m, 2H), 7.59 (d, 1H, J=3.0 Hz), 7.55-7.51 (m, 3H), 7.50 (d, 1H, J=9.0 Hz), 7.34 (dd, 1H, J=3.0, 9.5 Hz), 4.43-4.39 (m, 2H), 4.03-3.98 (m, 2H), 3.43-3.40 (m, 1H), 3.28-3.26 (m, 1H), 2.94 (t, 1H, J=4.5 Hz), 2.80 (dd, 1H, J=2.5, 4.5 Hz), 2.76 (t, 1H, J=4.5 Hz), 2.58 (dd, 1H, J=2.5, 5.0 Hz); $^{13}$C NMR (100 MHz, CDCl$_3$) δ 174.78, 156.04, 155.75, 150.68, 140.03, 131.07, 128.95, 128.71, 124.87, 124.51, 119.92, 105.60, 87.13, 73.69, 69.60, 50.66, 50.13, 44.74, 44.61; LRMS (FAB+) m/z 367 (M+H)$^+$; HRMS (FAB+) m/z C$_{21}$H$_{19}$O$_6$ (M+H)$^+$ calcd 367.1182, obsd 367.1184.

Example 11

Synthesis of Compounds 107 to 112

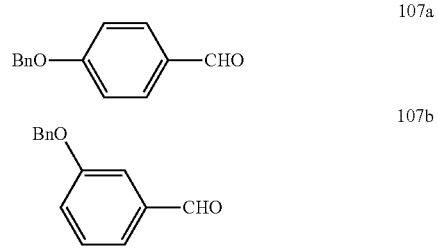

1) Synthesis of 4-(benzyloxy)benzaldehyde (Compound 107a)

In an acetonitrile (30 mL) solvent, benzyl bromide (1.95 mL, 16.40 mmol) was added to a solution including 4-hydroxybenzaldehyde (2.0 g, 16.38 mmol) and potassium carbonate (3.40 g, 24.60 mmol), and then, the reaction mixture was refluxed for 1.5 hours. After cooling, the reaction mixture was distributed between methylene chloride and water. An organic layer was dried by using MgSO$_4$, and filtered. A filtrate was evaporated, and water was added to the resultant solid. The solid was filtered and washed with water to obtain 4-(benzyloxy)benzaldehyde (3.082 g, 88.7%).

1H NMR (400 MHz, CDCl$_3$) δ 9.87 (s, 1H), 7.82 (d, 2H, J=9.2 Hz), 7.43-7.34 (m, 5H), 7.06 (d, 2H, J=8.8 Hz), 5.14 (s, 2H); $^{13}$C NMR (100 MHz, CDCl$_3$) δ 191.0, 164.0, 136.1, 132.2, 130.3, 129.0, 128.6, 127.7, 115.4, 70.5.

2) Synthesis of 3-(benzyloxy)benzaldehyde (Compound 107b)

In an acetonitrile (50 mL) solvent, benzyl bromide (4.6 mL, 38.68 mmol) was added to a solution including 3-hydroxybenzaldehyde (5.0 g, 40.94 mmol) and potassium carbonate (8.49 g, 61.43 mmol), and the reaction mixture was refluxed for 3 hours. After cooling, the reaction mixture was distributed between methylene chloride and water. An organic layer was dried by using MgSO$_4$, and filtered. A filtrate was evaporated, and water was added to the resultant solid. The solid was filtered and washed with water to obtain Compound 107b.

$^1$H NMR (500 MHz, DMSO-$d_6$) δ 9.97 (s, 1H), 7.54-7.51 (m, 3H), 7.47 (d, 2H, J=7.5 Hz), 7.40 (t, 2H, J=7.0 Hz), 7.37-7.32 (m, 2H), 5.19 (s, 2H); $^{13}$C NMR (100 MHz, DMSO-$d_6$) δ 193.6, 159.5, 138.3, 137.3, 131.1, 129.1, 128.6, 128.4, 123.4, 122.4, 114.6, 70.1.

3) Synthesis of Compounds 107 to 112

In a methanol solvent, a solution including Compound 107a (1.0 eq.) or Compound 107b (1.0 eq.) and 2-aminothiophenol analog (1.0 eq.) was stirred at room temperature. After methanol was removed, the produced precipitate was filtered and the resultant product was washed with cold methanol to obtain solid Compounds 108 through 111. In the case of Compounds 107 and 112, silica gel column chromatography using hexane and ethyl acetate (20:1) were performed thereon for the purification to obtain solid Compound 107 and Compound 112

Example 11-1

Synthesis of 2-(4-(benzyloxy)phenyl)benzo[d]thiazole (Compound 107)

Yellowish white; a reaction time of 16 hours; a yield of 19.3%; a melting point of 166.1 to 167.2° C.; $^1$H NMR (400 MHz, DMSO-$d_6$) δ 8.08-7.96 (m, 4H), 7.48-7.24 (m, 7H), 7.16 (d, 2H, J=7.6 Hz), 5.18 (s, 2H); $^{13}$C NMR (100 MHz, DMSO-$d_6$) δ 167.7, 161.5, 154.3, 137.3, 134.9, 129.6, 129.2, 128.7, 128.5, 127.2, 126.4, 125.8, 123.1, 122.9, 116.3, 70.2.

Example 11-2

Synthesis of 2-(4-(benzyloxy)phenyl)-5-(trifluoromethyl)benzo[d]thiazole (Compound 108)

White solid; a reaction time of 19 hours; a yield of 57.7%; a melting point of 194.3 to 195.1° C.; $^1$H NMR (500 MHz, CDCl$_3$) δ 8.29 (s, 1H), 8.05 (d, 2H, J=8.5 Hz), 7.98 (d, 1H, J=8.5 Hz), 7.59 (d, 1H, J=8.0 Hz), 7.47 (d, 2H, J=7.0 Hz), 7.42 (t, 2H, J=7.5 Hz), 7.36 (t, 1H, J=7.5 Hz), 7.10 (d, 2H, J=9.0 Hz), 5.17 (s, 2H).

Example 11-3

Synthesis of 2-(4-(benzyloxy)phenyl)-5-chlorobenzo[d]thiazole (Compound 109)

Green solid; a reaction time of 4 hours; a yield of 49.8%; a melting point of 142.7 to 143.3° C.; $^1$H NMR (400 MHz, CDCl$_3$) δ 8.33 (s, 1H), 7.89 (d, 2H, J=8.4 Hz), 7.51 (d, 1H, J=8.4 Hz), 7.44 (d, 2H, J=7.2 Hz), 7.39 (t, 2H, J=7.2 Hz), 7.33 (t, 1H, J=6.8 Hz), 7.06 (d, 2H, J=8.8 Hz), 7.00 (d, 1H, J=2.4 Hz), 5.13 (s, 2H); $^{13}$C NMR (100 MHz, CDCl$_3$) δ 162.2, 160.4, 150.3, 136.5, 133.0, 131.4, 130.5, 129.1, 128.9, 128.4, 127.7, 127.6, 126.4, 117.7, 115.4, 70.4.

Example 11-4

Synthesis of 2-(3-(benzyloxy)phenyl)benzo[d]thiazole (Compound 110)

Ivory; a reaction time of 2 hours; a yield of 30.4%; a melting point of 121.5 to 122.1° C.; $^1$H NMR (400 MHz, CDCl$_3$) δ 8.08 (dd, 1H, J=1.2, 8.0 Hz), 7.89 (dd, 1H, J=1.2, 8.0 Hz), 7.77 (t, 1H, J=2.0 Hz), 7.66 (ddd, 1H, J=1.0, 2.0, 7.6 Hz), 7.51-7.45 (m, 3H), 7.43-7.34 (m, 5H), 7.10 (ddd, 1H, J=1.2, 2.8, 8.4 Hz), 5.16 (s, 2H); $^{13}$C NMR (100 MHz, CDCl$_3$) δ 168.1, 159.5, 154.3, 136.9, 135.3, 135.2, 130.3, 128.9, 128.4, 127.9, 126.6, 125.5, 123.5, 121.9, 120.7, 118.2, 113.5, 70.5.

Example 11-5

Synthesis of 2-(3-(Benzyloxy)phenyl)-5-(trifluoromethyl)benzo[d]thiazole (Compound 111)

Bright white solid; a reaction time of 4 hours; a yield of 46.6%; a melting point of 93.8 to 95.1° C.; $^1$H NMR (400 MHz, CDCl$_3$) δ 8.32 (s, 1H), 7.98 (d, 1H, J=8.4 Hz), 7.76 (t, 1H, J=2.0 Hz), 7.65 (d, 1H, J=8.0 Hz), 7.60 (d, 1H, J=8.4 Hz), 7.47 (d, 2H, J=7.2 Hz), 7.42-7.32 (m, 4H), 7.13 (dd, 1H, J=2.4, 8.4 Hz), 5.17 (s, 2H); $^{13}$C NMR (100 MHz, CDCl$_3$) δ 170.1, 159.5, 153.9, 136.7, 134.5, 134.5, 130.5, 129.0 (q, J=32.6 Hz), 128.9, 128.4, 127.8, 124.7 (q, J=270.4 Hz), 122.4, 121.8 (q, J=3.8 Hz), 120.8, 120.6 (q, J=3.7 Hz), 118.7, 113.6, 70.5.

Example 11-6

Synthesis of 2-(3-(benzyloxy)phenyl)-5-chlorobenzo[d]thiazole (Compound 112)

A reaction time of 22 hours; a yield of 7.4%; $^1$H NMR (500 MHz, DMSO-$d_6$) δ 8.06 (d, 1H, J=2.0 Hz), 7.81 (d, 1H, J=8.5 Hz), 7.75 (br s, 1H), 7.65 (d, 1H, J=7.5 Hz), 7.49 (d, 2H, J=7.5 Hz), 7.43-7.36 (m, 5H), 7.13 (dd, 1H, J=2.5, 8.5 Hz), 5.18 (s, 2H); $^{13}$C NMR (100 MHz, DMSO-$d_6$) δ 169.9, 159.5, 155.1, 136.8, 134.8, 133.6, 132.5, 130.4, 128.9, 128.4, 127.8, 125.9, 123.3, 122.5, 120.7, 118.5, 113.5, 70.5.

Example 12

Synthesis of Compounds 113 to 126

Compounds 113-115, 121, and 125 were synthesized as follows. That is, in a DMF solvent in the presence of Na$_2$S$_2$O$_5$, a solution including Compound 107a (0.9-1.4 eq., in the case of Compounds 113 and 114), Compound 107b (0.9-1.4 eq., in the case of Compounds 115 and 125) or Compound 97d (0.9-1.4 eq., in the case of Compound 121) and 3,4-diaminobenzoic acid (1.0 eq., in the case of Compounds 113 and 125), 1,2-phenylenediamine (1.0 eq., in the case of Compounds 114 and 115), or 4-chloro-2-aminobenzenethiol (1.0 eq., in the case of Compound 121) was heated to a temperature of 80° C. After DMF was evaporated, water was added to the reaction mixture, and a precipitate was filtered, and the resultant product was washed with water and a small amount of methylene chloride and/or ethyl acetate to obtain Compounds 113-115 and 125. In the case of Compound 121, DMF was evaporated therefrom, and the resultant solution was extracted with ethyl acetate, and an organic layer was condensed and the residual was purified twice by silica gel column chromatography using methylene chloride and methanol (10:1) and hexane and ethyl acetate (2:1) to obtain a solid Compound 121.

Synthesis methods of Compounds 116 to 120, 122 to 124, and 126 are different from the method described above, and thus, they are separably described below.

Example 12-1

Synthesis of 2-(4-(benzyloxy)phenyl)-1H-benzo[d]imidazole-5-carboxylic acid (Compound 113)

A reaction time of 6 hours; a yield of 99%; $^1$H NMR (500 MHz, DMSO-$d_6$) δ 12.63 (br s, 1H), 8.18 (s, 1H), 8.15 (d, 2H, J=9.5 Hz), 7.84 (d, 1H, J=8.5 Hz), 7.63 (d, 1H, J=8.0 Hz), 7.46 (d, 2H, J=7.0 Hz), 7.38 (t, 2H, J=7.5 Hz), 7.32 (t, 1H, J=7.0 Hz), 7.19 (d, 2H, J=8.5 Hz), 5.17 (s, 2H).

Example 12-2

Synthesis of 2-(4-(benzyloxy)phenyl)-1H-benzo[d]imidazole (Compound 114)

A reaction time of 5.5 hours; a yield of 82.1%; $^1$H NMR (400 MHz, DMSO-$d_6$) δ 8.09 (d, 2H, J=8.8 Hz), 7.52 (m, 2H), 7.44 (d, 1H, J=7.2 Hz), 7.37 (t, 1H, J=7.6 Hz), 7.30 (t, 1H, J=7.2 Hz), 7.16-7.12 (m, 4H), 5.15 (s, 2H); $^{13}$C NMR (100 MHz, DMSO-$d_6$) δ 160.4, 152.0, 144.3, 137.5, 129.1, 128.7, 128.6, 128.5, 123.6, 122.4, 119.1 115.9, 70.0.

Example 12-3

Synthesis of 2-(3-(Benzyloxy)phenyl)-1H-benzo[d]imidazole (Compound 115)

A reaction time of 3.3 hours; a yield of 58.2%; $^1$H NMR (400 MHz, DMSO-$d_6$) δ 7.83 (d, 1H, J=1.2 Hz), 7.75 (d, 1H, J=8.0 Hz), 7.64 (d, 1H, J=7.2 Hz), 7.51-7.36 (m, 7H), 7.31 (d, 1H, J=7.2 Hz), 7.17 (t, 1H, J=7.6 Hz), 7.10 (d, 1H, J=8.0 Hz), 5.18 (s, 2H); $^{13}$C NMR (100 MHz, DMSO-$d_6$) δ 159.4, 151.7, 114.4, 137.6, 135.6, 132.2, 130.8, 129.1, 128.6, 128.4, 123.3, 122.4, 119.7, 119.6, 117.2, 113.1, 112.0, 70.0.

Example 12-4

Synthesis of 1-(4-methoxybenzyl)-2-(4-methoxyphenyl)-1H-benzo[d]imidazole (Compound 116)

In a methanol (5 mL) solvent in the presence of NH$_4$Br (362.3 mg, 3.70 mmol), a solution including 1,2-phenylenediamine (100 mg, 0.92 mmol) and p-anisaldehyde (0.11 mL, 0.82 mmol) was stirred at room temperature for 6 hours, and methanol was evaporated therefrom. The residual was distributed between ethyl acetate and water. An organic layer was dried by using MgSO$_4$, filtered, and evaporated. The residual was purified by silica gel column chromatography using hexane and ethyl acetate (3:1) to obtain a solid Compound 116.

A reaction time of 6 hours; a yield of 38.0%; $^1$H NMR (500 MHz, DMSO-$d_6$) δ 7.84 (d, 1H, J=8.0 Hz), 7.63 (d, 2H, J=8.5 Hz), 7.27 (m, 1H), 7.18 (m, 2H), 6.99 (d, 2H, J=8.5 Hz), 6.94 (d, 2H, J=8.5 Hz), 6.82 (d, 2H, J=9.0 Hz), 5.32 (s, 2H), 3.79 (s, 3H), 3.73 (s, 3H); $^{13}$C NMR (100 MHz, DMSO-$d_6$) δ 161.1, 159.3, 154.3, 143.4, 136.3, 130.9, 128.7, 127.4, 122.9, 122.7, 122.7, 119.9, 114.6, 114.4, 110.7, 55.5, 55.5.

Example 12-4

Synthesis of Compounds 117 and 118

In the case of Compound 117 and 118, in a DMF solvent in the presence of Na$_2$S$_2$O$_5$ (1 eq.), a solution including Compound 97b (1 eq.) and 1,2-phenylenediamine was heated at a temperature of 80° C. for 6.5 hours. After DMF was evaporated therefrom, the residual was distributed between ethyl acetate and water, and the produced precipitate was filtered and the resultant product was washed with a hexane and ethyl acetate (3:1) co-solvent. The obtained filter cake was dissolved in 1,4-dioxane, and 1 N NaOH (1.5 eq.) was added thereto. The reaction mixture was stirred at room temperature for 14 hours, and 1,4-dioxane was evaporated therefrom. The residual was distributed between ethyl acetate and water, an aqueous layer was acidified with 6 N HCl. The produced precipitate was filtered with water to obtain Compounds 117 and 118:

2-(3-(1H-Benzo[d]imidazol-2-yl)phenoxy)-2-methylpropanoic acid (Compound 117)

A reaction time of 6.5 h/14 hours; a yield of 67.7%; $^1$H NMR (500 MHz, DMSO-$d_6$) δ 12.88 (s, 1H), 7.76 (d, 1H, J=7.5 Hz), 7.69 (s, 1H), 7.58 (br s, 2H), 7.43 (t, 1H, J=8.0 Hz), 7.19 (m, 2H), 6.94 (dd, 1H, J=2.5, 8.5 Hz), 1.57 (s, 6H); $^{13}$C NMR (100 MHz, DMSO-$d_6$) δ 175.5, 156.4, 151.5, 143.9, 135.8, 132.0, 130.5, 122.8, 120.5, 120.3, 119.4, 117.1, 112.2, 79.3, 25.8; and 2-(3-(1H-benzo[d]imidazol-2-yl)phenoxy)-2-methylpropanoic acid (Compound 118)

A reaction time of 6.5 hours/14 hours; a yield of 67.7%; $^1$H NMR (500 MHz, DMSO-$d_6$) δ 12.88 (s, 1H), 7.76 (d, 1H, J=7.5 Hz), 7.69 (s, 1H), 7.58 (br s, 2H), 7.43 (t, 1H, J=8.0 Hz), 7.19 (m, 2H), 6.94 (dd, 1H, J=2.5, 8.5 Hz), 1.57 (s, 6H); $^{13}$C NMR (100 MHz, DMSO-$d_6$) δ 175.5, 156.4, 151.5, 143.9, 135.8, 132.0, 130.5, 122.8, 120.5, 120.3, 119.4, 117.1, 112.2, 79.3, 25.8.

Example 12-5

Synthesis of 2-bromo-4-(5-(trifluoromethyl)-2,3-dihydrobenzo[d]thiazol-2-yl)phenol (Compound 119)

In a DMF (3 mL) solvent, a solution including 2-amino-4-trifluoromethylbenzenethiol (100 mg, 0.44 mmol) and 3-bromo-4-hydroxybenzaldehyde (88.4 mg, 0.44 mmol) was heated at a temperature of 100° C. for 2.5 hours. After DMF was evaporated, the residual was distributed between methylene chloride and water, and an organic layer was evaporated. The produced solid was filtered, and washed with ethyl acetate to obtain a solid Compound 119.

A reaction time of 2.5 hours; a yield of 10.5%; $^1$H NMR (400 MHz, DMSO-$d_6$) δ 7.64 (d, 1H, J=1.6 Hz), 7.32 (dd, 1H, J=2.0, 8.4 Hz), 7.04 (d, 1H, J=7.6 Hz), 6.97 (dd, 1H, J=1.2, 8.4 Hz), 6.95 (d, 1H, J=8.0 Hz), 6.76 (s, 1H), 6.58 (s, 1H), 6.38 (d, 1H, J=2.4 Hz), 4.64 (s, 1H); $^{13}$C NMR (100 MHz, DMSO-$d_6$) δ 153.5, 146.6, 134.8, 130.8, 128.2 (q, J=31.8 Hz), 127.7, 124.5 (q, J=270.1 Hz), 121.4, 117.5 (q, J=3.8 Hz), 116.6, 110.6, 105.4 (q, J=3.8 Hz), 69.6.

Example 12-6

Synthesis of 2-(3-(benzo[d]thiazol-2-yl)phenoxy)-2-methylpropanoic acid (Compound 120)

In a methanol solvent, a solution including Compound 97b (1.0 eq.) and 2-aminothiophenol (1.0 eq.) was stirred at room temperature for 22 hours. After methanol was evaporated, the residual was purified by silica gel column chromatography using hexane and ethyl acetate (14:1) as a developer. The obtained product was dissolved with 1,4-dioxane, and then, 1 N NaOH (1.5 eq.) was added thereto. The reaction mixture was stirred at room temperature for 17 hours, and 1,4-dioxane was evaporated. The reaction mixture was stirred at room temperature for 17 hours, and 1,4-dioxane was evaporated therefrom. The residual was distributed between ethyl acetate and water, an aqueous layer was acidified with 6 N HCl. The produced precipitate was filtered and washed with water to obtain Compound 120.

A reaction time of 22 hours/17 hours; a yield of 67.7%; $^1$H NMR (400 MHz, DMSO-$d_6$) δ 13.24 (s, 1H), 8.10 (d, 1H, J=8.0 Hz), 8.02 (d, 1H, J=8.4 Hz), 7.64 (d, 1H, J=7.6 Hz), 7.52 (d, 1H, J=1.2 Hz), 7.50 (d, 1H, J=7.2 Hz), 7.43 (m, 2H), 7.00 (dd, 1H, J=1.2, 7.6 Hz), 1.54 (s, 6H); $^{13}$C NMR (100 MHz, DMSO-$d_6$) δ 175.5, 167.6, 156.6, 154.1, 135.1, 134.6, 131.1, 127.4, 126.3, 123.6, 123.0, 122.1, 121.3, 116.7, 79.5, 25.7.

Example 12-7

Synthesis of 2-(3-(5-chlorobenzo[d]thiazol-2-yl) phenoxy)-2-methylpropanoic acid (Compound 121)

A reaction time of 7 hours; yield 51.3%; $^1$H NMR (400 MHz, DMSO-$d_6$) δ 13.23 (s, 1H), 8.17 (d, 1H, J=8.4 Hz), 8.11 (s, 1H), 7.66 (d, 1H, J=8.0 Hz), 7.49 (m, 2H), 7.46 (t, 1H, J=8.0 Hz), 7.03 (d, 1H, J=8.0 Hz), 1.55 (s, 6H); $^{13}$C NMR (100 MHz, DMSO-$d_6$) δ 175.5, 169.9, 156.7, 155.0, 134.3, 133.9, 132.2, 131.2, 126.4, 124.6, 123.0, 122.4, 121.4, 116.9, 79.6, 25.7.

Example 12-8

Synthesis of 2-(4-(benzo[d]thiazol-2-yl)-2-methoxyphenoxy)-2-methylpropanoic acid (Compound 122)

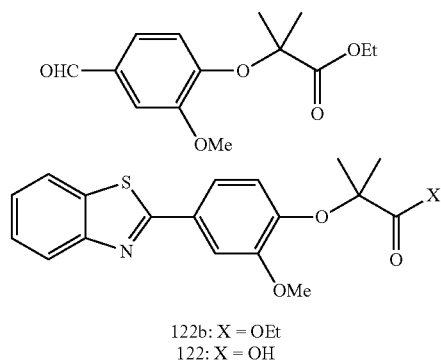

122b: X = OEt
122: X = OH

1) Synthesis of ethyl 2-(4-formyl-2-methoxyphenoxy)-2-methylpropanoate (Compound 122a)

In a co-solvent including ethanol (3 mL) and DMF (3 mL), 1N ethoxy sodium (NaOEt) (2.96 mL, 2.96 mmol) was added dropwise to a solution including vanillin (300 mg, 1.97 mmol) and ethyl α-bromoisobutyrate (0.43 mL, 2.93 mmol), and then, the reaction mixture was heated at a temperature of 80° C. overnight. Ethanol was evaporated, and the residual was distributed between ether and water, and an organic layer was dried, filtered, and evaporated. The residual was purified by silica gel column chromatography using hexane and ethyl acetate (EtOAc) (4:1) to obtain Compound 122a (188.7 mg, 36%).

Yellow oil; a reaction time: overnight; a yield of 36%; $^1$H NMR (400 MHz, CDCl3) δ 9.82 (s, 1H), 7.39 (s, 1H), 7.32 (d, 1H, J=8.4 Hz), 6.81 (d, 1H, J=8.4 Hz), 4.21 (q, 2H, J=7.2 Hz), 3.87 (s, 3H), 1.64 (s, 6H), 1.20 (t, 3H, J=7.2 Hz); $^{13}$C NMR (100 MHz, CDCl$_3$) δ 191.2, 173.8, 151.7, 150.8, 131.3, 125.8, 117.5, 110.2, 80.6, 61.8, 56.1, 25.4, 14.3.

2) Synthesis of ethyl 2-(4-(benzo[d]thiazol-2-yl)-2-methoxyphenoxy)-2-methylpropanoate (Compound 122b)

In a DMF (3 mL) solvent in the presence of Na$_2$S$_2$O$_5$ (136.1 mg, 0.71 mmol), a solution including Compound 122a (188.7 mg, 0.71 mmol) and 2-aminothiophenol (0.08 mL, 0.71 mmol) was stirred at room temperature for 2 days. After DMF was evaporated, the residual was distributed between ethyl acetate and water. An organic layer was dried, filtered, and evaporated. The residual was purified by silica gel column chromatography using hexane and ethyl acetate (EtOAc) (7:1) to obtain Compound 122b (244.8 mg, 93%).

Yellow oil; a reaction time of 2 days; a yield of 93%; $^1$H NMR (400 MHz, CDCl$_3$) δ 8.02 (d, 1H, J=8.0 Hz), 7.86 (d, 1H, J=7.6 Hz), 7.70 (s, 1H), 7.46 (m, 2H), 7.35 (t, 1H, J=6.0 Hz), 6.87 (d, 1H, J=7.2 Hz), 4.24 (q, 2H, J=6.4 Hz), 3.95 (s, 3H), 1.63 (s, 6H), 1.25 (t, 3H, J=6.0 Hz); $^{13}$C NMR (100 MHz, CDCl$_3$) δ 174.2, 168.0, 154.3, 152.0, 147.6, 135.2, 128.6, 126.5, 125.2, 123.2, 121.8, 120.7, 119.6, 110.8, 80.6, 61.7, 56.3, 25.4, 14.4

3) Synthesis of 2-(4-(Benzo[d]thiazol-2-yl)-2-methoxyphenoxy)-2-methylpropanoic acid (Compound 122b)

Compound 122b (244.8 mg, 0.66 mmol) was dissolved with 1,4-dioxane (2 mL), and 1 N NaOH (0.8 mL, 0.8 mmol) was added thereto. The reaction compound was stirred at room temperature, and the reaction mixture was distributed between methylene chloride and water. The reaction compound was stirred at room temperature, and the reaction mixture was distributed between methylene chloride and water. An aqueous layer was acidified with 12 N HCl, and extracted with methylene chloride. An organic layer was evaporated to obtain Compound 122.

White solid; a reaction time of 6.5 hours; a yield of 58%; $^1$H NMR (400 MHz, CDCl$_3$) δ 8.05 (dd, 1H, J=1.2, 8.0 Hz), 7.88 (dd, 1H, J=1.2, 8.8 Hz), 7.74 (d, 1H, J=2.0 Hz), 7.54 (dd, 1H, J=2.0, 8.0 Hz), 7.49 (td, 1H, J=1.2, 8.4 Hz), 7.38 (td, 1H, J=1.2, 8.4 Hz), 7.07 (d, 1H, J=8.0 Hz), 4.01 (s, 3H), 1.57 (s, 6H).

Example 12-9

Synthesis of 4-(benzo[d]oxazol-2-yl)phenol (Compound 123)

In an acetic acid solvent in the presence of sodium acetate (NaOAc) (3.0 eq.), a solution including 2-aminophenol (1.0 eq.) and 4-hydroxybenzaldhehyde (1.0 eq.) was refluxed. After cooling, the reaction mixture was distributed between ethyl acetate and water, and an organic layer was dried, filtered, and evaporated. The residual was purified by silica gel column chromatography using hexane and ethyl acetate (4:1) to obtain a solid Compound 123.

A reaction time of 4 hours; a yield of 7.6%; $^1$H NMR (500 MHz, DMSO-d$_6$) δ 10.34 (s, 1H), 8.03 (d, 2H, J=9.0 Hz), 7.70 (m, 2H), 7.34 (m, 2H), 6.96 (d, 2H, J=8.5 Hz); $^{13}$C NMR (100 MHz, DMSO-d$_6$) δ 163.4, 161.6, 150.7, 142.5, 130.0, 125.4, 125.2, 119.9, 117.8, 116.8, 111.2.

Example 12-10

Synthesis of 2-(4-methoxyphenyl)benzo[d]oxazole (Compound 124)

In an acetic acid solvent in the presence of sodium acetate (NaOAc) (3.0 eq.), a solution including 2-aminophenol (1.0 eq.) and 4-methoxybenzaldhehyde (1.0 eq.) was refluxed. After cooling, the reaction mixture was distributed between ethyl acetate and water, and an organic layer was dried, filtered, and evaporated. The residual was purified by silica gel column chromatography using hexane and acetone (25:1) to obtain a solid Compound 124.

A reaction time of 4 hours; a yield of 6.9%; $^1$H NMR (400 MHz, DMSO-d$_6$) δ 8.17 (d, 2H, J=9.2 Hz), 7.71 (m, 1H), 7.52 (m, 1H), 7.30 (m, 2H), 6.99 (d, 2H, J=9.2 Hz), 3.85 (s, 3H); $^{13}$C NMR (100 MHz, DMSO-d$_6$) δ 163.4, 162.5, 150.9, 142.5, 129.6, 124.8, 124.6, 119.8, 114.6, 110.6, 55.6.

Example 12-11

Synthesis of 2-(3-(benzyloxy)phenyl)-1H-benzo[d]imidazole-5-carboxylic acid (Compound 125)

A reaction time of 5.5 hours; a yield of 42%; $^1$H NMR (500 MHz, DMSO-d$_6$) δ 13.20 (br s, 1H), 7.89 (s, 1H), 7.89-7.86 (m, 2H), 7.82 (d, 1H, J=8.0 Hz), 7.68 (br d, 1H, J=6.0 Hz), 7.52-7.48 (m, 3H), 7.42 (t, 2H, J=7.5 Hz), 7.35 (t, 1H, J=7.5 Hz), 7.18 (dd, 1H, J=2.0, 8.0 Hz), 5.23 (s, 2H).

Example 12-12

Synthesis of 4-(5-chlorobenzo[d]thiazol-2-yl)-2,6-dimethoxyphenol (Compound 126)

In a DMF (3 mL) solvent in the presence of Na$_2$S$_2$O$_5$ (120.3 mg, 0.63 mmol), a solution including 2-amino-4-chlorobenzenethiol (100 mg, 0.63 mmol) and syringaldehyde (115.3 mg, 0.63 mmol) was heated at a temperature of 80° C. for 22 hours. After DMF was evaporated, water was added thereto. The produced precipitate was filtered, and washed with water to obtain Compound 126.

A reaction time of 24 hours; a yield of 47.2%; $^1$H NMR (400 MHz, DMSO-d$_6$) δ 9.29 (s, 1H), 8.09 (dd, 1H, J=2.0, 8.4 Hz), 8.04 (br s, 1H), 7.42 (br d, 1H, J=8.4 Hz), 7.27 (s, 1H), 7.27 (s, 1H), 3.86 (s, 3H), 3.86 (s, 3H); $^{13}$C NMR (100 MHz, DMSO-d$_6$) δ 170.7, 155.2, 148.9, 140.1, 133.7, 131.9, 125.7, 124.2, 123.4, 122.4, 105.5, 56.8.

Example 13

Synthesis of Compounds 127 to 133

Table 8 below is provided to explain substitution patterns of Compounds 127 through 133, which are 2-(substituted phenyl)-5-methyl-1H-benzo[d]imidazole analogs.

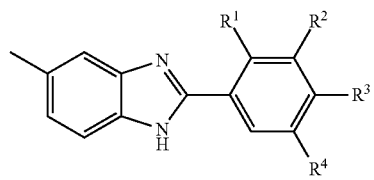

TABLE 8

| Compound | R$^1$ | R$^2$ | R$^3$ | R$^4$ |
|---|---|---|---|---|
| 127 | H | H | OH | H |
| 128 | H | OH | OH | H |
| 129 | OH | H | OH | H |
| 130 | H | OMe | OH | H |
| 131 | H | H | OMe | H |
| 132 | H | OMe | OMe | H |
| 133 | OMe | H | OMe | H |

OMe represents a methoxy group, and OEt represents an ethoxy group.

Compounds 127 to 133 were synthesized as follows. In detail, in a DMF solvent, a solution including benzaldhehyde analogue (1.0 eq.), 3,4-diaminotoluene (1.1 eq.), and Na$_2$S$_2$O$_5$ (4.0 eq.) was heated at a temperature of 100° C. for 42 to 47 hours. After DMF was evaporated, water was added thereto, and the produced precipitate was filtered and washed with water, and a co-solvent including ethyl acetate, methylene chloride, and hexane to obtain Compounds 127 to 133.

Example 13-1

Synthesis of 4-(5-methyl-1H-benzo[d]imidazol-2-yl)phenol (Compound 127)

A reaction time of 42 hours; a yield of 69.0%; $^1$H NMR (400 MHz, DMSO-d$_6$) δ 10.19 (s, 1H), 7.96 (d, 2H, J=8.4 Hz), 7.46 (d, 1H, J=8.4 Hz), 7.36 (s, 1H), 7.06 (d, 1H, J=8.0 Hz) 6.92 (d, 2H, J=8.8 Hz), 2.40 (s, 3H); $^{13}$C NMR (100 MHz, DMSO-d$_6$) δ 160.7, 151.3, 137.3, 135.8, 133.1, 129.3, 125.1, 119.2, 116.6, 114.8, 114.3, 21.9.

Example 13-2

Synthesis of 4-(5-methyl-1H-benzo[d]imidazol-2-yl)benzene-1,2-diol (Compound 128)

A reaction time of 42 hours; a yield of 15.6%; $^1$H NMR (500 MHz, DMSO-d$_6$) δ 9.41 (s, 1H), 9.20 (s, 1H), 7.57 (s, 1H), 7.42 (d, 1H, J=8.0 Hz), 7.39 (d, 1H, J=8.0 Hz), 7.29 (s, 1H), 6.96 (d, 1H, J=8.0 Hz), 6.85 (d, 1H, J=8.0 Hz), 2.40 (s, 3H).

Example 13-3

Synthesis of 4-(5-methyl-1H-benzo[d]imidazol-2-yl)benzene-1,3-diol (Compound 129)

A reaction time of 42 hours; a yield of 98.3%; $^1$H NMR (500 MHz, DMSO-d$_6$) δ 10.20 (s, 1H), 7.84 (d, 1H, J=8.0 Hz), 7.53 (d, 1H, J=8.0 Hz), 7.44 (s, 1H), 7.14 (d, 1H, J=8.0 Hz), 6.48 (d, 1H, J=8.0 Hz) 6.47 (s, 1H), 2.44 (s, 3H); $^{13}$C NMR (100 MHz, DMSO-d$_6$) δ 162.4, 160.2, 150.9, 135.4, 133.6, 129.1, 125.4, 114.5, 114.1, 108.7, 103.8, 103.6, 21.9.

Example 13-4

Synthesis of 2-methoxy-4-(5-methyl-1H-benzo[d]imidazol-2-yl)phenol (Compound 130)

A reaction time of 42 hours; a yield of 21.6%; $^1$H NMR (400 MHz, DMSO-$d_6$) δ 12.53 (br s, 1H), 9.49 (s, 1H), 7.67 (s, 1H), 7.54 (d, 1H, J=8.0 Hz), 7.38 (d, 1H, J=7.6 Hz), 7.28 (s, 1H), 6.94 (d, 1H, J=8.8 Hz), 6.86 (d, 1H, J=8.4 Hz) 3.84 (s, 3H), 2.37 (s, 3H).

Example 13-5

Synthesis of 2-(4-methoxyphenyl)-5-methyl-1H-benzo[d]imidazole (Compound 131)

A reaction time of 42 hours; a yield of 43.4%; $^1$H NMR (400 MHz, DMSO-$d_6$) δ 8.08 (d, 2H, J=8.4 Hz), 7.52 (d, 1H, J=8.0 Hz), 7.42 (s, 1H), 7.15 (m, 3H), 3.82 (s, 3H), 2.42 (s, 3H); $^{13}$C NMR (100 MHz, DMSO-$d_6$) δ 162.4, 150.5, 136.3, 134.7, 134.0, 129.5, 125.8, 119.6, 115.4, 114.7, 114.3, 56.2, 21.9.

Example 13-6

Synthesis of 2-(3,4-dimethoxyphenyl)-5-methyl-1H-benzo[d]imidazole (Compound 132)

A reaction time of 42 hours; a yield of 77.1%; $^1$H NMR (400 MHz, DMSO-$d_6$) δ 7.72 (m, 2H), 7.51 (d, 1H, J=8.4 Hz), 7.41 (s, 1H), 7.15 (d, 1H, J=8.8 Hz), 7.11 (d, 1H, J=8.0 Hz), 3.85 (s, 3H), 3.82 (s, 3H), 2.41 (s, 3H); $^{13}$C NMR (100 MHz, DMSO-$d_6$) δ 152.0, 150.7, 149.7, 136.6, 135.0, 133.7, 125.6, 120.9, 120.0, 114.8, 114.3, 112.6, 110.6, 56.4, 56.4, 21.9.

Example 13-7

Synthesis of 2-(2,4-dimethoxyphenyl)-5-methyl-1H-benzo[d]imidazole (Compound 133)

A reaction time of 47 hours; a yield of 88.7%; $^1$H NMR (400 MHz, DMSO-$d_6$) δ 11.83 (brs, 1H), 8.18 (d, 1H, J=8.8 Hz), 7.40 (d, 1H, J=8.4 Hz), 7.32 (s, 1H), 6.93 (d, 1H, J=8.4 Hz), 6.70 (s, 1H), 6.66 (d, 1H, J=8.8 Hz), 3.96 (s, 3H), 3.80 (s, 3H), 2.37 (s, 3H); $^{13}$C NMR (100 MHz, DMSO-$d_6$) δ 151.1, 149.7, 146.5, 136.3, 134.7, 133.7, 125.6, 119.9, 118.4, 116.7, 115.0, 114.6, 114.2, 21.9.

Example 14

Synthesis of Compounds 134 to 138

Table 9 below is provided to explain substitution patterns of Compounds 134 to 138, which are 2-(substituted phenyl)-5-nitro-1H-benzo[d]imidazole analogs.

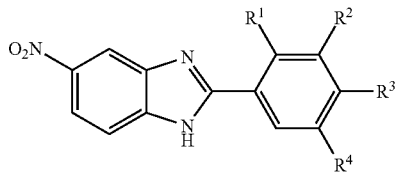

TABLE 9

| Compound | R$^1$ | R$^2$ | R$^3$ | R$^4$ |
|---|---|---|---|---|
| 134 | H | H | OH | H |
| 135 | H | OMe | OH | H |
| 136 | H | OH | OMe | H |
| 137 | H | H | OMe | H |
| 138 | H | OMe | OH | OMe |

OMe indicates a methoxy group.

Compounds 134 to 138 were synthesized as follows. In detail, in a DMF solvent, a solution including substituted benzaldhehyde (1.3 eq.), 4-nitro-1,2-phenylenediamine (1.0 eq.), and Na$_2$S$_2$O$_5$ (1.1 eq.) was heated at a temperature of 80° C. After DMF was evaporated, water was added thereto, and the produced precipitate was filtered, and washed with water. The filter cake was re-crystallized with methanol to obtain Compounds 134 to 138.

Example 14-1

Synthesis of 4-(5-nitro-1H-benzo[d]imidazol-2-yl)phenol (Compound 134)

Yellow solid; a reaction time of 6 hours; a yield of 62.2%; $^1$H NMR (500 MHz, DMSO-$d_6$) δ 13.2 (s, 1H), 10.18 (s, 1H), 8.42 (s, 0.5H), 8.25 (s, 0.5H), 8.05 (m, 3H), 7.64 (br s, 1H) 6.94 (d, 2H, J=9.0 Hz).

Example 14-2

Synthesis of 2-methoxy-4-(5-nitro-1H-benzo[d]imidazol-2-yl)phenol (Compound 135)

Yellow solid; a reaction time of 6 hours; a yield of 23.6%; $^1$H NMR (500 MHz, DMSO-$d_6$) δ 13.32 (s, 1H), 9.74 (s, 1H), 8.45 (s, 0.5H), 8.28 (s, 0.5H), 8.07 (d, 1H, J=7.0 Hz), 7.76 (s, 1H), 7.70-7.64 (m, 2H), 6.95 (d, 1H, J=8.5 Hz), 3.89 (s, 3H).

Example 14-3

Synthesis of 2-methoxy-5-(5-nitro-1H-benzo[d]imidazol-2-yl)phenol (Compound 136)

Yellow solid; a reaction time of 7.5 hours; a yield of 35.7%; $^1$H NMR (500 MHz, DMSO-$d_6$) δ 13.33 (s, 1H), 9.41 (s, 1H), 8.39 (s, 0.5H), 8.08 (s, 0.5H), 8.08 (d, 1H, J=8.0 Hz), 7.64 (m, 3H), 7.11 (d, 1H, J=8.0 Hz), 3.85 (s, 3H).

Example 14-4

Synthesis of 2-(4-methoxyphenyl)-5-nitro-1H-benzo[d]imidazole (Compound 137)

Yellow solid; a reaction time of 6 hours; a yield of 7.6%; $^1$H NMR (500 MHz, DMSO-$d_6$) δ 13.39 (s, 1H), 8.46 (s, 0.5H), 8.28 (s, 0.5H), 8.13 (d, 2H, J=8.5 Hz), 8.09 (br d, 1H, J=7.5 Hz), 7.75 (d, 0.5H, J=7.0 Hz), 7.63 (d, 0.5H, J=7.5 Hz), 7.12 (d, 2H, J=8.5 Hz), 3.83 (s, 3H).

Example 14-5

Synthesis of 2,6-dimethoxy-4-(5-nitro-1H-benzo[d]imidazol-2-yl)phenol (Compound 138)

Yellow solid; a reaction time of 18 hours; a yield of 19.9%; $^1$H NMR (500 MHz, DMSO-$d_6$) δ 9.12 (br s, 1H), 8.40 (s, 1H), 8.09 (d, 1H, J=9.0 Hz), 7.71 (d, 1H, J=8.5 Hz), 7.52 (s, 2H), 3.88 (s, 6H).

Experimental Example 1

In Vitro ROS Scavenging Activity Assay

1. Preparation of Vascular Endothelial Cells (YPEN-1)

YPEN-1 cells (rat prostatic endothelial cell line) was obtained from American type culture collection (ATCC, Manassas, Va., USA), and the cells were cultured by using a dulbecco's modified eagle medium (DMEM, Nissui, Tokyo, Japan) containing 2 mM L-glutamine, 100 mg/ml streptomycin, 2.5 mg/L amphotericin B, and 5% inactivated fetal bovine serum (FBS). Also, the cells were maintained at a temperature of 37° C. in a humid atmosphere-like condition containing 5% $CO_2$ and 95% air. Also, a medium that did not contain 5% FBS was used as a serum-free medium (SFM). The cells were sub-cultured in 100 mm plastic flask (Corning Co., New York, USA) every two days to maintain the cell line.

2. ROS Measurement

2',7'-dichlorodihydrofluorescein diacetate (DCFDA) assay method according to a conventionally known method (Chem Res Toxicol. 5: 227-231, 1992) was used. In detail, 12.5 mM DCFDA dissolved in 99.9% ethanol and 600 U/ml esterase dissolved in tertiary distilled water were stored as a stock solution at a temperature of −20° C., and a 2',7'-dichlorodihydrofluorescein (DCFH) solution prepared by mixing 10 mM DCFDA and 6 U/ml esterase was cultured at a temperature of 22° C. for 20 minutes, and then, refrigerated in a dark place before use. Since the oil-soluble DCFDA was deacetylated into non-fluorescent DCFH due to esterase or oxidative hydrolysis and the DCFH was oxidized due to activity oxygen to produce highly-fluorescent 2',7'-dichlorofluorescein (DCF), the present measurement was performed at an excitation wavelength of 485 nm and an emission wavelength of 530 nm by using a fluorophotometer (GENios, TECAN). Vascular endothelial cells that were pre-treated with 50 μM 3-morpholinosydnonimine hydrochloride (SIN-1) for 1 hour were used as a reactive oxygen generation source.

Figure 2:
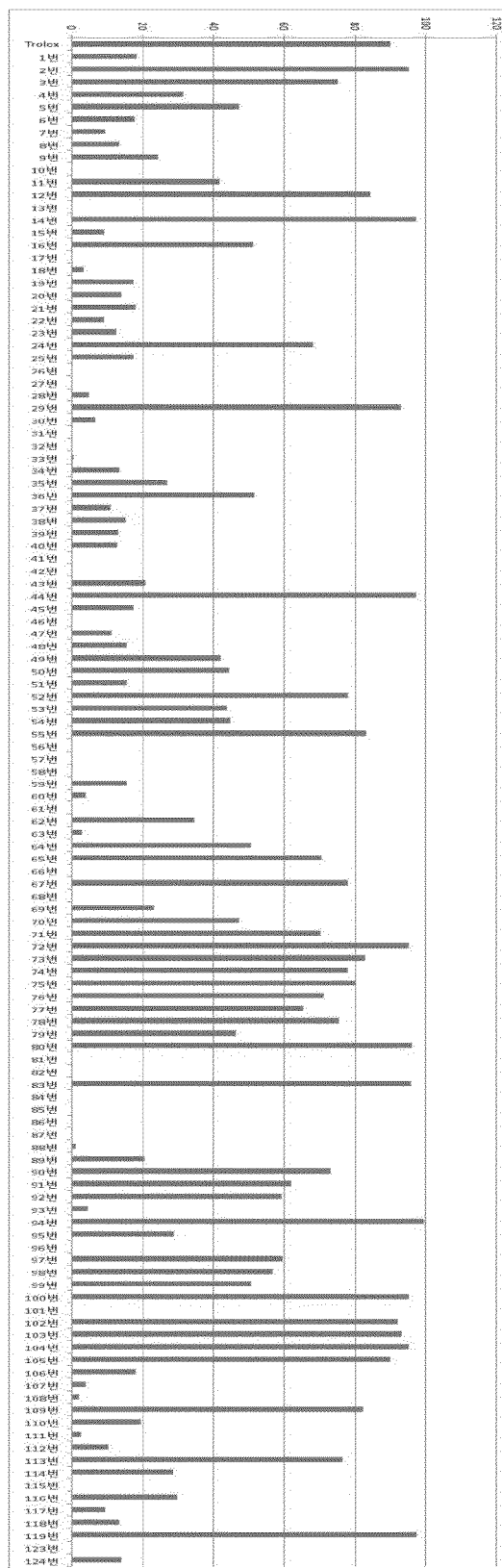

As a result, as shown in FIGS. 1 and 2, Compounds 2, 14, 29, 44, 72, 80, 83, 94, 100, 102, 103, 104, 105, and 119 were screened out as a compound that has as high scavenging effects on ROS generated by vascular endothelial cells as trolox, which was used as a positive control.

Experimental Example 2

Tyrosinase Inhibitory Effect

Mushroom-derived tyrosinase was sued as an enzyme source in the present experiment. Tyrosinase activities were assayed according to a slightly-modified conventionally known method (Life Sci., 1999, 65, 241-246). In detail, 20 μl of a mushroom-derived tyrosinase (1000 units) aqueous solution was added to 96-well microplate (Nunc, Denmark) to prepare 200 μl of the total volume of assay mixture containing 1 mM L-tyrosin solution and 50 mM phosphate buffer solution (pH 6.5). The assay mixture was cultured at a temperature of 25° C. for 30 minutes. After the culturing, an amount of the produced DOPA chrome in the reaction mixture was measured by using a microplate reader (Hewlett Packard) at 492 nm ($OD_{492}$).

Figure 3:
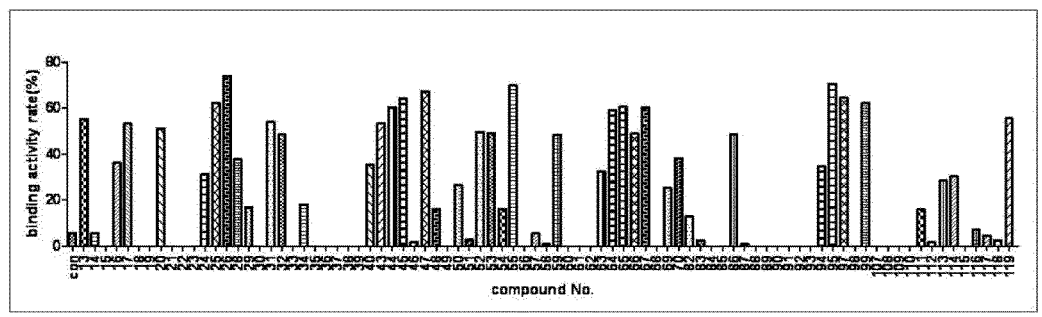
FIGS. 3 and 4 are graphs showing tyrosinase suppression activities of a compound according to the present invention.
Figure 4:
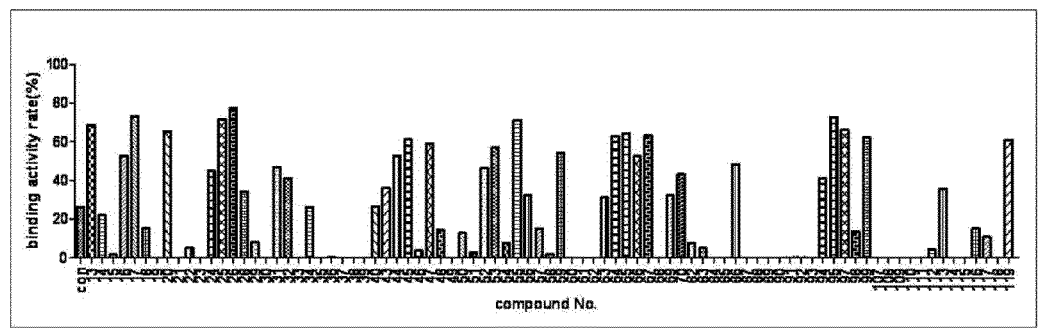

As a result, as shown in FIGS. 3 and 4, Compounds 3, 9, 13, 15, 30, 45, 55, 82, 83, 94, 99, and 101 were screened out as a compound that has better tyrosinase inhibitory activities than a kojic acid, which was used as a positive control.

Experimental Example 3

PPAR Assay

20 μl of a sample and 10 μl of 4× fluormone Pan-PPAR green were spread onto 384 well plates, and 10 μl of 4×PPAR alpha-LBD/Tb-anti-GST antibody or 10 μl of 4×PPAR gamma-LBD/Tb-anti-GST antibody were respectively used in PPARα assay and PPARγ assay. In this regard, a sample compound was dissolved in such an amount of DMSO that made a final concentration of the sample to be 100 μM, and the DMSO final concentration was maintained within 1%. The reaction mixture was left at room temperature for 2 to 6 hours, and then, the absorption thereof was measured by using a microplate reader (Hewlett Packard) at an excitation wavelength of 340 nm and at an emission wavelength of 485 nm, and at an exitation wavelength of 340 nm and an emission wavelength of 520 nm to calculate a value of 520 nm/485 nm. In this regard, if a negative control was assumed to have an absorption value of 100, a competitive activation rate was defined as follows: 100 minus an absorption value of each sample. That is, the competitive activation rate indicates a binding ratio of the respective samples with respect to the negative control.

1. PPARα

To evaluate PPARα activities, evaluation values were divided in three scales since the binding activity of fenofibrate, which was used as a positive control, was not high. In detail, a value (3 to 10) that was similar to that of the positive control was indicated as '≈feno', a value (10 to 25) that was slightly higher than that of the positive control was indicated as '>feno', and a value (25 or more) that was much higher than that of the positive control was indicated as '>>feno', and a material that has a higher value than a negative control during measurement was designated as 'ND'. The presence of ND was due to the fluorescence of sample compounds themselves.

Figure 5:
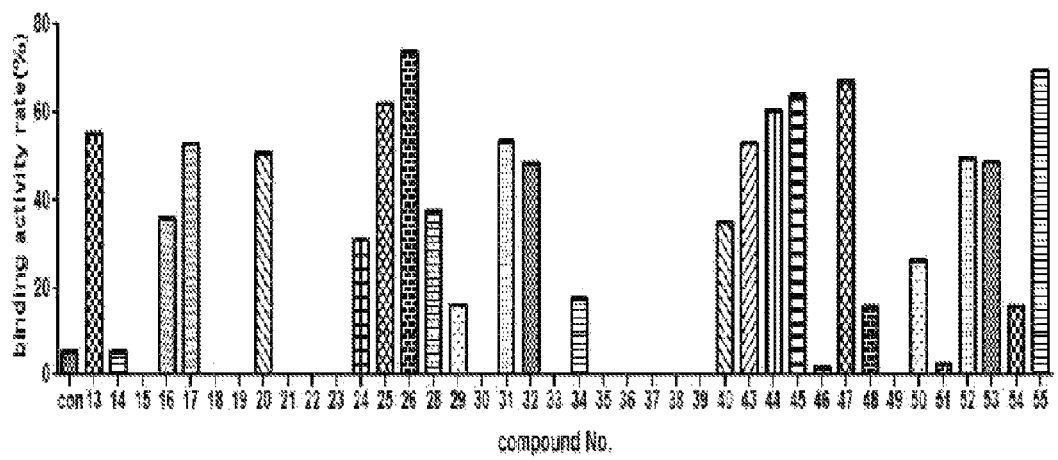
FIGS. 5 and 6 are graphs showing PPARα enhancement activities of a compound according to the present invention.
Figure 6:
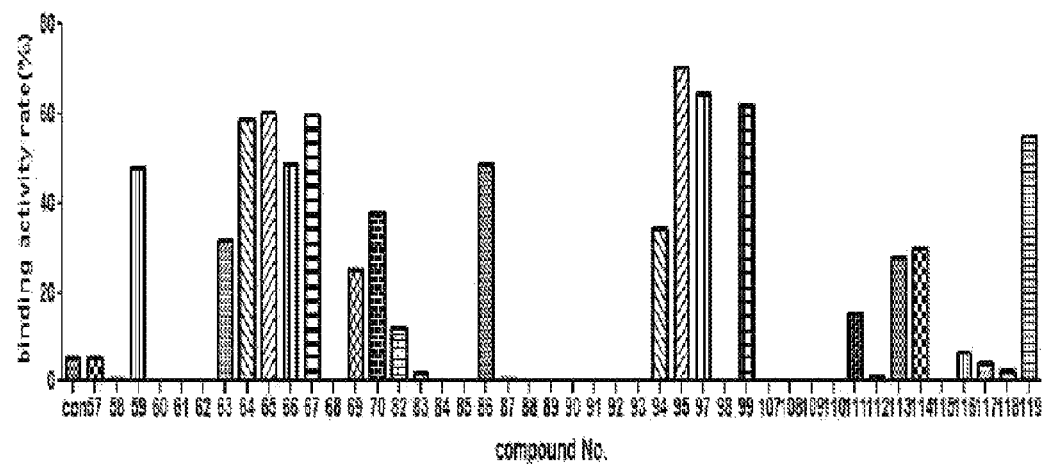

As shown in FIGS. 5 and 6, Compounds 13, 16, 17, 20, 24, 25, 26, 28, 31, 32, 40, 43, 44, 45, 47, 52, 53, 55, 59, 63, 64, 65, 66, 67, 69, 70, 86, 94, 95, 97, 99, 113, 114, and 119 were confirmed as a very excellent PPARα activation agent compared to fenofibrate, which was used as a positive control, and in particular, Compound 26 was confirmed to be the most excellent PPARα activation agent.

2. PPARγ

To evaluate PPARγ a material that has an activity similar to that of rosiglitazone was indicated as '≈Rosi', and a material that has a higher activity than that of rosiglitazoneivity was indicated as '>Rosi', and like PPARα, a material that has a higher value than a negative control during measurement was designated as 'ND'.

Figure 7:
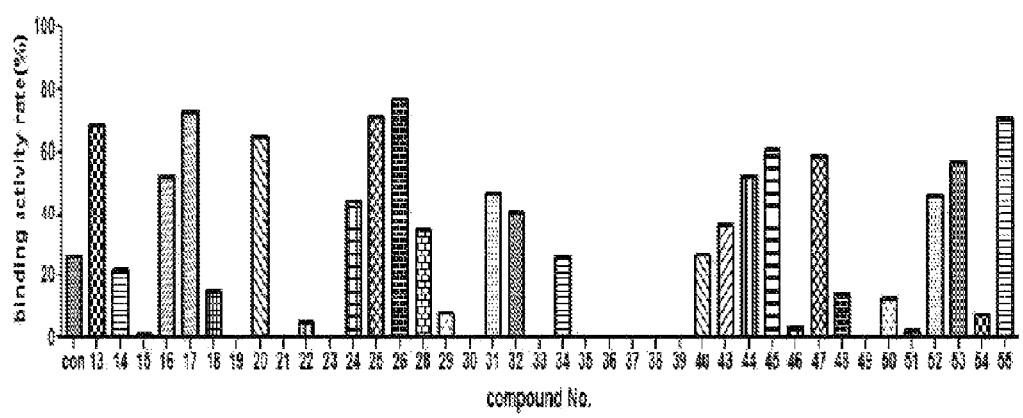
FIGS. 7 and 8 are graphs showing PPARγ enhancement activities of a compound according to the present invention.
Figure 8:
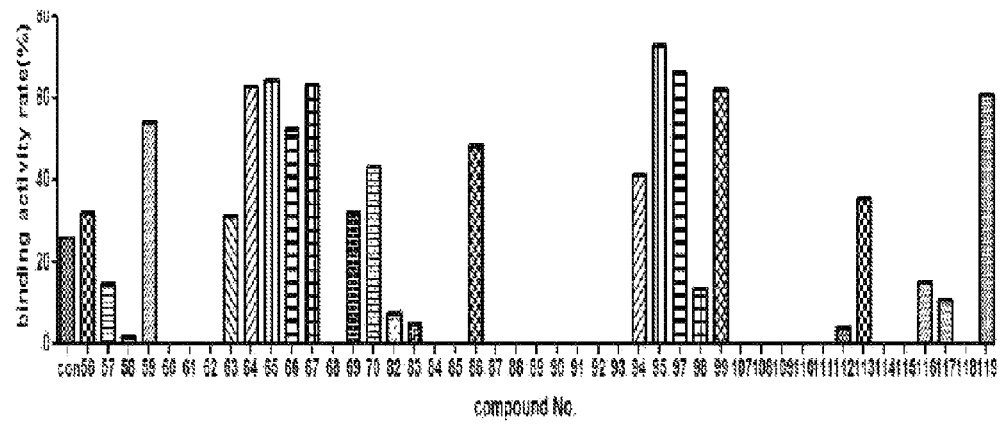

As shown in FIGS. 7 and 8, Compounds 13, 16, 17, 20, 24, 25, 26, 28, 31, 32, 34, 40, 43, 44, 45, 47, 52, 53, 55, 56, 59, 63, 64, 65, 66, 67, 69, 70, 86, 94, 95, 97, 99, 113, and 119 were confirmed as a very excellent PPARγ activation agent compared to rosiglitazone, which was used as a positive control, and in particular, Compound 26 was confirmed to be the most excellent PPARγ activation agent.

In particular, Compound 13, Compound 16, Compound 17, Compound 20, Compound 24, Compound 25, Compound 26, Compound 28, Compound 31, Compound 32, Compound 40, Compound 43, Compound 44, Compound 45, Compound 47, Compound 52, Compound 53, Compound 55, Compound 59, Compound 63, Compound 64, Compound 65, Compound 66, Compound 67, Compound 69, Compound 70, Compound 86, Compound 94, Compound 95, Compound 97, Compound 99, Compound 113, and Compound 119 were identified as an activation agent that simultaneously activates PPARα and PPARγ.

Experimental Example 4

Toxicity Test

A suspension of each of Compound 26, Compound 28, Compound 47, Compound 67, Compound 86, Compound 94, Compound 97, Compound 99, Compound 113, and Compound 119 in a 0.5% methylcellulose solution was orally administered once to a male Balb/c mouse in dosages of 0.5 g/kg, 1 g/kg, and 2 g/kg, and then the survival rate and body weight of the mouse was recorded for 7 days.

After the administration, whether the mouse died, clinical symptoms occurred, and body weight changed were identified and hematologic examination and blood biochemical examination were performed, and autopsy was performed to identify with naked eyes states of abdominal cavity organs and thoracic cavity organs.

As a result, all the animals neither had distinctive clinical symptoms nor died, and even in consideration of body weight change, hematologic examination results, blood biochemical examination results, and autopsy referral, toxicity change was not identified.

As shown in these results, compounds according to the present invention did not have the toxicity change in up to 2 g/kg of rats, and accordingly, it was considered that the compounds were safe in view that a median lethal dose (LD50) thereof for oral administration was 2 g/kg or more.

Hereinafter, preparation examples of a composition including Compound 26 according to the present invention will be described in detail. However, the preparation examples are provided for illustrative purpose only and do not limit the scope of the invention.

Prescription Example 1

Prescription Example of Pharmaceutical Composition

Prescription Example 1-1

Preparation of Powder Formulation 20 mg of Compound 26, 100 mg of lactose, and 10 mg of talc were mixed and then a sealing package was filled therewith to prepare a powder formulation.

Prescription Example 1-2

Preparation of Tablet Formulation 20 mg of Compound 26, 100 mg of corn starch, 100 mg of lactose, and 2 mg of magnesium stearate were mixed, and then, the mixture was tabulated according to a conventional tablet preparation method to prepare a tablet formulation.

Prescription Example 1-3

Preparation of Capsule Formulation 10 mg of Compound 26, 100 mg of corn starch, 100 mg of lactose, and 2 mg of magnesium stearate were mixed according to a conventional capsule preparation method, and then, a gelain capsule was filled with the mixture to prepare a capsule formulation Prescription Example 1-4

Preparation of Injection Formulation 10 mg of Compound 26, an appropriate amount of sterilized distilled water for injection, and an appropriate amount of a pH controller were mixed and then, according to a conventional injection formulation preparation method, an injection preparation was prepared in such a way that one ample (2 ml) has the components in the amounts described above.

Prescription Example 1-5

Preparation of Ointment Formulation 10 mg of Compound 26, 250 mg of PEG-4000, 650 mg of PEG-400, 10 mg of white vaseline, 1.44 mg of methyl p-hydroxybenzoate, 0.18 mg of propyl p-hydroxybenzoate, and the balanced amount of purified water were mixed, and then, the mixture was used to prepare an ointment formulation according to a conventional ointment preparation method.

Prescription Example 2

Prescription Example of Cosmetic Composition

Prescription Example 2-1

Preparation of Nutrition Lotion 3.0 parts by weight of propylene glycol, 0.1 parts by weight of carboxypolymer, a trace of a preservative, and the balanced amount of purified water were mixed by stirring while heating to a temperature of 80 to 85° C. The mixture was loaded into a preparation unit, and then, an emulsifying machine was driven, and 1.0 part by weight of polysolvate 60, 0.5 parts by weight of sorbitan sesquiolate, 10.0 parts by weight of liquid paraffin, 1.0 part by weight of sorbitan stearate, 0.5 parts by weight of lipophilic glyceryl monostearate, 1.5 parts by weight of stearic acid, 1.0 part by weight of glyceryl stearate/PEG-400 stearate, and 0.2 parts by weight of triethanolamine were heated to a temperature of 80 to 85° C., and then, loaded thereinto to perform emulsification. When the emulsifying was completely performed, the mixture was stirred by using an agitator while heat-cooling to a temperature of 50° C., and then, a trace of flavoring agent was added thereto, and after cooling to a temperature of 45° C., a trace of pigment was added thereto, and Compound 26 was added thereto at a temperature of 35° C. and the resultant mixture was cooled to a temperature of 25° C. and aged.

Prescription Example 2-2

Preparation of Nutrition Cream 0.3 parts by weight of carboxypolymer, 5.0 parts by weight of butylene glycol, 3.0 parts by weight of glycerin, and the balanced amount of purified water were mixed by stirring while heating to a temperature of 80 to 85° C., and the mixture was loaded into a preparation unit, and then, an emulsifying machine was driven. Then, 2.0 parts by weight of a stearic acid, 2.0 parts by weight of cetylalcohol, 2.0 parts by weight of glyceryl monostearate, 0.5 parts by weight of polyoxyethylenesorbitanmonostearate, 0.5 parts by weight of sorbitansesquiolate, 1.0 part by weight of wax, 1.0 part by weight of glyceryl monostearate/glyceryl stearate/polyoxyethylene stearate, 4.0 parts by weight of liquid paraffin, 4.0 parts by weight of squalane, and 4.0 parts by weight of caprylic/capric triglyceride were heated to at temperature of 80 to 85° C. and then loaded thereinto, and then, 0.5 parts by weight of triethanolamine was loaded thereinto and emulsifying was performed thereon. When the emulsifying was completely performed, the resultant mixture was stirred by using an agitator while cooling to a temperature of 35° C., and then, Compound 26 was loaded thereinto and cooled to a temperature of 25° C. and aged.

Prescription Example 2-3

Preparation of Washfoam 30.0 parts by weight of TEA-cocoyl glutamate, 10.0 parts by weight of disodium laureth sulfosuccinateglycerin, 10.0 parts by weight of glycerin, 2.0 parts by weight of cocamide DEA, 1.0 part by weight of PEG-120 methylglucose dioliate, 0.5 parts by weight of methyl gluceth-20, 0.5 parts by weight of PEG-150 pentaerythrityl tetra stearate, 0.05 parts by weight of tetrasodium EDTA, and a trace of preservative were sequentially added into a preparation unit, and then, heated to a temperature of 60 to 65° C. and then stirred for 15 minutes. When the stirring was completely performed, some of purified water was added therein and then the resultant mixture was stirred for 30 minutes, and then, some of purified water was slowly added thereinto and then the resultant mixture was stirred for 30 minutes, and then cooled to a temperature of 35° C., and Compound 26 and a flavoring agent were added thereinto, and then, the resultant mixture was cooled to a temperature of 25° C. and aged.

Prescription Example 3

Supplementary Health Food

Prescription Example 3-1

Preparation of Health Foods 1 mg of Compound 26, an appropriate amount of vitamin mixture (including 70 μg of vitamin A acetate, 1.0 mg of vitamin E, 0.13 mg of vitamin B 1, 0.15 mg of vitamin B 2, 0.5 mg of vitamin B 6, 0.2 μg of vitamin B 12, 10 mg of vitamin C, 10 μg of biotin, 1.7 mg of nicotinamide, 50 μg of folate, and 0.5 mg of calcium pantothenate), and an appropriate amount of mineral mixture (1.75 mg of ferrous sulphate, 0.82 mg of zinc oxide, 25.3 mg of magnesium carbonate, 15 mg of potassium phosphate monobasic, 55 mg of calcium phosphate dibasic, 90 mg of potassium citrate, 100 mg of calcium carbonate, and 24.8 mg of magnesium chloride) were mixed, and then, prepared in a granule formulation, and then, a health food was prepared according to a conventional method.

Prescription Example 3-2

Preparation of Health Beverages 1 mg of Compound 26, 1000 mg of a citric acid, 100 g of oligosaccharide, 2 g of plum concentrate, 1 g of taurine, and such an amount of purified water that a total volume of the mixture reached 900 ml were prepared, and these components were mixed according to a conventional health beverage preparation method, and then, the mixture was stirred for about 1 hour while heating at a temperature of 85° C., and then the prepared solution was filtered, and a sterilized 2 L container was filled therewith and then, sealed and sterilized, and then, refrigerated.

What is claimed is:
1. A skin-whitening method, comprising:
administering to a subject a compound of Formula I,

[Formula I]

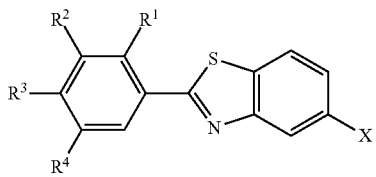

wherein $R^1$ to $R^4$ are identical to or different from each other, and are any one of H, OH, a $C_1$ to $C_4$ alkoxy, and bromine,
wherein X is any one of Cl and $CF_3$.
2. The skin-whitening method of claim 1, wherein the compound is selected from the group consisting of 4-(5-(trifluoromethyl)benzo[d]thiazol-2-yl)phenol (Compound 28), 4-(5-(trifluoromethyl)benzo[d]thiazol-2-yl)benzene-1,2-diol (Compound 29), 4-(5-(trifluoromethyl)benzo[d]thiazol-2-yl)benzene-1,3-diol (Compound 30), 2-methoxy-4-(5-(trifluoromethyl)benzo[d]thiazol-2-yl)phenol (Compound 31), 2-ethoxy-4-(5-(trifluoromethyl)benzo[d]thiazol-2-yl)phenol (Compound 32), 2-(4-methoxyphenyl)-5-(trifluoromethyl)benzo[d]thiazol (Compound 34), 2-(2,4-dimethoxyphenyl)-5-(trifluoromethyl)benzo[d]thiazol (Compound 37), and 2,6-dimethoxy-4-(5-(trifluoromethyl)benzo[d]thiazol-2-yl)phenol (Compound 40).
3. The skin-whitening method of claim 2, wherein the compound is administered to the subject in a range of 0.001 to 100 mg/kg daily.
4. The skin-whitening method of claim 1, wherein the compound is selected from the group consisting of 4-(5-chlorobenzo[d]thiazol-2-yl)phenol (Compound 82), 4-(5-chlorobenzo[d]thiazol-2-yl)benzene-1,2-diol (Compound 83), 4-(5-chlorobenzo[d]thiazol-2-yl)benzene-1,3-diol (Compound 84), 4-(5-chlorobenzo[d]thiazol-2-yl)-2-ethoxyphenol (Compound 86), 2-bromo-4-(5-chlorobenzo[d]thiazol-2-yl)phenol (Compound 95), 2,6-dibromo-4-(5-chlorobenzo[d]thiazol-2-yl)phenol (Compound 96), and 4-(5-chlorobenzo[d]thiazol-2-yl)-2,6-dimethoxyphenol (Compound 126).
5. The skin-whitening method of claim 4, wherein the compound is administered to the subject in a range of 0.001 to 100 mg/kg daily.
6. A skin-whitening method, comprising:
administering to a subject a compound selected from the group consisting of 4-(5-(trifluoromethyl)benzo[d]thiazol-2-yl)phenol (Compound 28), 4-(5-(trifluoromethyl)benzo[d]thiazol-2-yl)benzene-1,2-diol (Compound 29), 4-(5-(trifluoromethyl)benzo[d]thiazol-2-yl)benzene-1,3-diol (Compound 30), 2-methoxy-4-(5-(trifluoromethyl)benzo[d]thiazol-2-yl)phenol (Compound 31), 2-ethoxy-4-(5-(trifluoromethyl)benzo[d]thiazol-2-yl)phenol (Compound 32), 2-(4-methoxyphenyl)-5-(trifluoromethyl)benzo[d]thiazole (Compound 34), 2-(2,4-dimethoxyphenyl)-5-(trifluoromethyl)benzo[d]thiazole (Compound 37), and 2,6-dimethoxy-4-(5-(trifluoromethyl)benzo[d]thiazol-2-yl)phenol (Compound 40).

7. The skin-whitening method of claim 6, wherein the compound is administered to the subject in a range of 0.001 to 100 mg/kg daily.

* * * * *